(12) United States Patent
Ichikawa et al.

(10) Patent No.: US 8,431,326 B2
(45) Date of Patent: Apr. 30, 2013

(54) SALT AND PHOTORESIST COMPOSITION COMPRISING THE SAME

(75) Inventors: Koji Ichikawa, Osaka (JP); Mitsuyoshi Ochiai, Osaka (JP); Takashi Hiraoka, Osaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 21 days.

(21) Appl. No.: 13/251,334

(22) Filed: Oct. 3, 2011

(65) Prior Publication Data

US 2012/0088190 A1 Apr. 12, 2012

(30) Foreign Application Priority Data

Oct. 6, 2010 (JP) ................. 2010-226609

(51) Int. Cl.
*G03F 7/004* (2006.01)
*G03F 7/30* (2006.01)
*C07C 309/65* (2006.01)
*C07C 309/71* (2006.01)
*C07D 321/10* (2006.01)
*C07D 321/12* (2006.01)

(52) U.S. Cl.
USPC ........ 430/270.1; 430/326; 430/330; 430/910; 549/333; 549/340; 562/100; 562/108; 562/109; 562/113

(58) Field of Classification Search ............... 430/270.1, 430/326, 330, 910; 549/333, 340; 562/100, 562/108, 109, 113
See application file for complete search history.

(56) References Cited

U.S. PATENT DOCUMENTS

| | | |
|---|---|---|
| 2003/0194639 A1 | 10/2003 | Miya et al. |
| 2006/0194982 A1 | 8/2006 | Harada et al. |
| 2011/0014568 A1 | 1/2011 | Ichikawa et al. |
| 2011/0200936 A1* | 8/2011 | Ichikawa et al. ........... 430/270.1 |
| 2012/0135351 A1* | 5/2012 | Ichikawa et al. ........... 430/285.1 |

* cited by examiner

*Primary Examiner* — John Chu
(74) *Attorney, Agent, or Firm* — Birch, Stewart, Kolasch & Birch, LLP

(57) ABSTRACT

The present invention provides a salt represented by the formula (I):

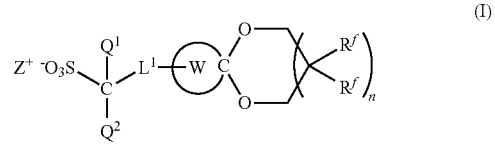

wherein $Q^1$ and $Q^2$ independently each represent a fluorine atom or a C1-C6 perfluoroalkyl group, $L^1$ represents a C1-C17 divalent saturated hydrocarbon group in which one or more —$CH_2$— can be replaced by —O— or —CO—, ring W represents a C3-C36 aliphatic ring in which one or more —$CH_2$— can be replaced by —O—, —S—, —CO— or —$SO_2$— and in which one or more hydrogen atoms can be replaced by a hydroxyl group, a C1-C12 alkyl group, a C1-C12 alkoxy group, a C3-C12 alicyclic hydrocarbon group or a C6-C10 aromatic hydrocarbon group, $R^f$ is independently in each occurrence a fluorine atom or a C1-C6 fluorinated alkyl group, n represents an integer of 1 to 10, and $Z^+$ represents an organic counter ion.

8 Claims, No Drawings

SALT AND PHOTORESIST COMPOSITION COMPRISING THE SAME

This nonprovisional application claims priority under 35 U.S.C. §119(a) on Patent Application No. 2010-226609 filed in JAPAN on Oct. 6, 2010, the entire contents of which are hereby incorporated by reference.

FIELD OF THE INVENTION

The present invention relates to a salt and a photoresist composition comprising the same.

BACKGROUND OF THE INVENTION

A photoresist composition is used for semiconductor microfabrication employing a lithography process.

US 2003/0194639 A1 discloses a salt represented by the following formula:

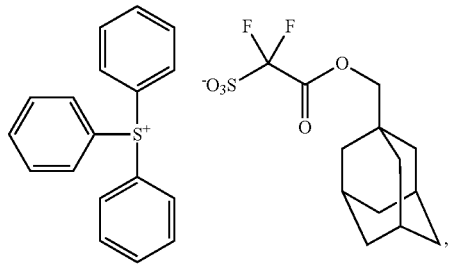

and a photoresist composition containing the same as an acid generator.

SUMMARY OF THE INVENTION

The present invention is to provide a salt for suitable for an acid generator and a photoresist composition comprising the same.

The present invention relates to the followings:

<1> A salt represented by the formula (I):

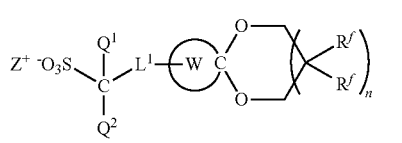

(I)

wherein $Q^1$ and $Q^2$ independently each represent a fluorine atom or a C1-C6 perfluoroalkyl group, $L^1$ represents a C1-C17 divalent saturated hydrocarbon group in which one or more —$CH_2$— can be replaced by —O— or —CO—, ring W represents a C3-C36 aliphatic ring in which one or more —$CH_2$— can be replaced by —O—, —S—, —CO— or —$SO_2$— and in which one or more hydrogen atoms can be replaced by a hydroxyl group, a C1-C12 alkyl group, a C1-C12 alkoxy group, a C3-C12 alicyclic hydrocarbon group or a C6-C10 aromatic hydrocarbon group, $R^f$ is independently in each occurrence a fluorine atom or a C1-C6 fluorinated alkyl group, n represents an integer of 1 to 10, and $Z^+$ represents an organic counter ion;

<2> The salt according to <1>, wherein ring W is a ring represented by the formula (Ia1-1), (Ia1-2) or (Ia1-3):

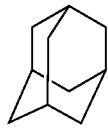
(Ia1-1)

(Ia1-2)

(Ia1-3)

wherein one or more —$CH_2$— in the above-mentioned formula can be replaced by —O—, —S—, —CO— or —$SO_2$— and one or more hydrogen atoms can be replaced by a hydroxyl group, a C1-C12 alkyl group, a C1-C12 alkoxy group, a C3-C12 alicyclic hydrocarbon group or a C6-C10 aromatic hydrocarbon group;

<3> The salt according to <1> or <2>, wherein $L^1$ is *—CO—O—$(CH_2)_t$— in which * represents a binding position to —$C(Q^1)(Q^2)$- and t represents an integer of 0 to 6;

<4> The salt according to any one of <1> to <3>, wherein $Z^+$ is an arylsulfonium cation;

<5> An acid generator comprising the salt according to any one of <1> to <4>;

<6> A photoresist composition comprising the acid generator according to <5> and a resin having an acid-labile group, being insoluble or poorly soluble in an aqueous alkali solution but becoming soluble in an aqueous alkali solution by the action of an acid;

<7> The photoresist composition according to <6>, which further comprises a basic compound;

<8> A process for producing a photoresist pattern comprising the following steps (1) to (5):

(1) a step of applying the photoresist composition according to <6> or <7> on a substrate, (2) a step of forming a photoresist film by conducting drying, (3) a step of exposing the photoresist film to radiation, (4) a step of baking the exposed photoresist film, and (5) a step of developing the baked photoresist film with an alkaline developer, thereby forming a photoresist pattern.

DESCRIPTION OF PREFERRED EMBODIMENTS

First, the salt represented by the formula (I) will be, illustrated.

The salt of the present invention is represented by the formula (I):

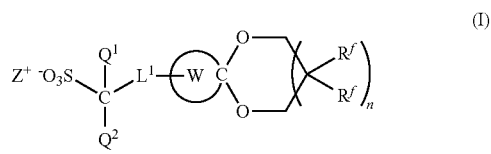

(I)

wherein $Q^1$ and $Q^2$ independently each represent a fluorine atom or a C1-C6 perfluoroalkyl group, $L^1$ represents a C1-C17 divalent saturated hydrocarbon group in which one or more —$CH_2$— can be replaced by —O— or —CO—, ring W represents a C3-C36 aliphatic ring in which one or more —$CH_2$— can be replaced by —O—, —S—, —CO— or —$SO_2$— and in which one or more hydrogen atoms can be replaced by a hydroxyl group, a C1-C12 alkyl group, a C1-C12 alkoxy group, a C3-C12 alicyclic hydrocarbon group or a C6-C10 aromatic hydrocarbon group, $R^f$ is independently in each occurrence a fluorine atom or a C1-C6 fluorinated alkyl group, n represents an integer of 1 to 10, and $Z^+$ represents an organic counter ion (hereinafter, simply referred to as SALT (I)).

Examples of the C1-C6 perfluoroalkyl group include a trifluoromethyl group, a perfluoroethyl group, a perfluoropropyl group, a perfluoroisopropyl group, a perfluorobutyl group, a perfluoro-sec-butyl group, a perfluoro-tert-butyl group, a perfluoropentyl group and a perfluorohexyl group, and a trifluoromethyl group is preferable. It is preferred that $Q^1$ and $Q^2$ independently each represent a fluorine atom or a trifluoromethyl group, and it is more preferred that $Q^1$ and $Q^2$ are fluorine atoms.

Examples of the C1-C17 divalent saturated hydrocarbon group include a C1-C17 linear alkanediyl group such as a methylene group, an ethylene group, a propane-1,3-diyl group, a propane-1,2-diyl group, a butane-1,4-diyl group, a butane-1,3-diyl group, a pentane-1,5-diyl group, a hexane-1,6-diyl group, a heptane-1,7-diyl group, an octane-1,8-diyl group, a nonane-1,9-diyl group, a decane-1,10-diyl group, a undecane-1,11-diyl group, a dodecane-1,12-diyl group, a tridecane-1,13-diyl group, a tetradecane-1,14-diyl group, a pentadecane-1,15-diyl group, a hexadecane-1,16-diyl group, a heptadecane-1,17-diyl group, an ethane-1,1-diyl group, a propane-1,1-diyl group and a propane-2,2-diyl group; a C2-C17 branched alkanediyl group such as a butane-1,3-diyl group, a 2-methylpropane-1,3-diyl group, a 2-methylpropane-1,2-diyl group, a pentane-1,4-diyl group and a 2-methylbutane-1,4-diyl group; a divalent monocyclic saturated hydrocarbon group such as a cyclobutane-1,3-diyl group, a cyclopentane-1,3-diyl group, a cyclohexane-1,2-diyl group, a 1-methylcyclohexane-1,2-diyl group, a cyclohexane-1,4-diyl group, a cyclooctane-1,2-diyl group and a cyclooctane-1,5-diyl group; a divalent polycyclic saturated hydrocarbon group such as a norbornane-2,3-diyl group, a norbornane-1,4-diyl group, a norbornane-2,5-diyl group, an adamantane-1,2-diyl group, an adamantane-1,5-diyl group and an adamantane-2,6-diyl group; and a group formed by combining two or more groups selected from the group consisting of the above-mentioned groups.

When $L^1$ represents a C1-C17 divalent saturated hydrocarbon group in which one or more —$CH_2$— are replaced by —O— or —CO—, examples thereof include *—CO—O-$L^{b2}$-, *—CO—O-$L^{b4}$-CO—O-$L^{b3}$-, *-$L^{b5}$-O—CO—, *-$L^{b7}$-O-$L^{b6}$-, *—CO—O-$L^{b8}$-O—, *—CO—O-$L^{b10}$-O-$L^{b9}$-CO—O— and *—O-$L^{b12}$-CO—O-$L^{b11}$-, wherein $L^{b2}$ represents a single bond or a C1-C15 divalent saturated hydrocarbon group, $L^{b3}$ represents a single bond or a C1-C12 divalent saturated hydrocarbon group, $L^{b4}$ represents C1-C13 divalent saturated hydrocarbon group, with the proviso that total carbon number of $L^{b3}$ and $L^{b4}$ is 1 to 13, $L^{b5}$ represents a C1-C15 divalent saturated hydrocarbon group, $L^{b6}$ represents a C1-C15 divalent saturated hydrocarbon group, $L^{b7}$ represents a C1-C15 divalent saturated hydrocarbon group, with the proviso that total carbon number of $L^{b6}$ and $L^{b7}$ is 1 to 16, $L^{b8}$ represents a C1-C14 divalent saturated hydrocarbon group, $L^{b9}$ represents a single bond or a C1-C11 divalent saturated hydrocarbon group, $L^{b10}$ represents a C1-C12 divalent saturated hydrocarbon group, with the proviso that total carbon number of $L^{b9}$ and $L^{b10}$ is 1 to 12, $L^{b11}$ represents a single bond or a C1-C13 divalent saturated hydrocarbon group, $L^{b12}$ represents a C1-C14 divalent saturated hydrocarbon group, with the proviso that total carbon number of $L^{b11}$ and $L^{b12}$ is 1 to 14 and * represents a binding position to —$C(Q^1)(Q^2)$-. $L^1$ is preferably *—CO—O-$L^{b2}$-, and $L^1$ is more preferably *—CO—O-$L^{b2}$- in which $L^{b2}$ is a single bond or —CO—O—$(CH_2)_t$— in which t represents an integer of 1 to 6, and $L^1$ is especially preferably *—CO—O-$L^{b2}$- in which $L^{b2}$ is a single bond or —$CH_2$—.

Examples of *—CO—O-$L^{b2}$- include *—CO—O— and *—CO—O—$CH_2$—. Examples of *—CO—O-$L^{b4}$-CO—O-$L^{b3}$- include *—CO—O—$CH_2$—CO—O—, —CO—O—$(CH_2)_2$—CO—O—, *—CO—O—$(CH_2)_3$—CO—O—, *—CO—O—$(CH_2)_4$—CO—O—, —CO—O—$(CH_2)_6$—CO—O—, *—CO—O—$(CH_2)_8$—CO—O—, *—CO—O—$CH_2$—$CH(CH_3)$—CO—O—, —CO—O—$CH_2$—$C(CH_3)_2$—CO—O—, *—CO—O—$CH_2$—CO—O—$CH_2$—, —CO—O—$CH_2$—CO—O—$(CH_2)_2$—, and the following:

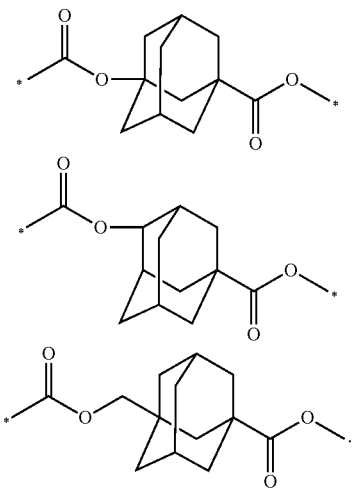

Examples of *-$L^{b5}$-O—CO— include *—$CH_2$—O—CO—, *—$(CH_2)_2$—O—CO—, —$(CH_2)_3$—O—CO—, *—$(CH_2)_4$—O—CO—, *—$(CH_2)_6$—O—CO— and *—$(CH_2)_8$—O—CO—.

Examples of *-$L^{b7}$-O-$L^{b6}$- include *—$CH_2$—O—$CH_2$—.

Examples of *—CO—O-$L^{b8}$-O— include *—CO—O—$CH_2$—O—, —CO—O—$(CH_2)_2$—O—, *—CO—O—$(CH_2)_3$—O—, *—CO—O—$(CH_2)_4$—O— and —CO—O—$(CH_2)_6$—O—.

Examples of *—CO—O-$L^{b10}$-O-$L^{b9}$-CO—O— include the following.

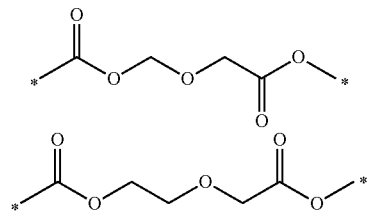

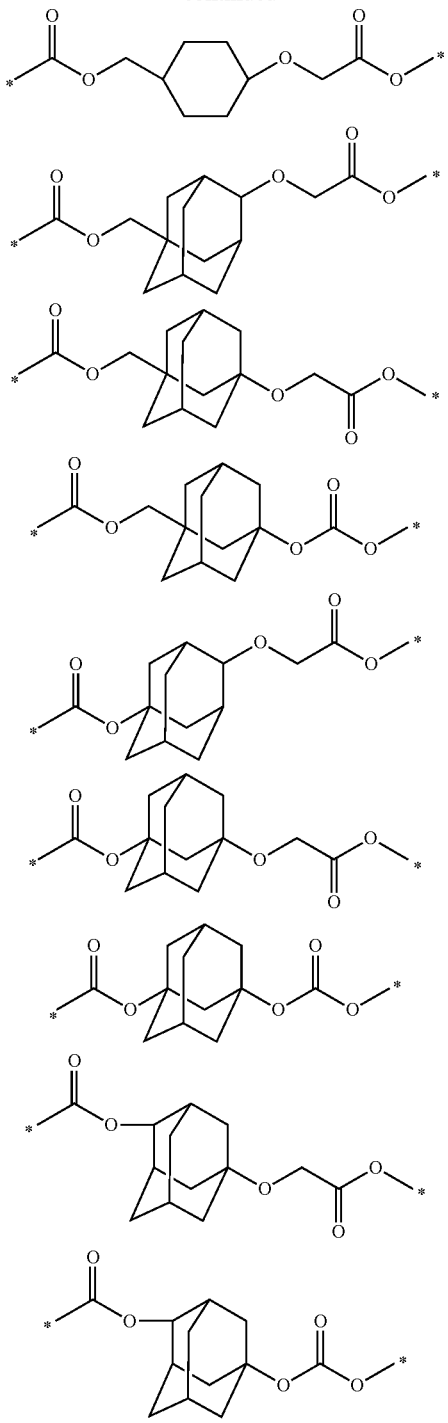

Examples of *—O—L$^{b12}$—CO—O—L$^{b11}$- include *—O—CH$_2$—CO—O—, —O—(CH$_2$)$_2$—CO—O—, *—O—(CH$_2$)$_3$—CO—O—, *—O—(CH$_2$)$_4$—CO—O—, —O—(CH$_2$)$_6$—CO—O—, *—O—(CH$_2$)$_8$—CO—O—, *—O—CH$_2$—CH(CH$_3$)—CO—O—, and —O—CH$_2$—C(CH$_3$)$_2$—CO—O—.

The C3-C36 aliphatic ring represented by ring W preferably has no unsaturated bond. Examples of the aliphatic ring include the following rings represented by the formulae (Ia1-1), (Ia1-2) and (Ia1-3):

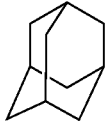
(Ia1-1)

(Ia1-2)

(Ia1-3)

wherein one or more —CH$_2$— in the above-mentioned formula can be replaced by —O—, —S—, —CO— or —SO$_2$— and one or more hydrogen atoms can be replaced by a hydroxyl group, a C1-C12 alkyl group, a C1-C12 alkoxy group, a C3-C12 alicyclic hydrocarbon group or a C6-C10 aromatic hydrocarbon group.

Examples of the C1-C12 alkyl group include a methyl group, an ethyl group, a propyl group, a butyl group, a pentyl group, a hexyl group, a heptyl group and an octyl group.

Examples of the C1-C12 alkoxy group include a methoxy group, an ethoxy group, a propoxy group, an isopropoxy group, a butoxy group, a sec-butoxy group, a tert-butoxy group, a pentyloxy group and a hexyloxy group.

Examples of the C3-C12 alicyclic hydrocarbon group include a cyclopentyl group, a cyclohexyl group, a methylcyclohexyl group, a dimethylcyclohexyl group, a cycloheptyl group, a cyclooctyl group, an adamantyl group and a norbornyl group.

Examples of the C6-C10 aromatic hydrocarbon group include a phenyl group, a naphthyl group, an anthryl group, a p-methylphenyl group, a p-tert-butylphenyl group, a p-adamantylphenyl group, a tolyl group, a xylyl group, a cumyl group, a mesityl group, a biphenyl group, a phenanthryl group, a 2,6-dimethylphenyl group, a 2-methyl-5-ethylphenyl group.

Examples of the C1-C6 fluorinated alkyl group represented by R$^f$ include a difluoromethyl group, a trifluoromethyl group, a 1,1-difluoroethyl group, a 2,2-difluoroethyl group, a 2,2,2-trifluoroethyl group, a perfluoroethyl group, a 1,1,2,2-tetrafluoropropyl group, a 1,1,2,2,3,3-hexafluoropropyl group, a (perfluoroethyl)methyl group, a 1-(trifluoromethyl)-1,2,2,2-tetrafluoroethyl group, a perfluoropropyl group, a 1,1,2,2-tetrafluorobutyl group, a 1,1,2,2,3,3-hexafluorobutyl group, a 1,1,2,2,3,3,4,4-octafluorobutyl group, a perfluorobutyl group, a 1,1-bis(trifluoromethyl)-2,2,2-trifluoroethyl group, 2-(perfluoropropyl)ethyl group, a 1,1,2,2,3,3,4,4-octafluoropentyl group, a perfluoropentyl group, a 1,1,2,2,3,3,4,4,5,5-decafluoropentyl group, a 1,1-bis(trifluoromethyl)-2,2,3,3,3,-pentafluoropropyl group, a perfluoropentyl group, a 2-(perfluorobutyl)ethyl group, a 1,1,2,2,3,3,4,4,5,5-decafluorohexyl group, a 1,1,2,2,3,3,4,4,5,5,6,6-dodecafluorohexyl group, a (perfluoropentyl)methyl group and a perfluorohexyl group. Among them, preferred is a C1-C4 fluorinated alkyl group, and more preferred are a trifluoromethyl group, a perfluoroethyl group, a perfluoropropyl group and a perfluorobutyl group.

Two R$^f$ may be the same or different from each other.

R$^f$s are preferably fluorine atoms.

Examples of the anion part of SALT (I) include the following.

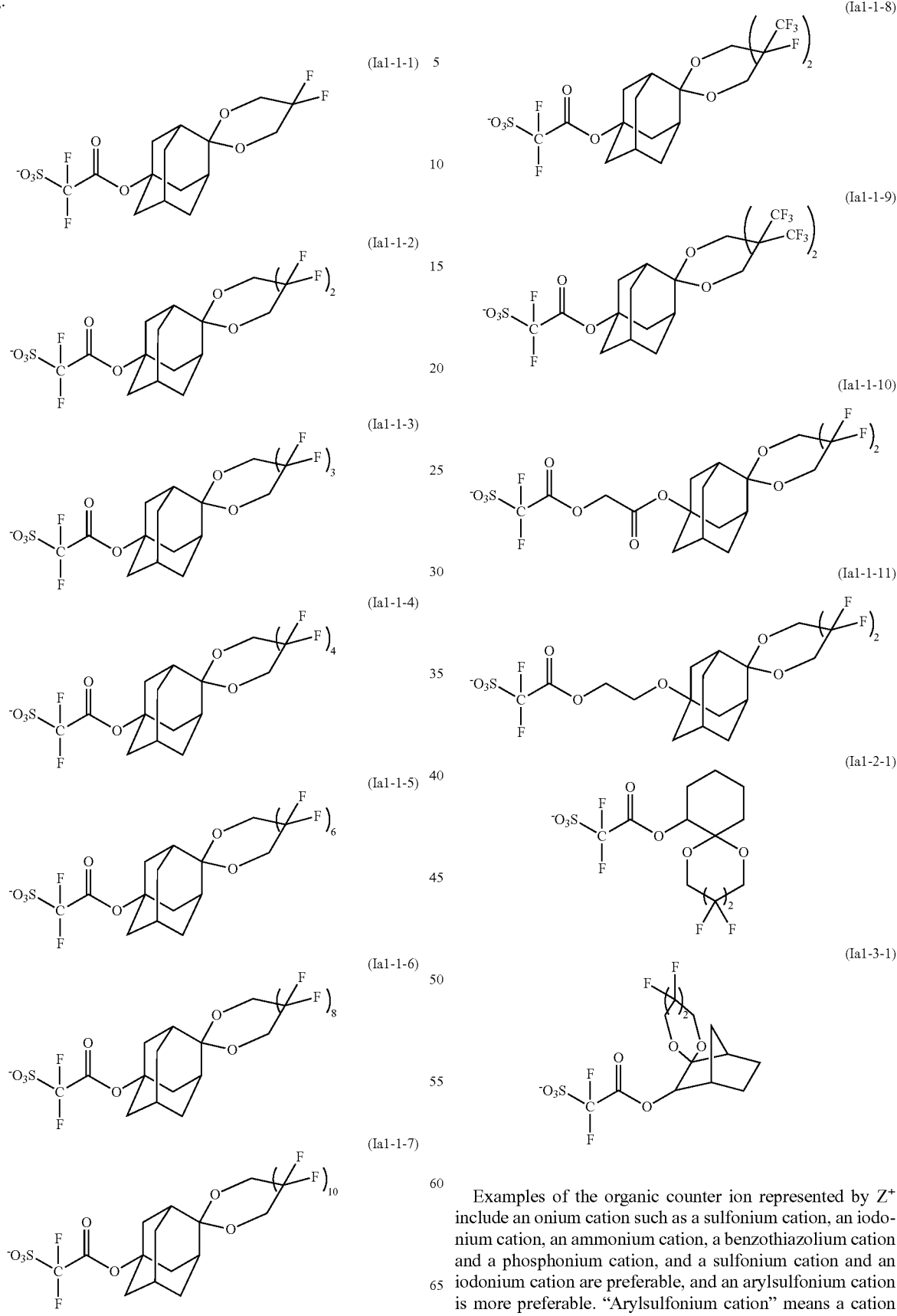

Examples of the organic counter ion represented by Z$^+$ include an onium cation such as a sulfonium cation, an iodonium cation, an ammonium cation, a benzothiazolium cation and a phosphonium cation, and a sulfonium cation and an iodonium cation are preferable, and an arylsulfonium cation is more preferable. "Arylsulfonium cation" means a cation having at least one aryl group.

Preferable examples of the organic counter ion represented by $Z^+$ include the organic cations represented by the formulae (b2-1) to (b2-4):

(b2-1)

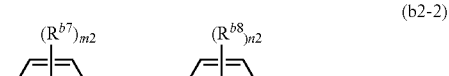
(b2-2)

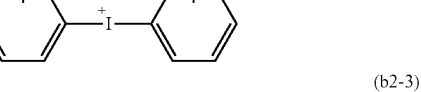
(b2-3)

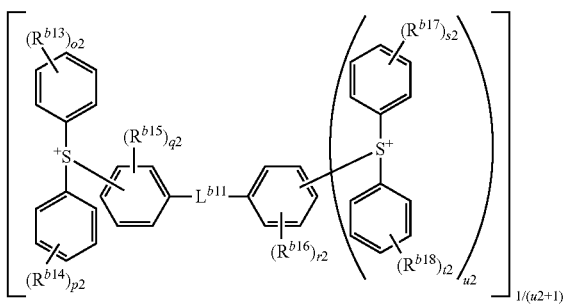
(b2-4)

wherein $R^{b4}$, $R^{b5}$ and $R^{b6}$ independently represent a C1-C30 aliphatic hydrocarbon group which can have one or more substituents selected from the group consisting of a hydroxyl group, a C1-C12 alkoxy group and a C6-C18 aromatic hydrocarbon group, a C3-C18 saturated cyclic hydrocarbon group which can have one or more substituents selected from the group consisting of a halogen atom, a C2-C4 acyl group and a glycidyloxy group, or a C6-C18 aromatic hydrocarbon group which can have one or more substituents selected from the group consisting of a halogen atom, a hydroxyl group, a C1-C18 aliphatic hydrocarbon group, a C3-C18 saturated cyclic hydrocarbon group and a C1-C12 alkoxy group, and $R^{b4}$ and $R^{b5}$, $R^{b4}$ and $R^{b6}$, or $R^{b5}$ and $R^{b6}$ can be bonded each other to form a ring containing $S^+$, $R^{b7}$ and $R^{b8}$ are independently in each occurrence a hydroxyl group, a C1-C12 aliphatic hydrocarbon group or a C1-C12 alkoxy group, m2 and n2 independently represents an integer of 0 to 5, $R^{b9}$ and $R^{b10}$ independently represent a C1-C18 aliphatic hydrocarbon group or a C3-C18 saturated cyclic hydrocarbon group, or $R^{b9}$ and $R^{b10}$ are bonded to form a C2-C11 divalent acyclic hydrocarbon group which forms a ring together with the adjacent $S^+$, and one or more —CH$_2$— in the divalent acyclic hydrocarbon group may be replaced by —CO—, —O— or —S—, and $R^{b11}$ represents a hydrogen atom, a C1-C18 aliphatic hydrocarbon group, a C3-C18 saturated cyclic hydrocarbon group or a C6-C18 aromatic hydrocarbon group, $R^{b12}$ represents a C1-C12 aliphatic hydrocarbon group, a C3-C18 saturated cyclic hydrocarbon group or a C6-C18 aromatic hydrocarbon group and the aromatic hydrocarbon group can have one or more substituents selected from the group consisting of a C1-C12 aliphatic hydrocarbon group, a C1-C12 alkoxy group, a C3-C18 saturated cyclic hydrocarbon group and a C2-C13 acyloxy group, or $R^{b11}$ and $R^{b12}$ are bonded each other to form a C1-C10 divalent acyclic hydrocarbon group which forms a 2-oxocycloalkyl group together with the adjacent —CHCO—, and one or more —CH$_2$— in the divalent acyclic hydrocarbon group may be replaced by —CO—, —O— or —S—, and $R^{b13}$, $R^{b14}$, $R^{b15}$, $R^{b16}$, $R^{b17}$ and $R^{b18}$ independently represent a hydroxyl group, a C1-C12 aliphatic hydrocarbon group or a C1-C12 alkoxy group, $L^{b11}$ represents —S— or —O— and o2, p2, s2 and t2 each independently represents an integer of 0 to 5, q2 and r2 each independently represents an integer of 0 to 4, and u2 represents 0 or 1.

The aliphatic hydrocarbon group represented by $R^{b9}$ to $R^{b11}$ has preferably 1 to 12 carbon atoms. The saturated cyclic hydrocarbon group represented by $R^{b9}$ to $R^{b11}$ has preferably 3 to 18 carbon atoms and more preferably 4 to 12 carbon atoms.

Preferable examples of the aliphatic hydrocarbon group represented by $R^{b4}$ to $R^{b6}$ include an alkyl group such as a methyl group, an ethyl group, a propyl group, an isopropyl group, a butyl group, a sec-butyl group, a tert-butyl group, a pentyl group, a hexyl group, an octyl group, a decyl group, a dodecyl group, a hexadecyl group, a pentadecyl group, a heptadecyl group and an octadecyl group, and more preferable examples thereof include a methyl group, an ethyl group, a propyl group and a butyl group. Preferable examples of the saturated cyclic hydrocarbon group represented by $R^{b4}$ to $R^{b6}$ include a cyclopentyl group, a cyclohexyl group, an adamantyl group and an isobornyl group, and more preferable examples thereof include a cyclopentyl group and a cyclohexyl group. Preferable examples of the aromatic group include represented by $R^{b4}$ to $R^{b6}$ a phenyl group, a naphthyl group and an anthryl group, and a phenyl group is more preferable. Examples of the C1-C12 alkoxy group include a methoxy group, an ethoxy group, a propoxy group, a butoxy group, a pentyloxy group, a hexyloxy group, a heptyloxy group, an octyloxy group, a decyloxy group and a dodecyloxy group. Examples of the halogen atom include a fluorine atom, a chlorine atom, a bromine atom and an iodine atom. Examples of the C2-C4 acyl group include an acetyl group, a propyonyl group and a butyryl group.

The ring containing $S^+$ formed by bonding $R^{b4}$ and $R^{b5}$, $R^{b4}$ and $R^{b6}$, or $R^{b5}$ and $R^{b6}$ each other may be a monocyclic ring, a polycyclic ring, an aromatic ring, a non-aromatic ring, a saturated ring or a unsaturated ring. The ring can contain one or more sulfur atom or oxygen atom in addition to $S^+$. The ring preferably has 3 to 18 carbon atoms, and more preferably has 4 to 13 carbon atoms.

Preferable examples of the aliphatic hydrocarbon group represented by $R^{b9}$ to $R^{b12}$ include a methyl group, an ethyl group, a propyl group, an isopropyl group, a butyl group, a sec-butyl group, a tert-butyl group, a pentyl group, a hexyl group, an octyl group and a 2-ethylhexyl group Preferable examples of the saturated cyclic hydrocarbon group represented by $R^{b9}$ to $R^{b11}$ include a cyclopropyl group, a cyclobutyl group, a cyclopentyl group, a cyclohexyl group, a cycloheptyl group, a cyclodecyl group, a 2-alkyl-2-adamantyl group, a 1-(1-adamantyl)-1-alkyl group and an isobornyl group. Preferable examples of the aromatic group represented by $R^{b11}$ to $R^{b12}$ include a phenyl group, a 4-methylphenyl group, a 4-ethylphenyl group, a 4-tert-butylphenyl group, a 4-cyclohexylphenyl group, a 4-methoxyphenyl group, a biphenyl group and a naphthyl group. Examples of the aliphatic hydrocarbon group having an aromatic hydrocarbon group include a benzyl group.

Examples of the C3-C12 divalent acyclic hydrocarbon group formed by bonding $R^{b9}$ and $R^{b10}$ include a trimethylene group, a tetramethylene group and a pentamethylene group. Examples of the ring group formed together with the adjacent $S^+$ and the divalent acyclic hydrocarbon group include a thiolan-1-ium ring (tetrahydrothiphenium ring), a thian-1-ium ring and a 1,4-oxathian-4-ium ring. A C3-C7 divalent acyclic hydrocarbon group is preferable.

Examples of the C1-C10 divalent acyclic hydrocarbon group formed by bonding $R^{b11}$ and $R^{b12}$ include a methylene group, an ethylene group, a trimethylene group, a tetramethylene group and a pentamethylene group and examples of the ring group include the followings.

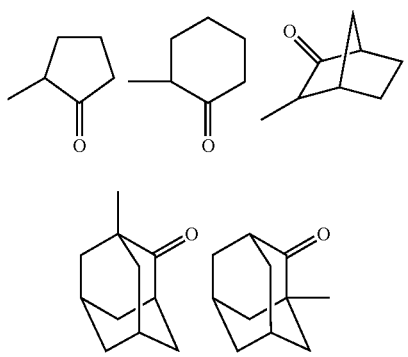

A C1-C5 divalent acyclic hydrocarbon group is preferable.

Examples of the C2-C13 acyloxy group include an acetyloxy group, a propyonyloxy group, a butyryloxy group, an isopropylcarbonyloxy group, a butylcarbonyloxy group, a sec-butylcarbonyloxy group, a tert-butylcarbonyloxy group, a pentylcarbonyloxy group, a hexylcarbonyloxy group, an octylcarbonyloxy group and a 2-ethylhexylcarbonyloxy group.

Among the above-mentioned cations, preferred is the cation represented by the formula (b2-1), and more preferred is the cation represented by the formula (b2-1-1). A triphenylsulfonium cation and a trytolysulfonium cation are especially preferable.

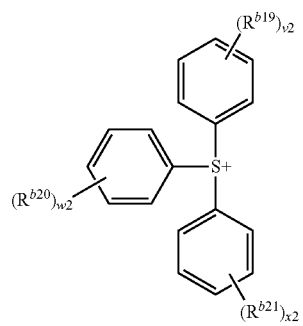

(b2-1-1)

wherein $R^{b19}$, $R^{b20}$ and $R^{b21}$ are independently in each occurrence a halogen atom (preferably a fluorine atom), a hydroxyl group, a C1-C18 aliphatic hydrocarbon group, a C3-C18 saturated cyclic hydrocarbon group or a C1-C12 alkoxy group, and one or more hydrogen atoms of the aliphatic hydrocarbon group can be replaced by a hydroxyl group, a C1-C12 alkoxy group or a C6-C18 aromatic hydrocarbon group, and one or more hydrogen atoms of the saturated cyclic hydrocarbon group can be replaced by a halogen atom, a glycidyloxy group or a C2-C4 acyl group, and $R^{b19}$ and $R^{b20}$, $R^{b19}$ and $R^{b21}$ or $R^{b20}$ and $R^{b21}$ can be bonded each other to form a single bond, —O— or a C1-C4 aliphatic divalent hydrocarbon group which forms a sulfur containing ring together with $S^+$ and v2, w2 and x2 independently each represent an integer of 0 to 5.

The aliphatic hydrocarbon, group has preferably 1 to 12 carbon atoms, and the saturated cyclic hydrocarbon group has preferably 4 to 18 carbon atoms, and v2, w2 and x2 independently each preferably represent 0 or 1.

It is preferred, that $R^{b19}$, $R^{b20}$ and $R^{b21}$ are independently in each occurrence a halogen atom, a hydroxyl group, a C1-C12 alkyl group or a C1-C12 alkoxy group, and v2, w2 and x2 independently each represent an integer of 0 to 5. It is more preferred that $R^{b19}$, $R^{b20}$ and $R^{b21}$ are independently in each occurrence a fluorine atom, a hydroxyl group, a C1-C12 alkyl group or a C1-C12 alkoxy group, and v2, w2 and x2 independently each represent 0 or 1.

Examples of the cation represented by the formula (b2-1) include the following.

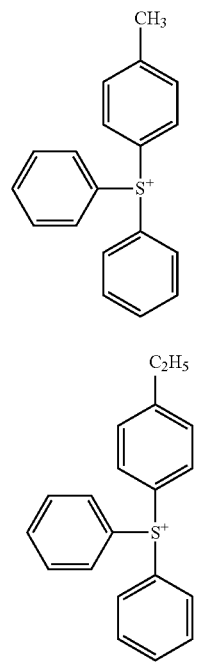

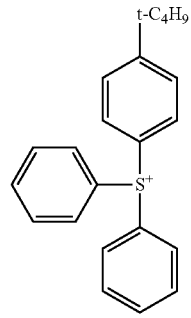

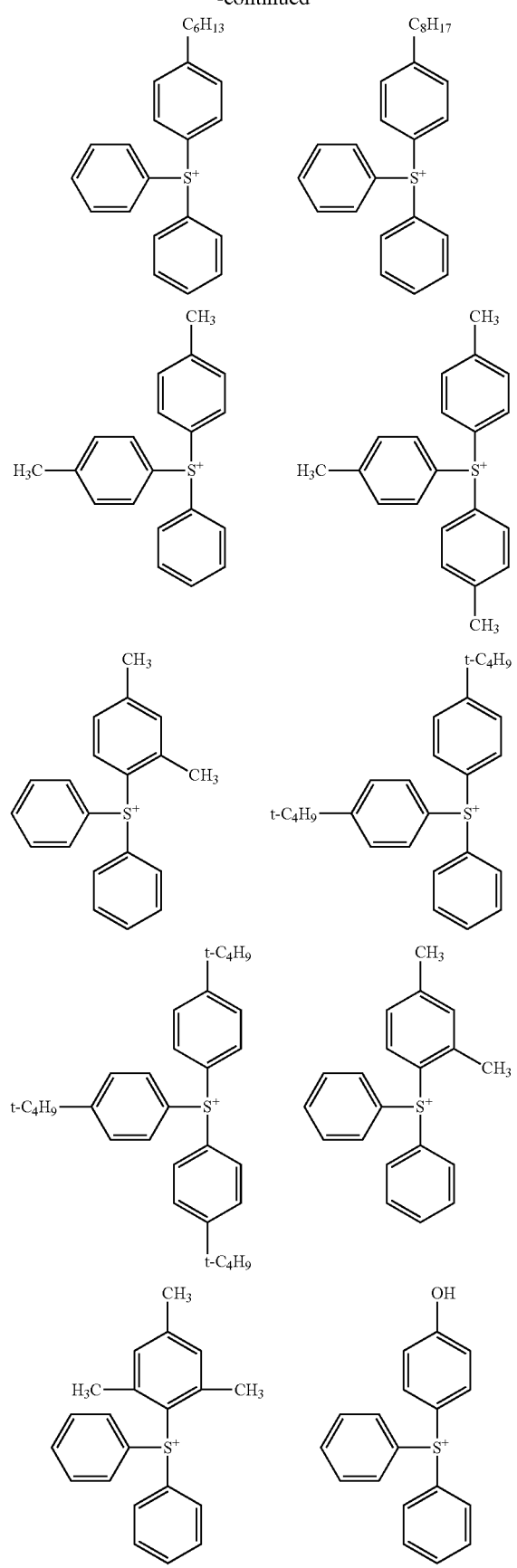
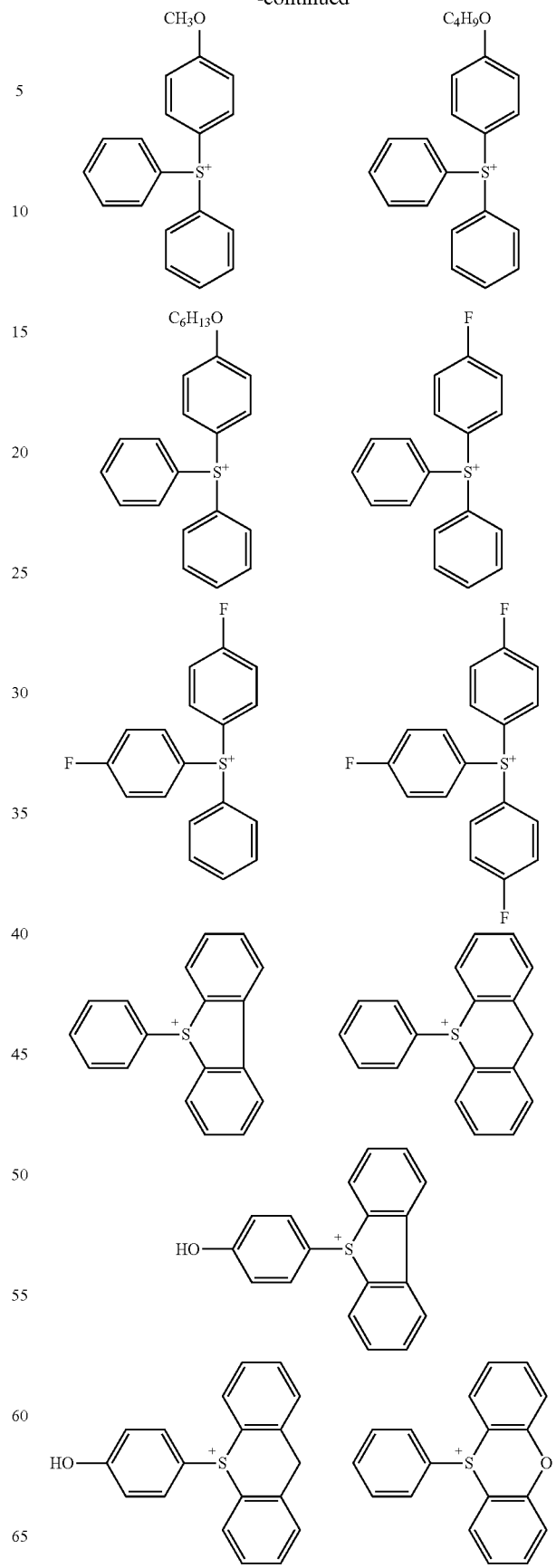

-continued
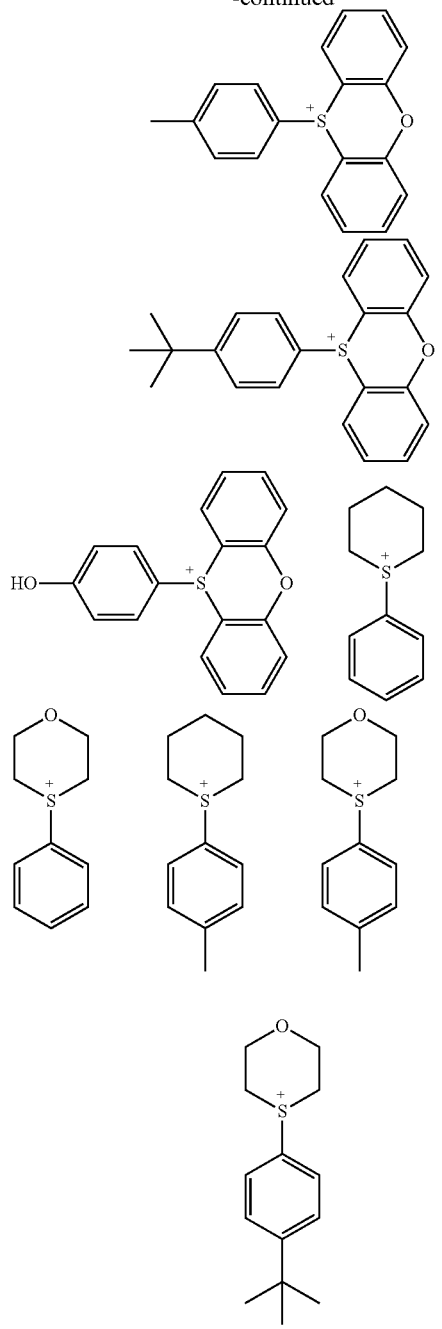
Examples of the cation represented by the formula (b2-2) include the followings.
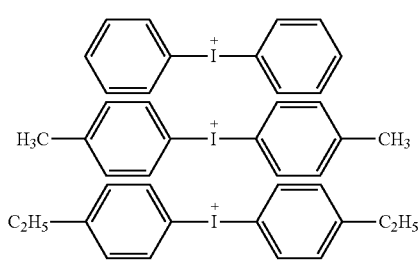
-continued
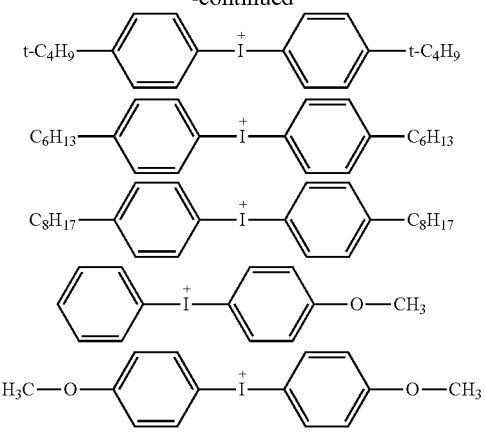
Examples of the cation represented by the formula (b2-3) include the followings.
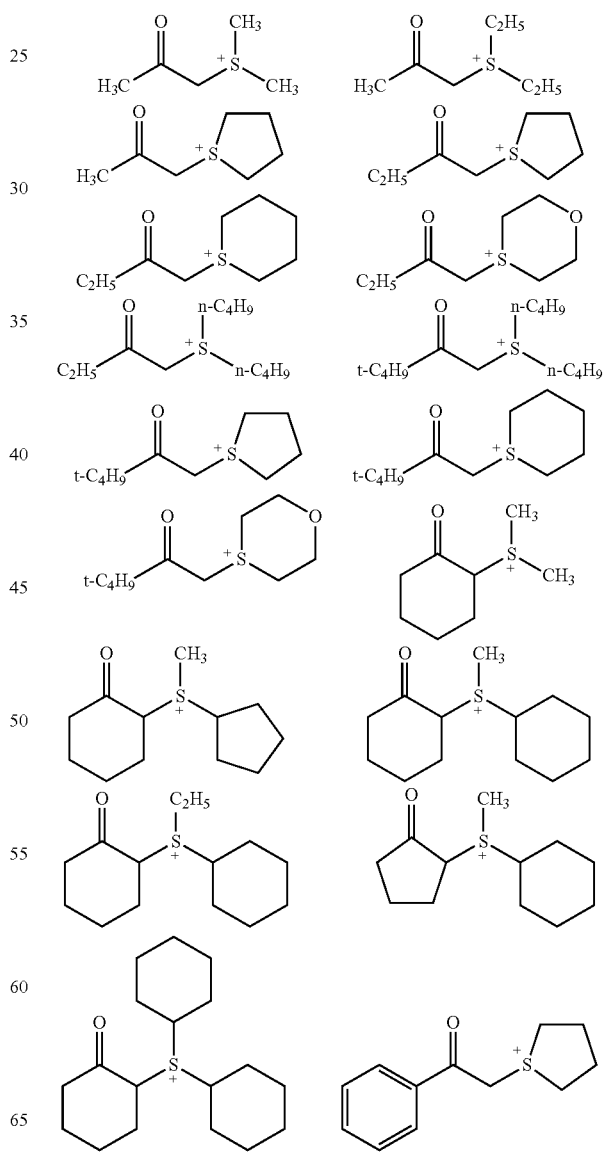

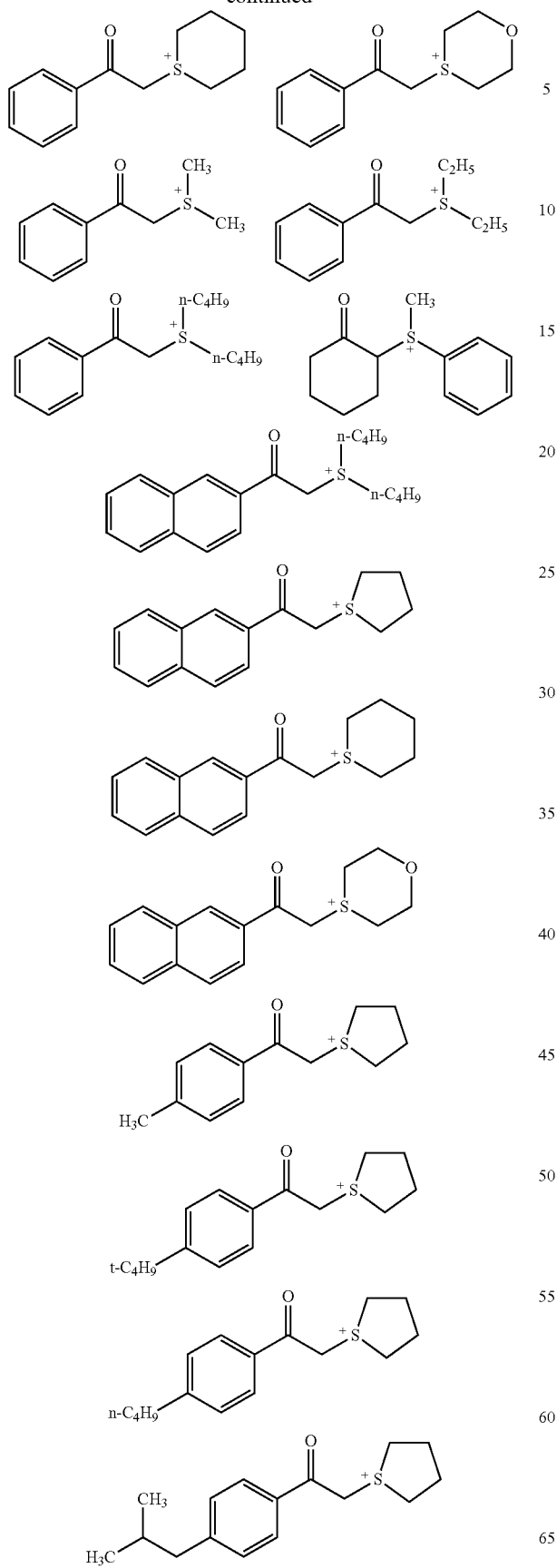
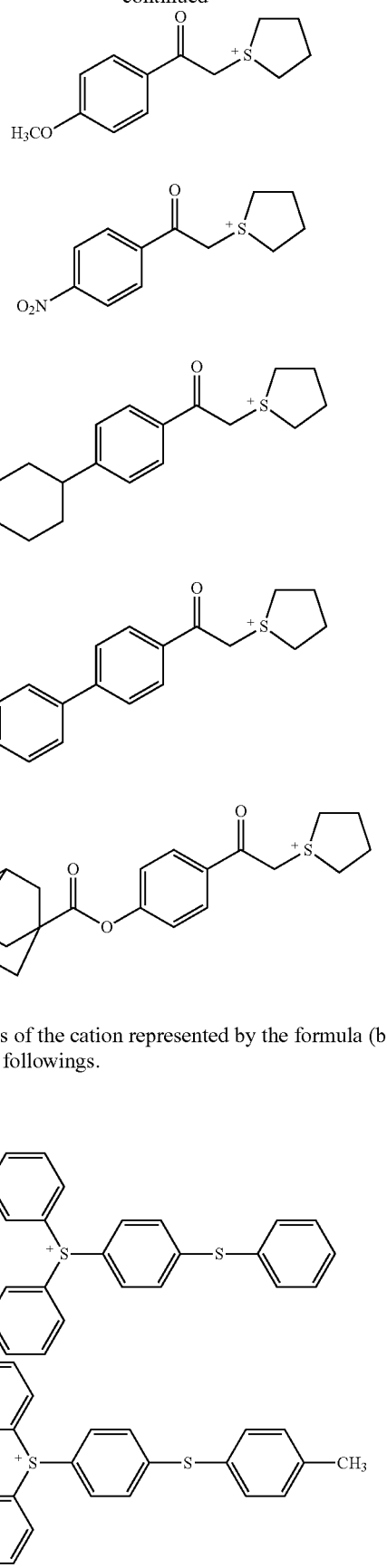
Examples of the cation represented by the formula (b2-4) include the followings.

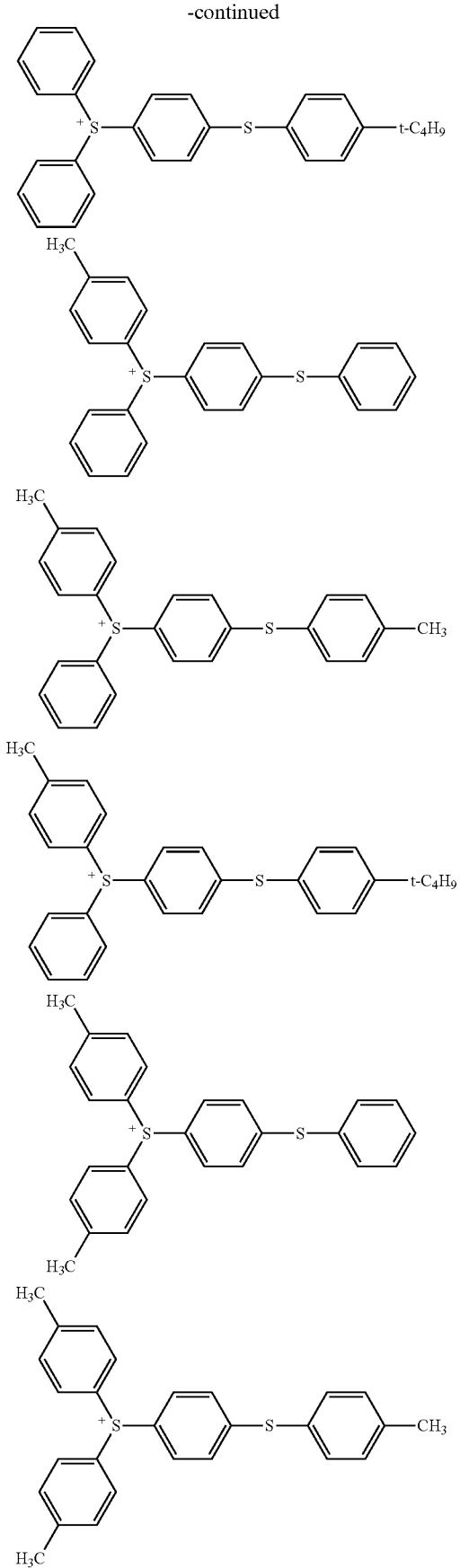
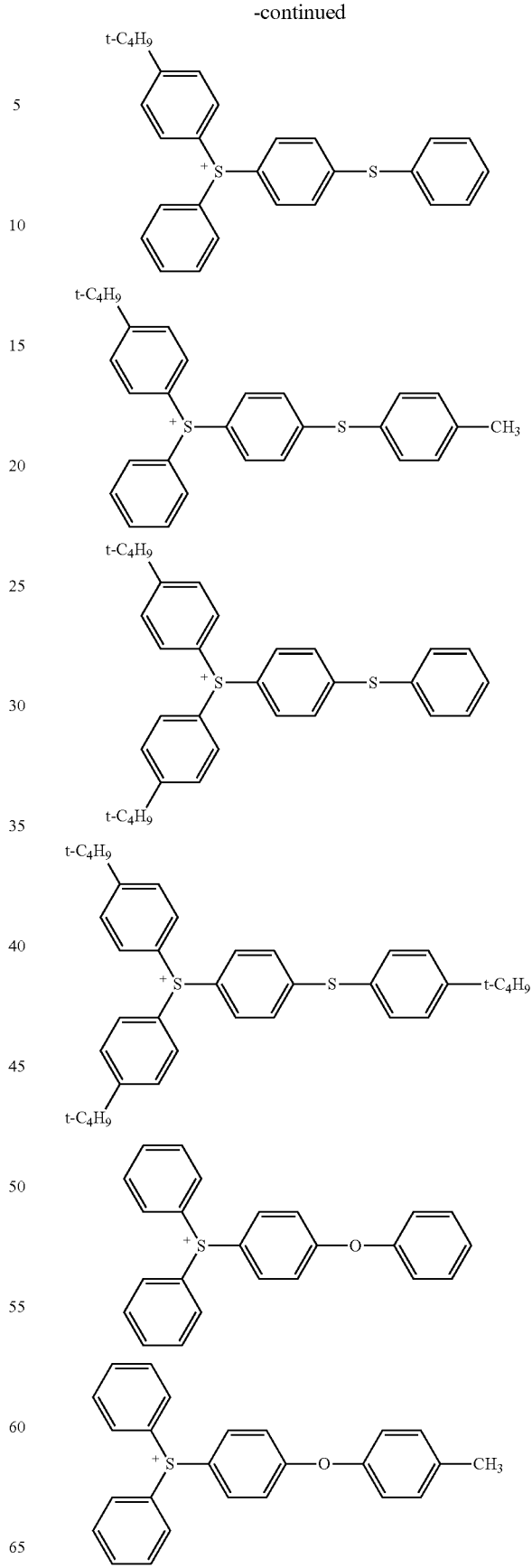

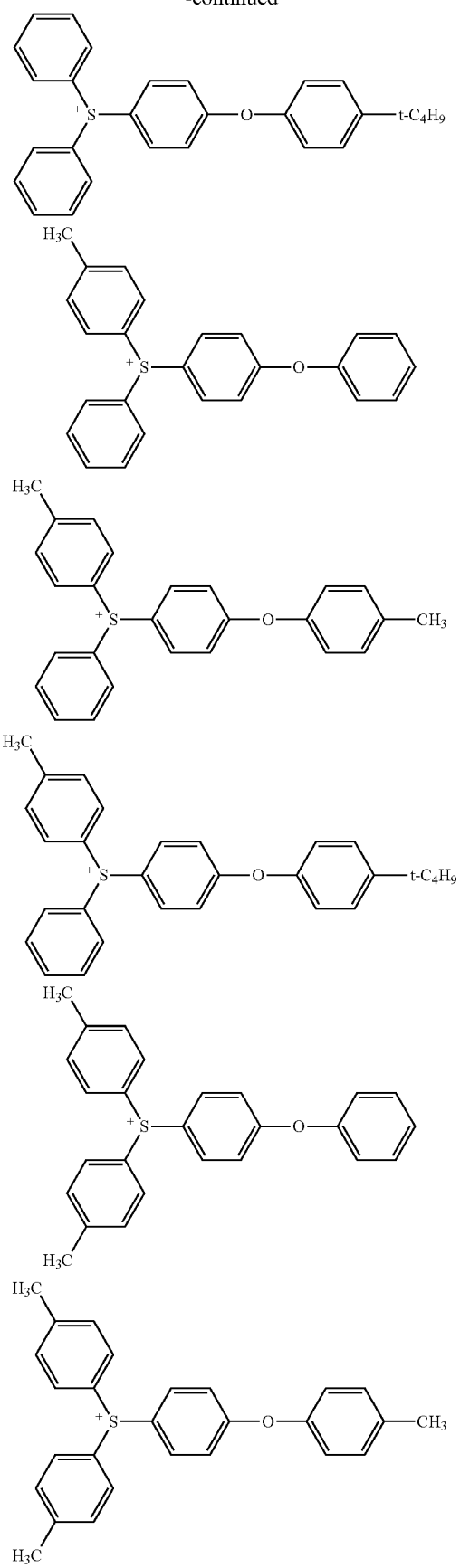

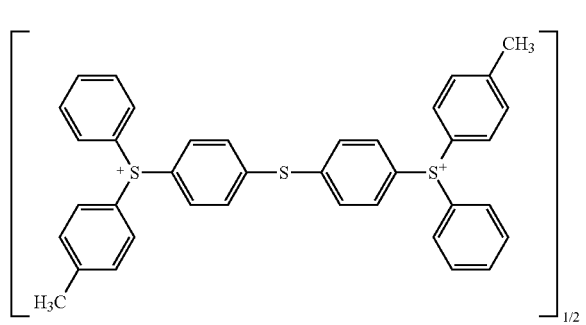
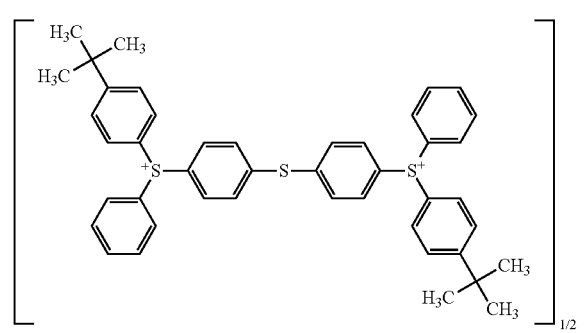
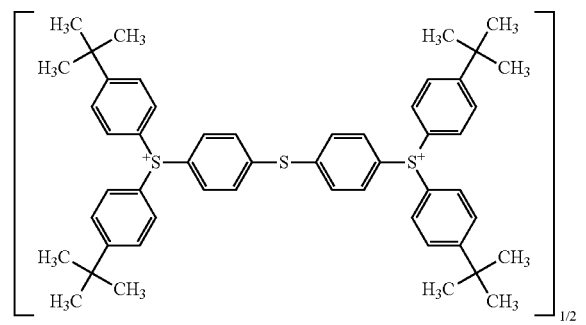
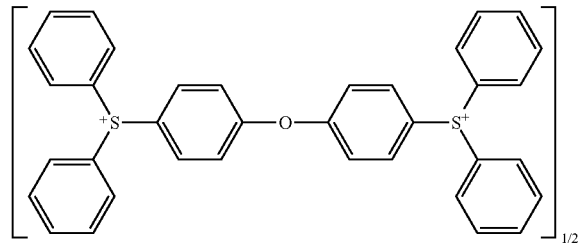
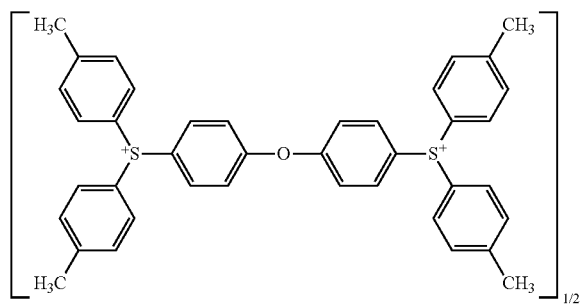
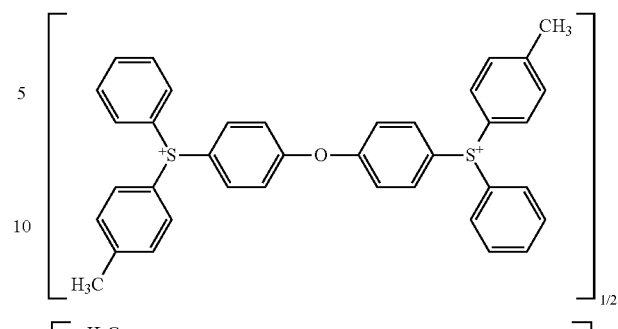
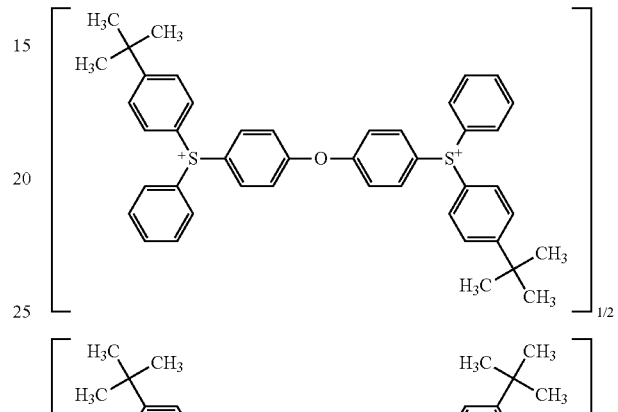
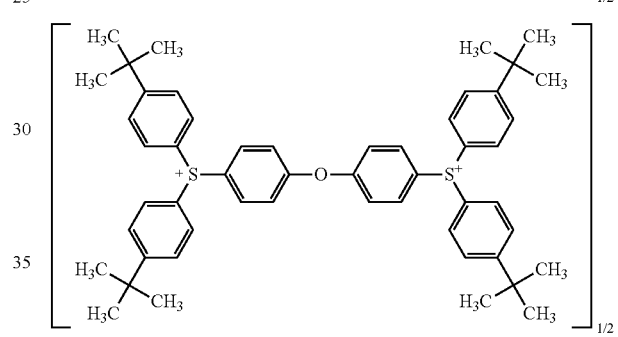
Examples of SALT (I) include a salt wherein the anion is any one of the above-mentioned anions and the cation is any one of organic cations. Preferable examples of SALT (I) include the following.
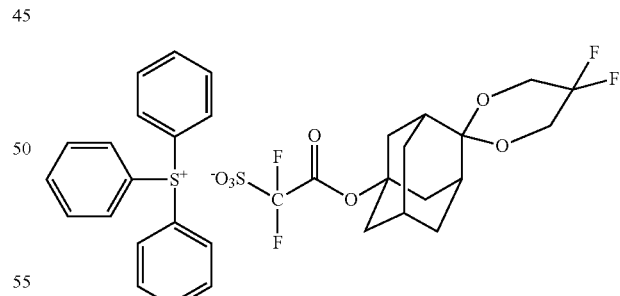
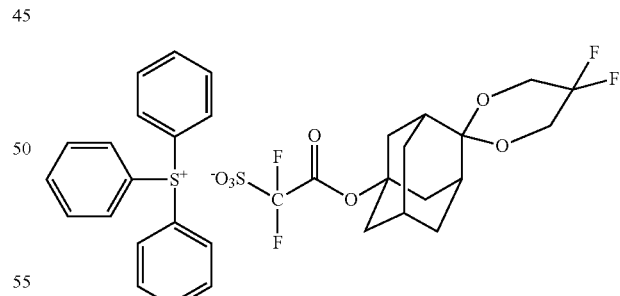
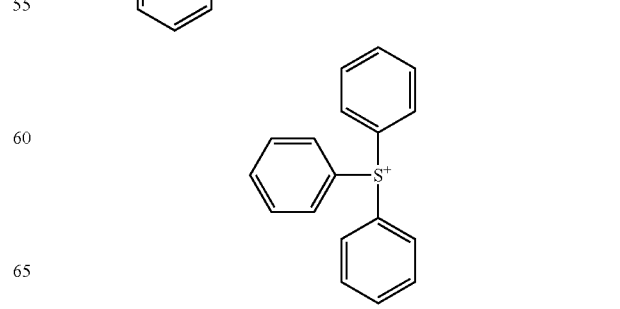

-continued
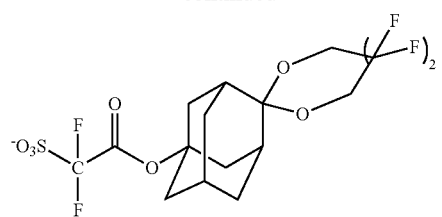
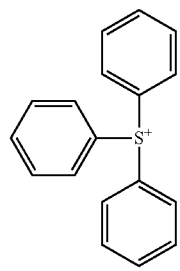
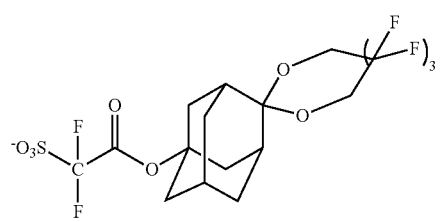
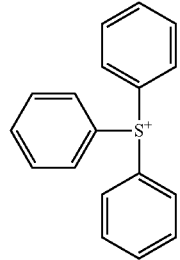
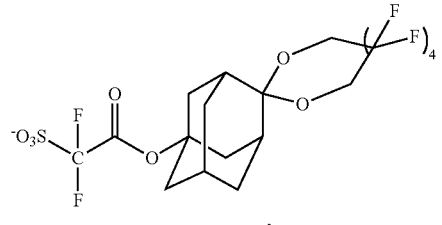
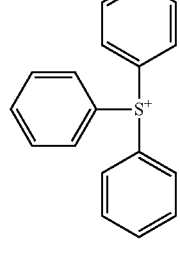
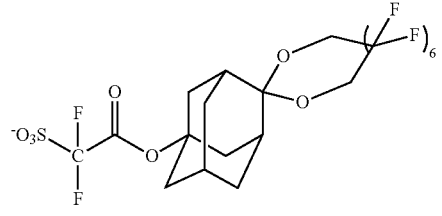
-continued
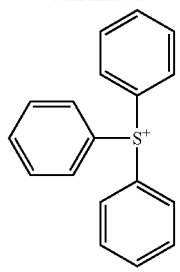
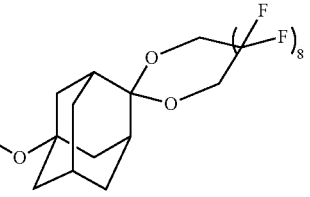
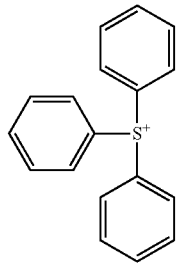
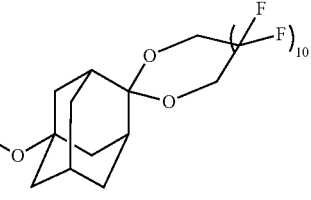
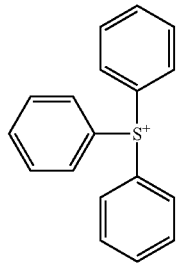
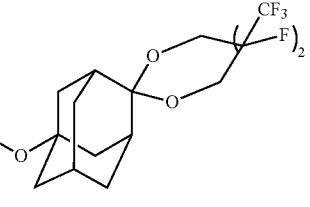
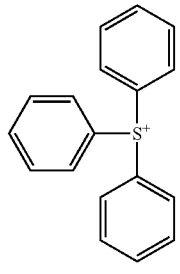

-continued
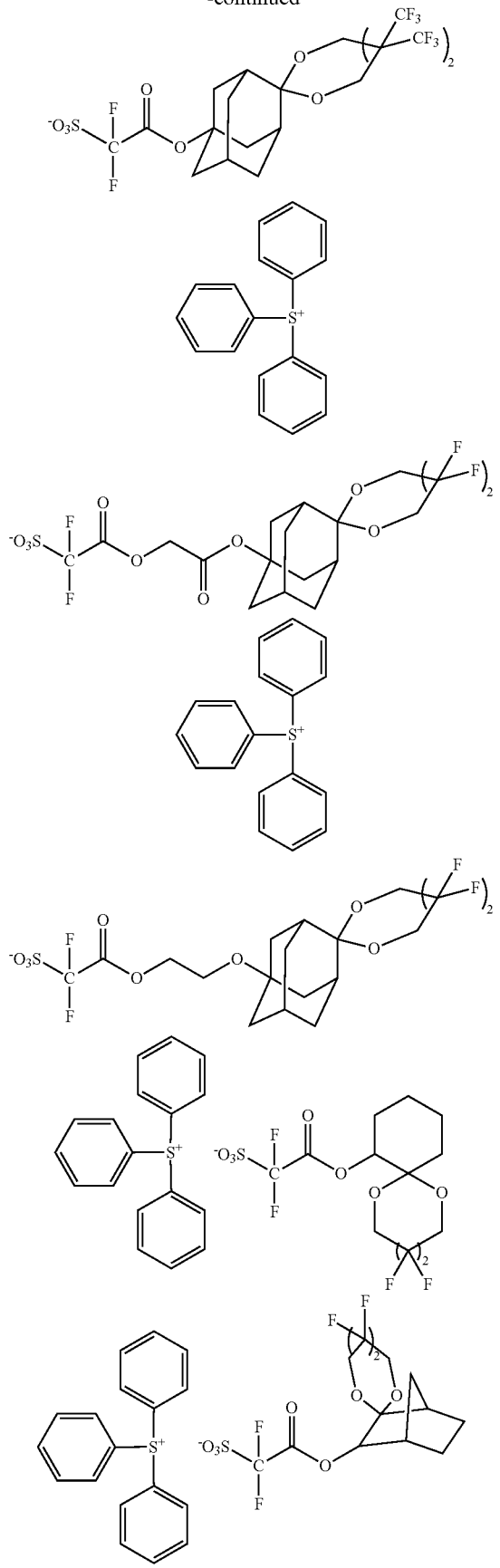
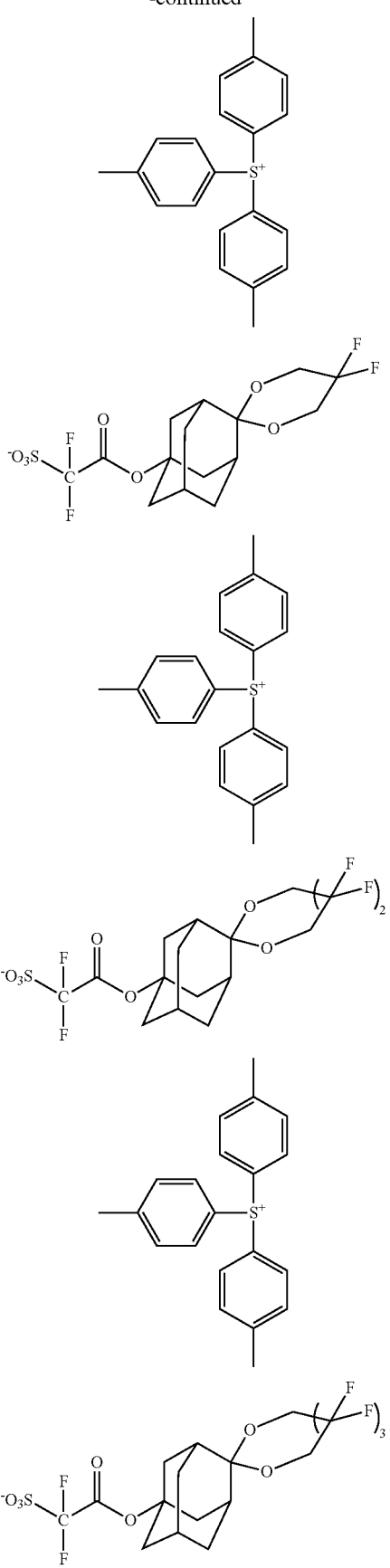

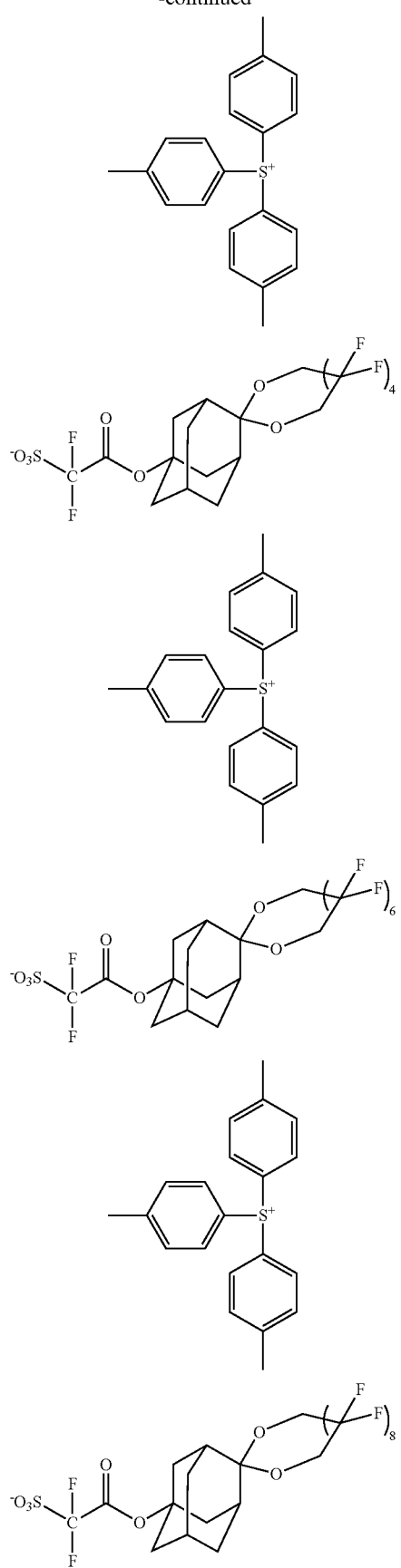

31
-continued
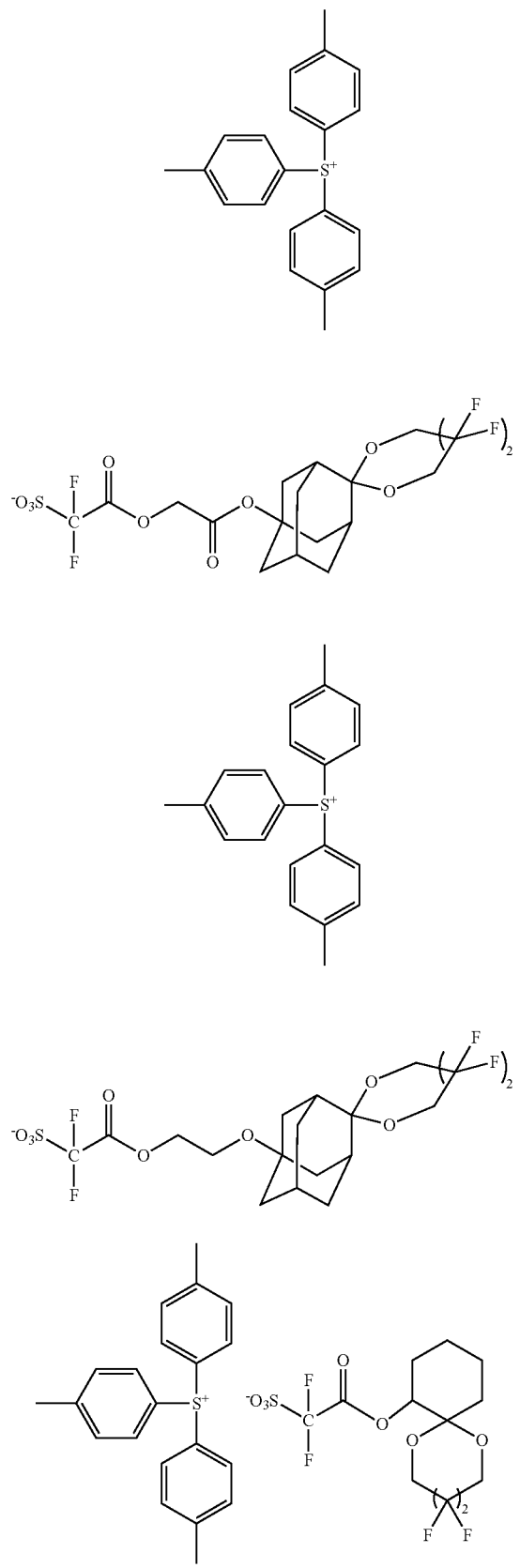
32
-continued
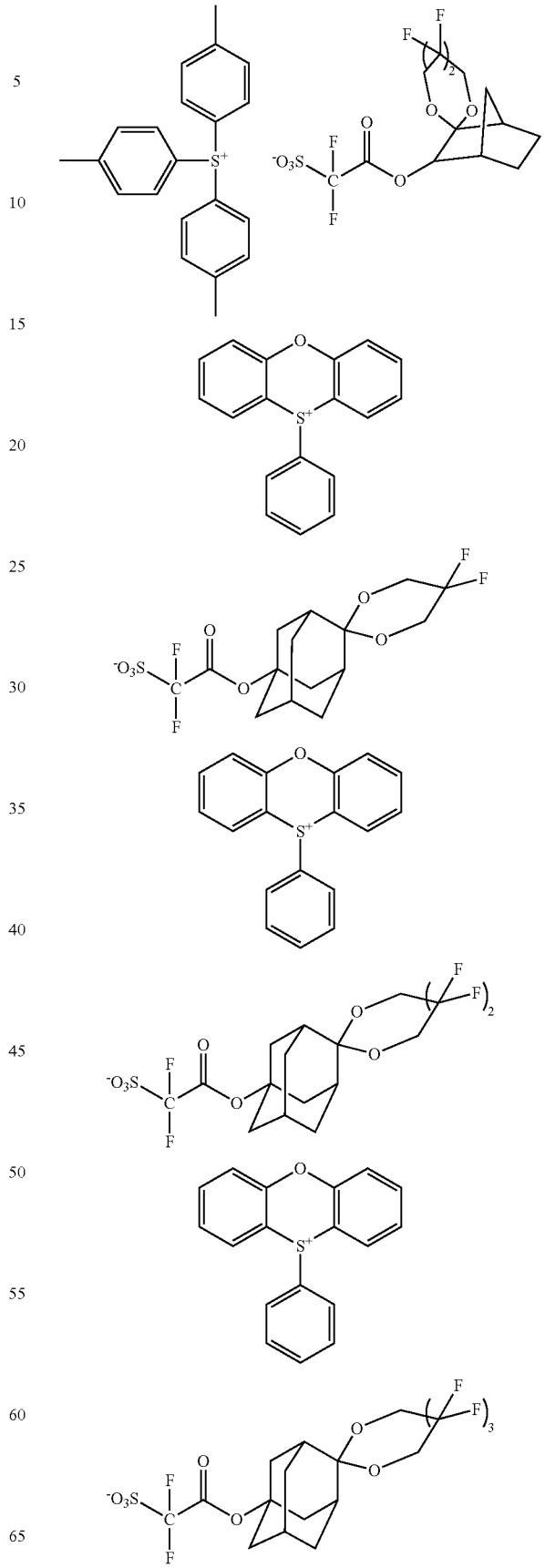

33
-continued
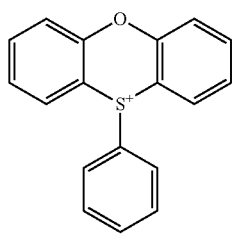
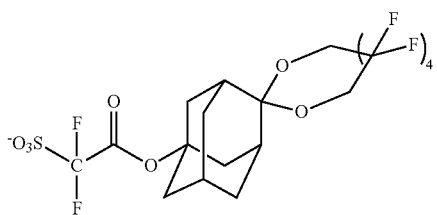
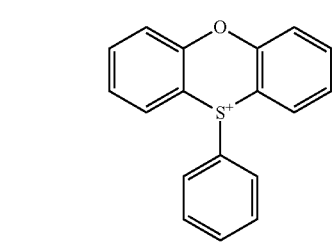
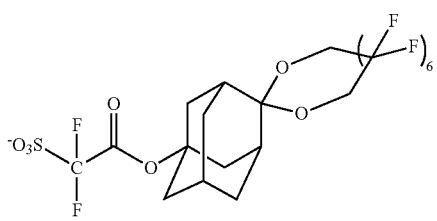
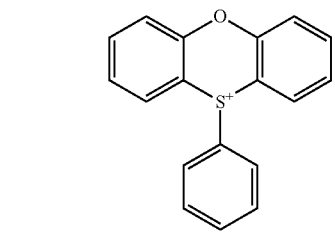
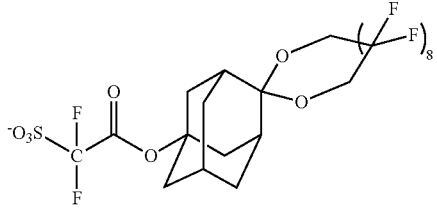
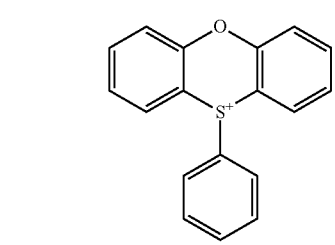
34
-continued
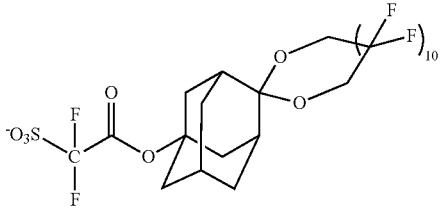
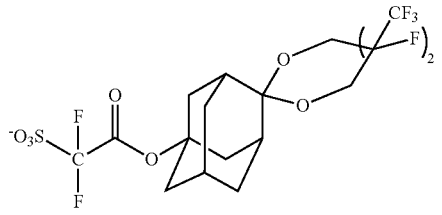
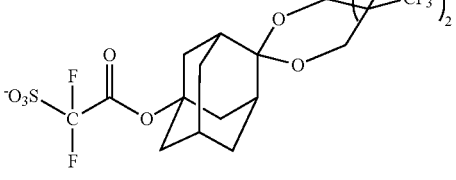
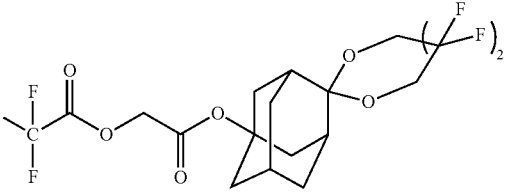

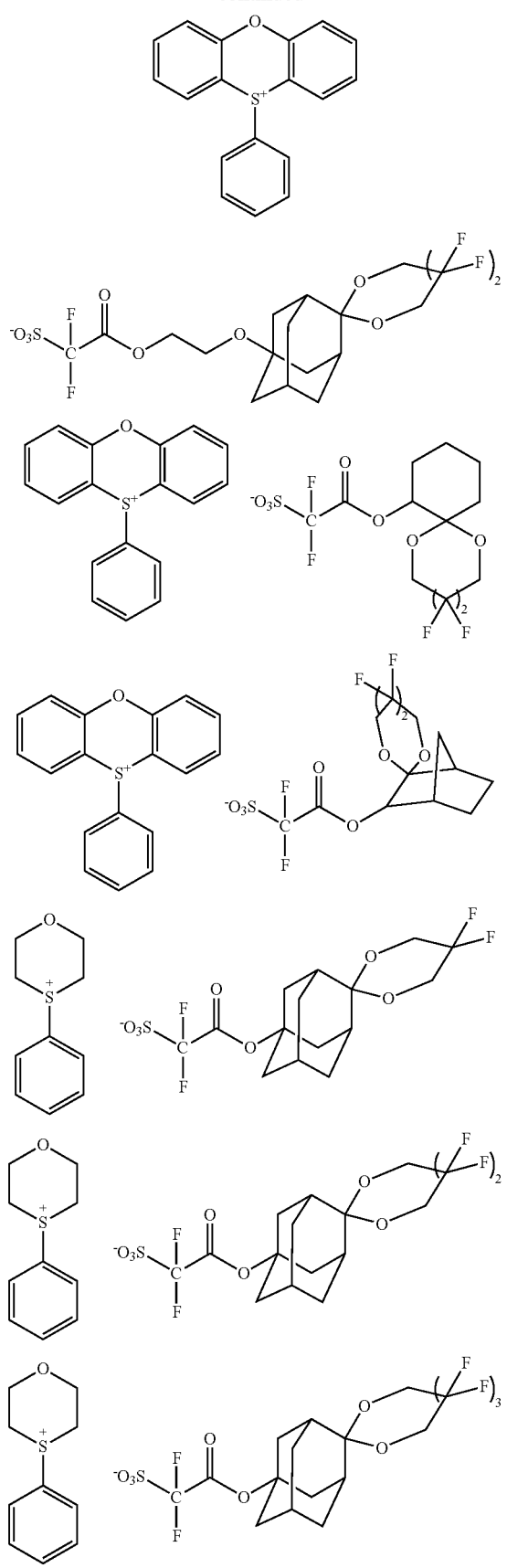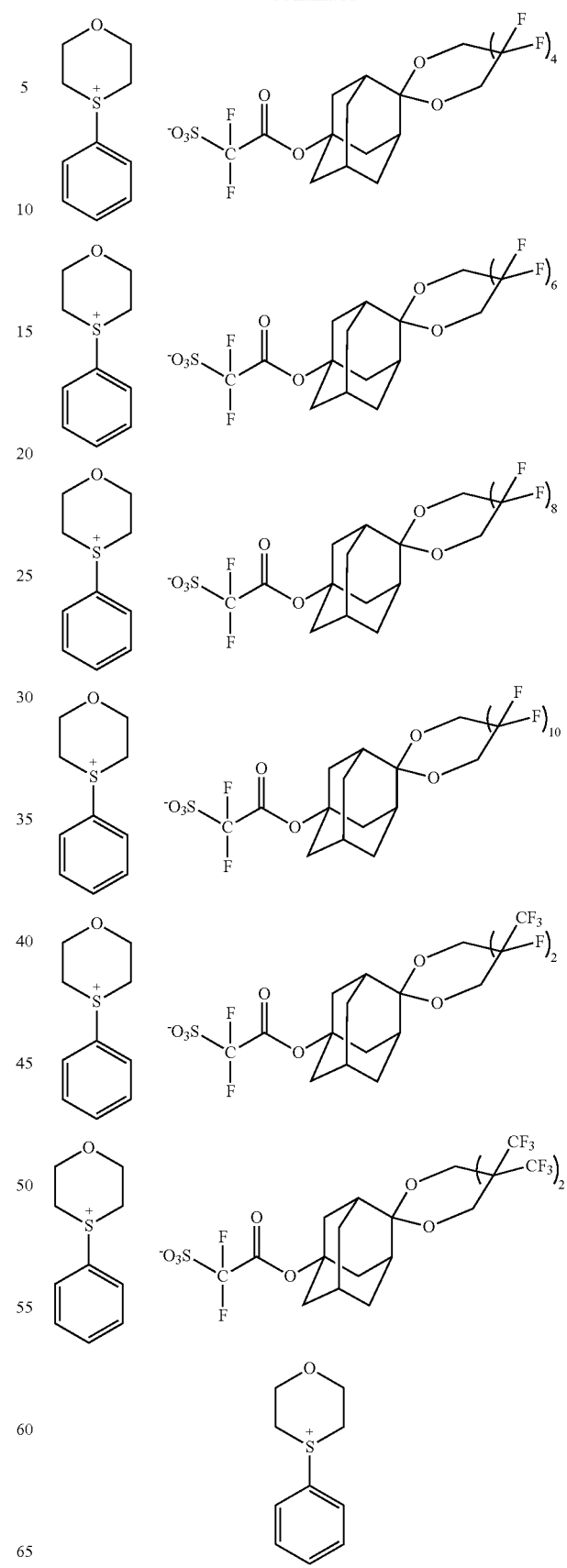

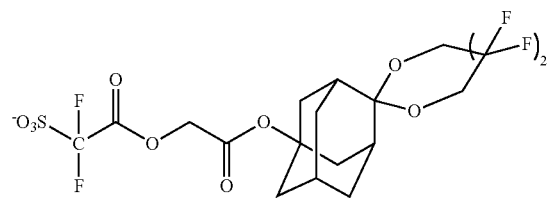
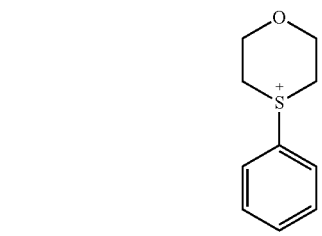
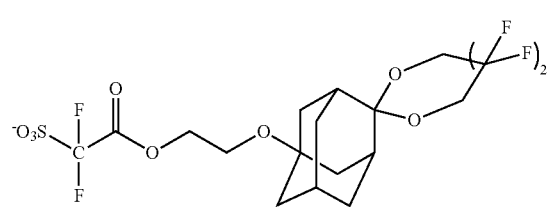
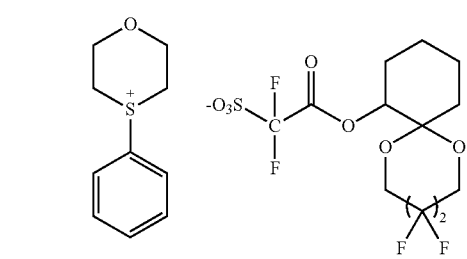
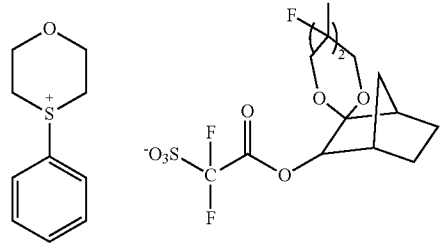
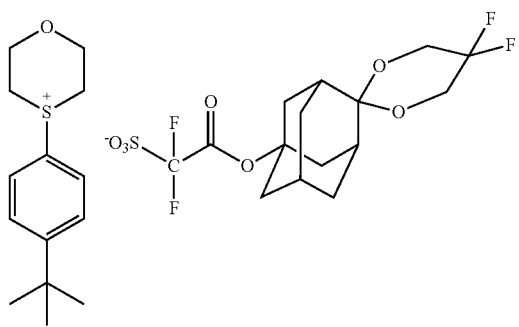
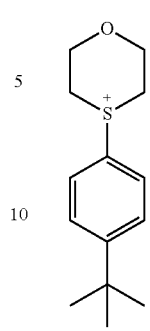
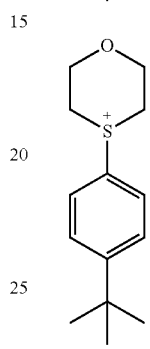
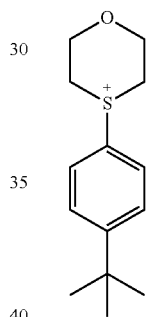
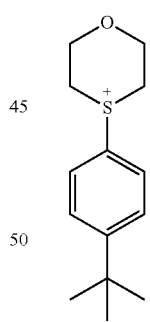
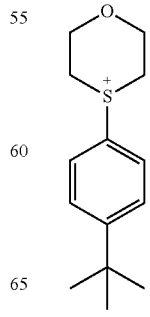

39
-continued
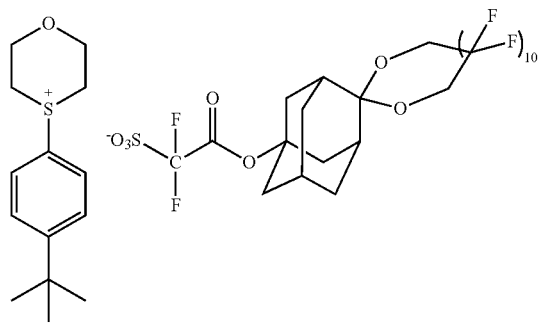
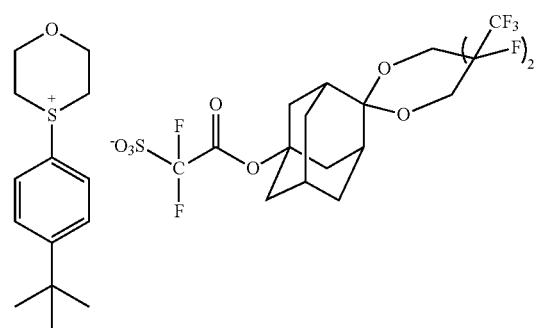
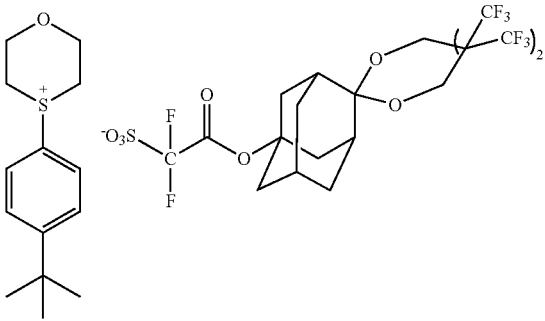
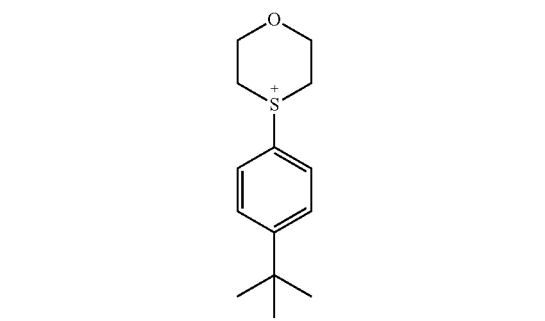
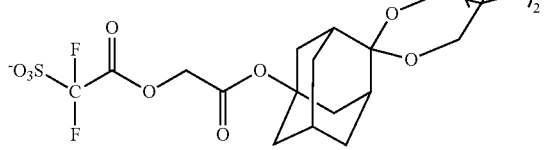
40
-continued
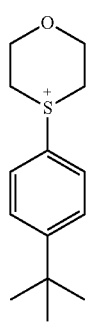
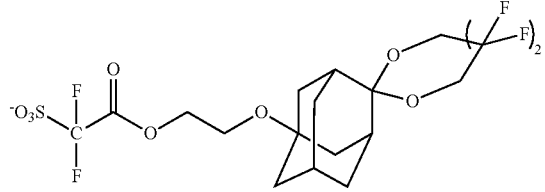
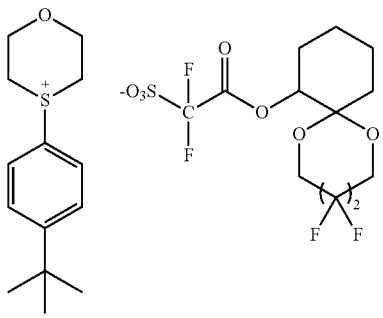
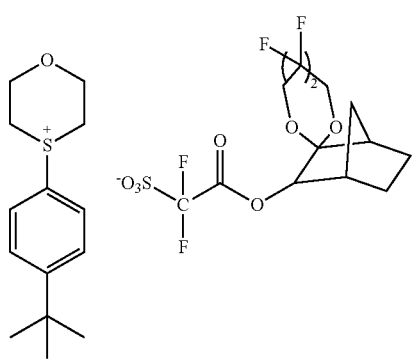
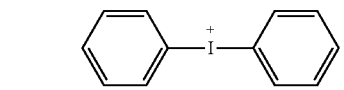
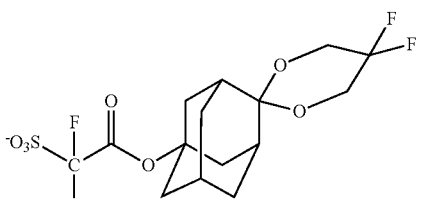
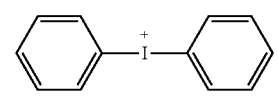

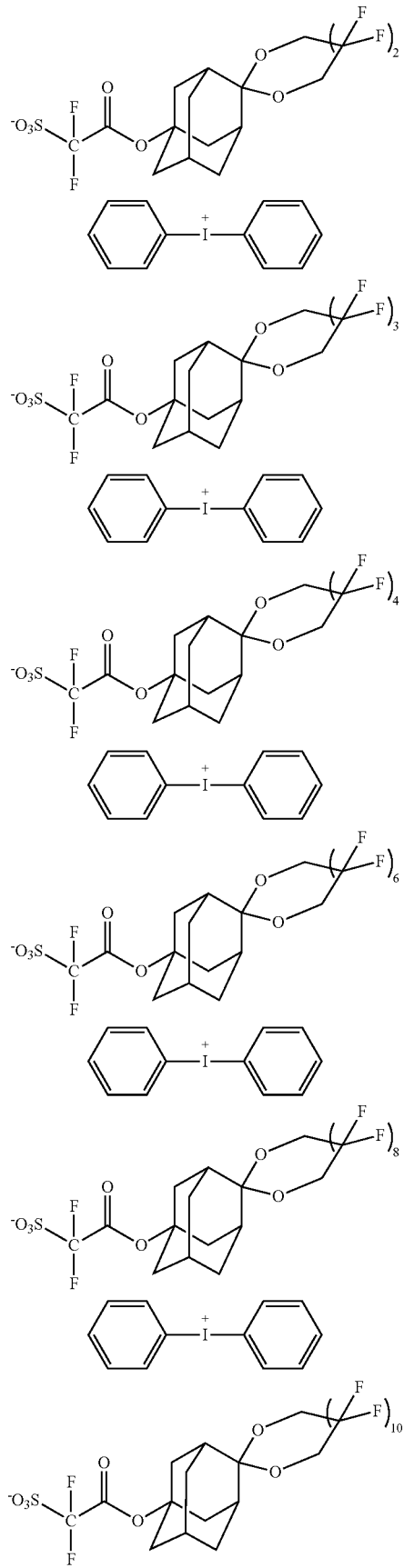
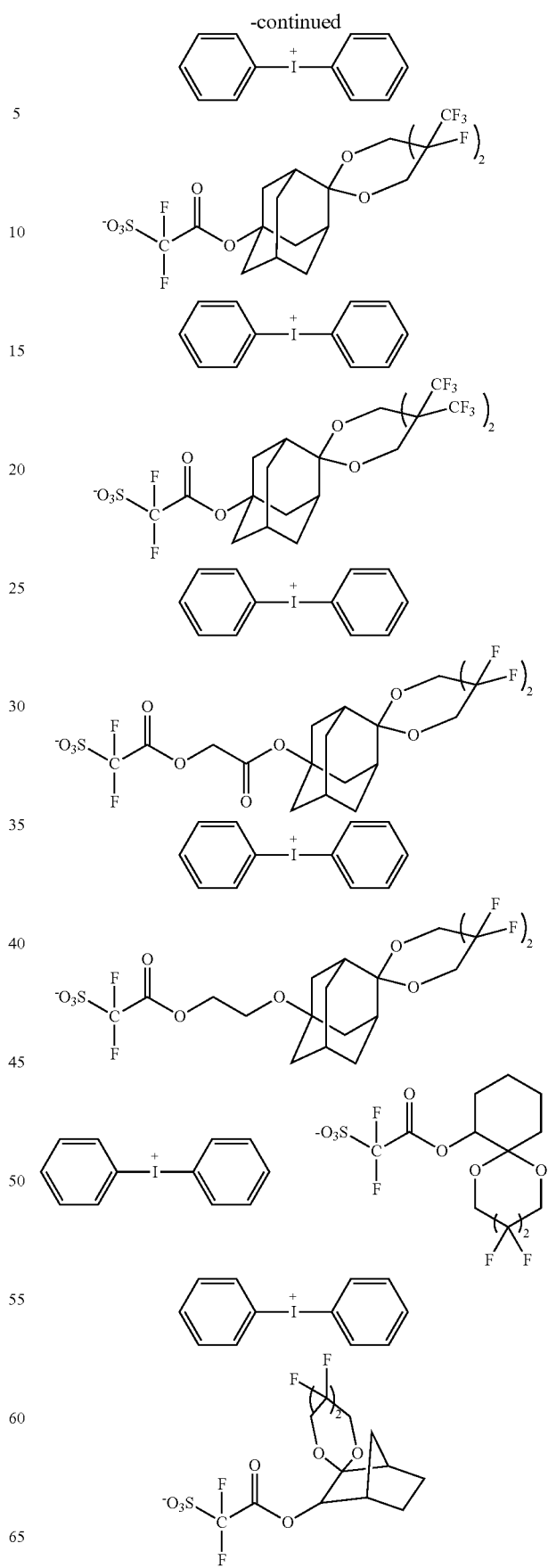

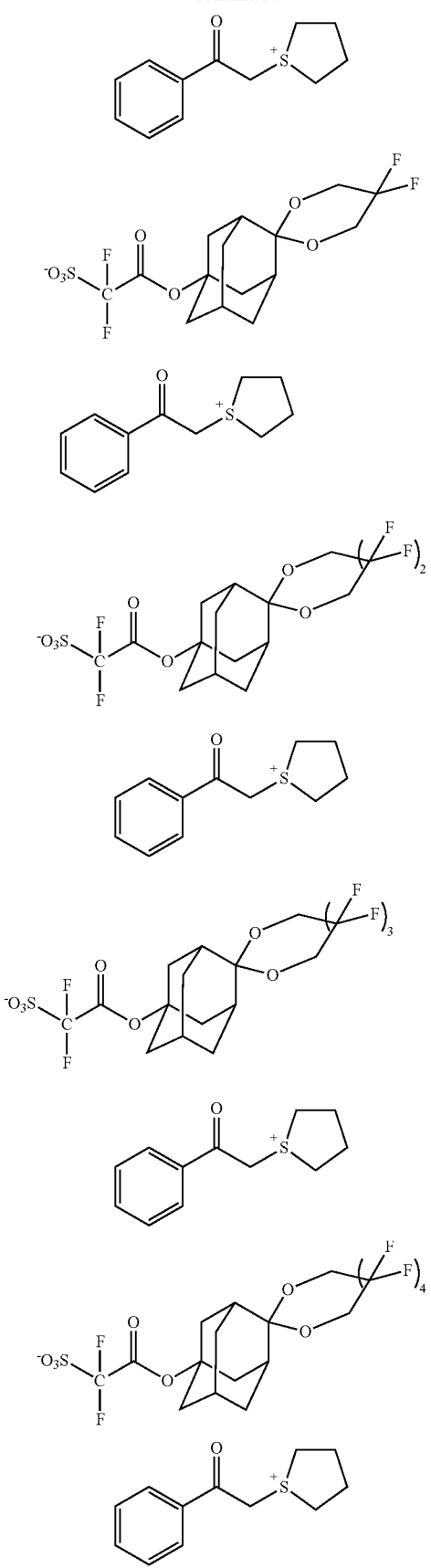
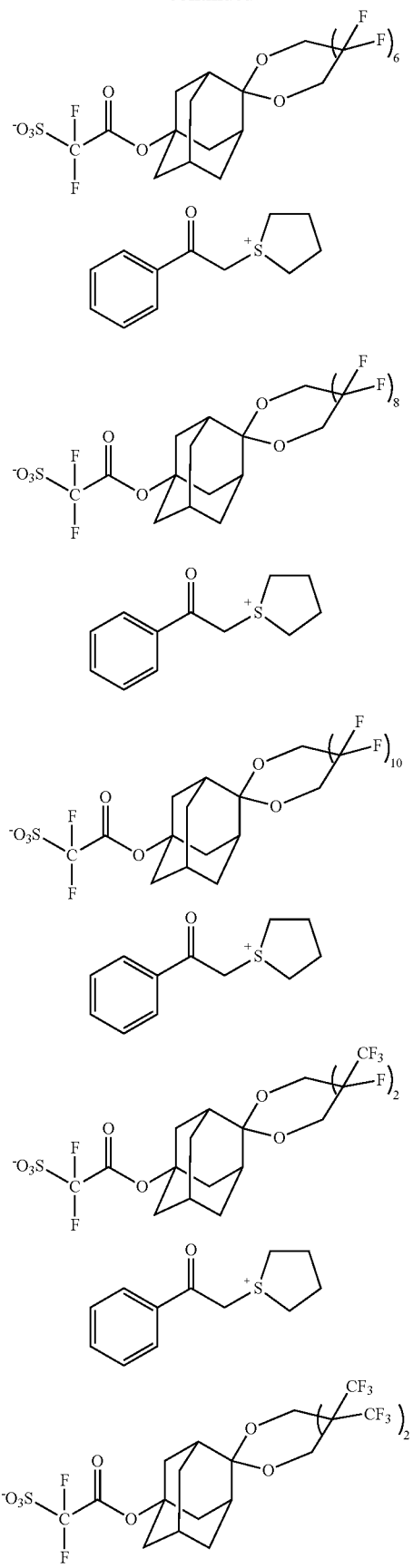

-continued

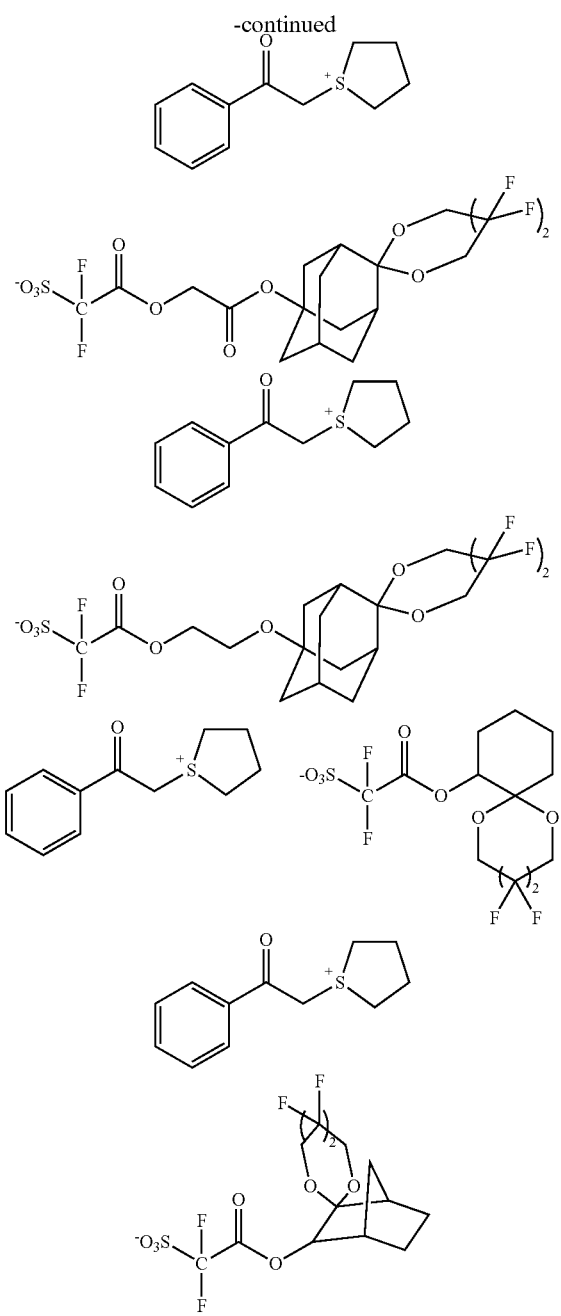

The process for producing SALT (I) will be illustrated. For example, a salt represented by the formula (b1):

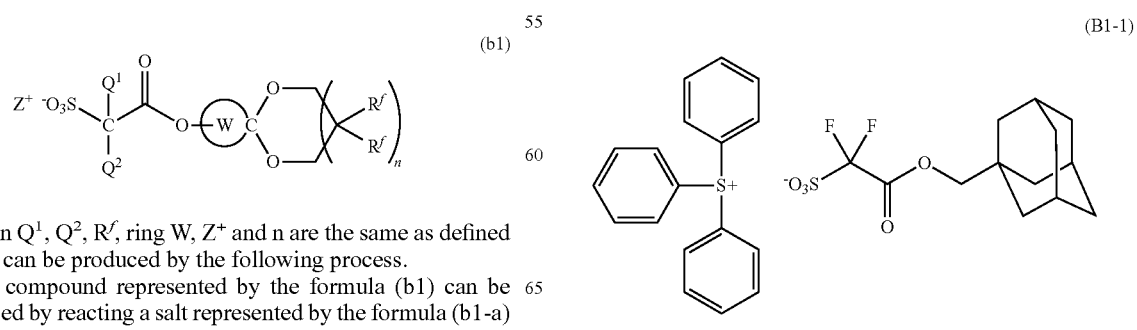

wherein $Q^1$, $Q^2$, $R^f$, ring W, $Z^+$ and n are the same as defined above, can be produced by the following process.

The compound represented by the formula (b1) can be produced by reacting a salt represented by the formula (b1-a) with a compound represented by the formula (b1-b) in a solvent such as 1,2-dichloroethane in the presence of an acidic catalyst such as p-toluenesulfonic acid.

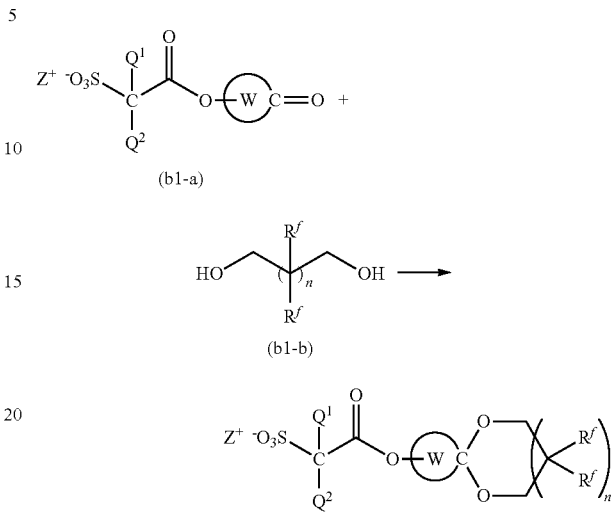

wherein $Q^1$, $Q^2$, $R^f$, ring W, $Z^+$ and n are the same as defined above.

The salt represented by the formula (b1-a) can be produced, for example, according to the method described in JP 2007-224005 A. Examples of the compound represented by the formula (b1-b) include 2,2,3,3-tetrafluoro-1,4-butanediol.

Next, the acid generator of the present invention will be illustrated.

The acid generator of the present invention comprises SALT (I). The acid generator of the present invention can contain two or more kinds of SALT (I). The acid generator of the present invention may consist of SALT (I). The acid generator of the present invention can contain one or more known acid generators other than SALT (I) in addition to SALT (I). The acid generator of the present invention contains SALT (I) in an effective amount.

Preferable examples of the acid generator other than SALT (I) include salts represented by the formulae (B1-1) to (B1-17), the salt containing a triphenylsulfonium cation or a tritolylsulfonium cation is more preferable, and the salts represented by the formulae (B1-1), (B1-2), (B1-3), (B1-6), (B1-11), (B1-12), (B1-13) and (B1-14) are especially preferable.

(B1-1)

-continued
(B1-2)
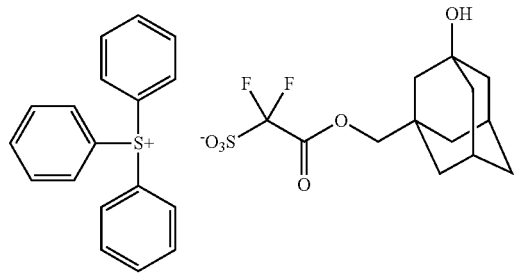
(B1-3)
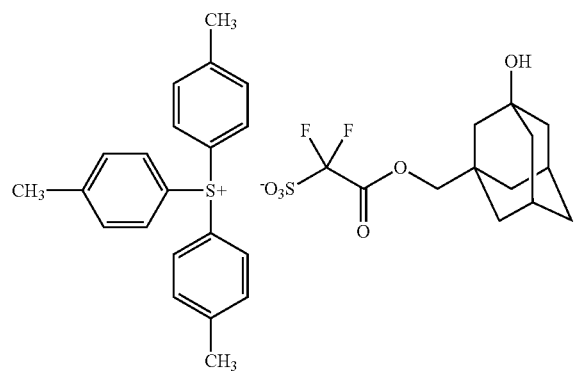
(B1-4)
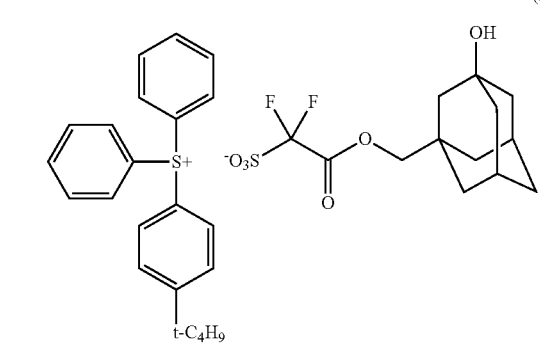
(B1-5)
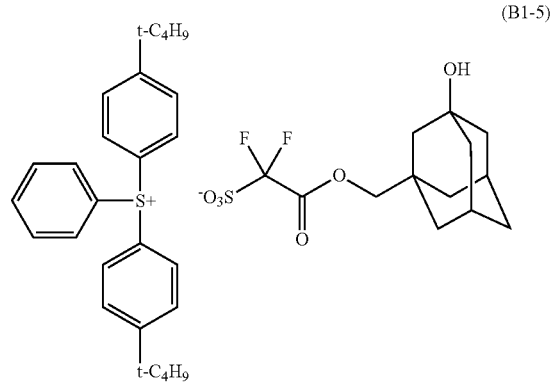
-continued
(B1-6)
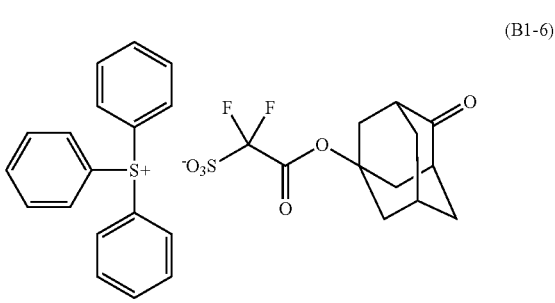
(B1-7)
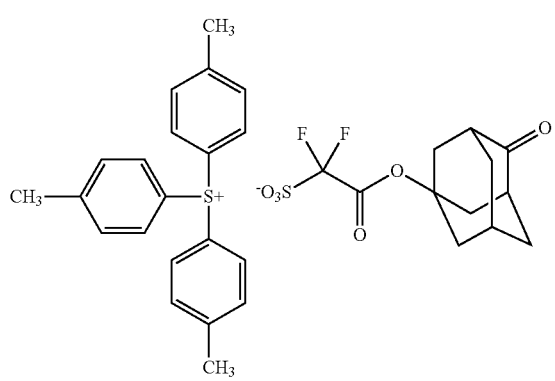
(B1-8)
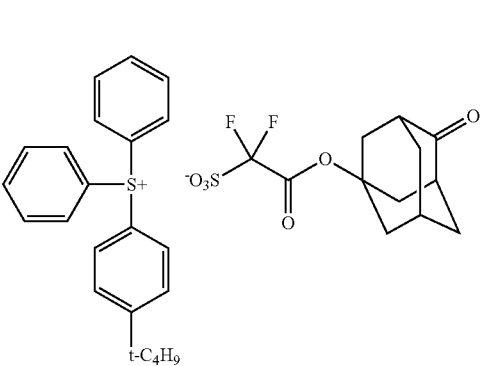
(B1-9)
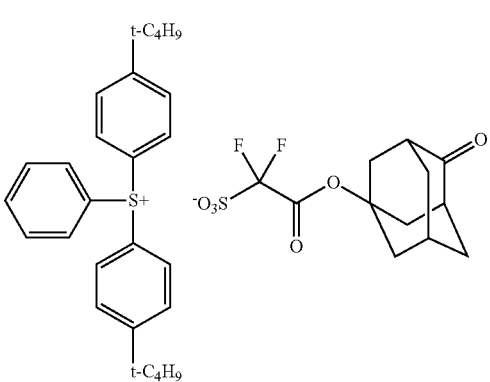

(B1-10)
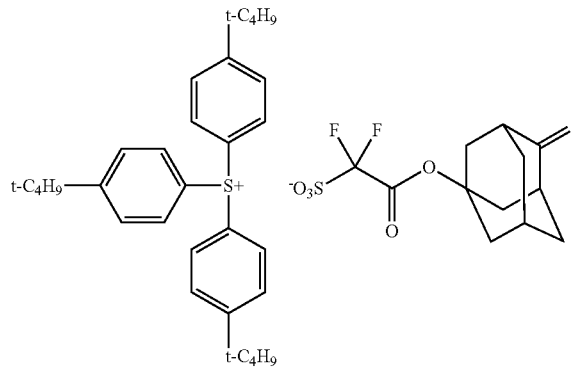

(B1-11)
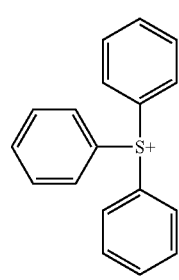

(B1-12)
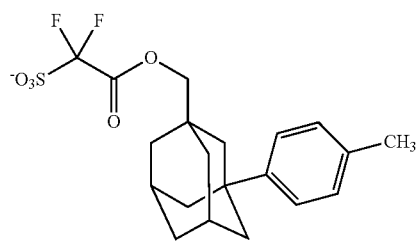

(B1-13)
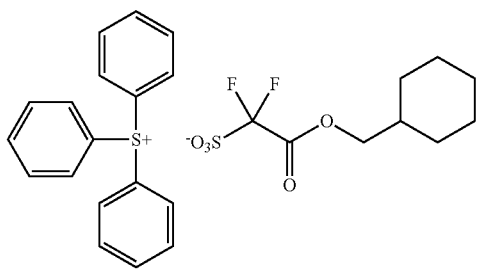

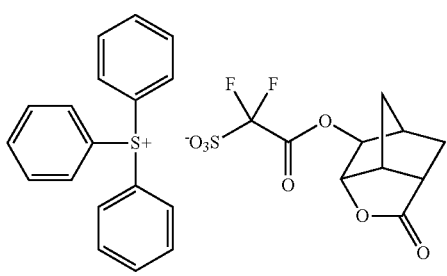

(B1-14)
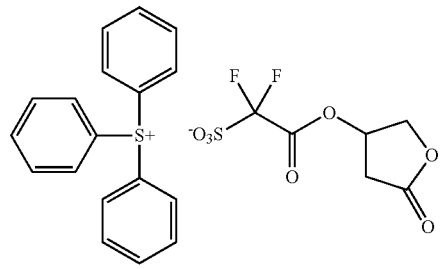

(B1-15)
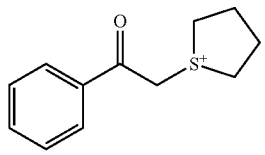

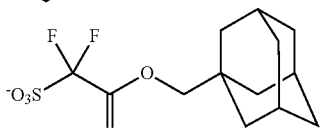

(B1-16)
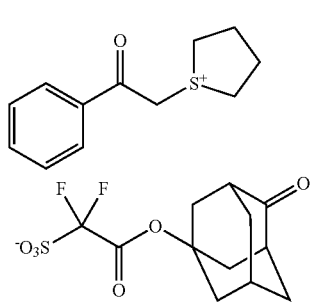

(B1-17)
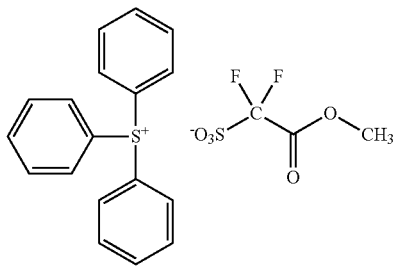

When the acid generator of the present invention contains SALT (I) and the acid generator other than SALT (I), the content of SALT (I) is preferably 10 parts by weight or more and more preferably 30 parts by Weight or more per 100 parts by weight of the acid generator of the present invention, and the content of SALT (I) is preferably 90 parts by weight or less and more preferably 70 parts by weight or less per 100 parts by weight of the acid generator of the present invention.

Next, the photoresist composition of the present invention will be illustrated.

The photoresist composition of the present invention comprises the acid generator of the present invention and a resin having an acid-labile group, being insoluble or poorly soluble in an aqueous alkali solution but becoming soluble in an aqueous alkali solution by the action of an acid.

The resin is insoluble or poorly soluble in an alkali aqueous solution but becomes soluble in an alkali aqueous solution by the action of an acid. The resin has one or more acid-labile groups. In this specification, "an acid-labile group" means a group capable of being eliminated by the action of an acid.

Examples of the acid-labile group include a group represented by the formula (1):

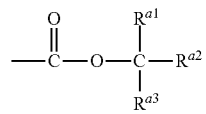

(1)

wherein $R^{a1}$, $R^{a2}$ and $R^{a3}$ independently each represent a C1-C8 aliphatic hydrocarbon group or a C3-C20 alicyclic hydrocarbon group, and $R^{a1}$ and $R^{a2}$ can be bonded each other to form a C3-C20 ring together with a carbon atom to which $R^{a1}$ and $R^{a2}$ are bonded, and one or more —CH$_2$— in the aliphatic hydrocarbon group, the alicyclic hydrocarbon group and the ring can be replaced by —O—, —S— or —CO—.

Examples of the aliphatic hydrocarbon group include a C1-C8 alkyl group. Specific examples of the C1-C8 alkyl group include a methyl group, an ethyl group, a propyl group, an isopropyl group, a butyl group, a pentyl group, a hexyl group, a heptyl group and an octyl group. The alicyclic hydrocarbon group may be monocyclic or polycyclic. Examples of the alicyclic hydrocarbon group include a monocyclic alicyclic hydrocarbon group such as a C3-C20 cycloalkyl group (e.g. a cyclopentyl group, a cyclohexyl group, a methylcyclohexyl group, a dimethylcyclohexyl group, a cycloheptyl group and a cyclooctyl group) and a polycyclic alicyclic hydrocarbon group such as a decahydronaphthyl group, an adamantyl group, a norbornyl group, a methylnorbornyl group, and the followings:

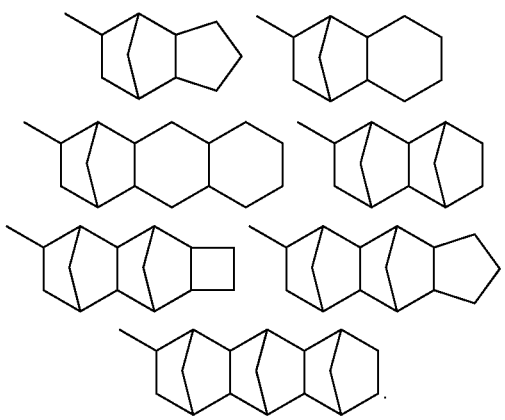

The alicyclic hydrocarbon group preferably has 3 to 16 carbon atoms.

Examples of the ring formed by bonding $R^{a1}$ and $R^{a2}$ each other include the following groups and the ring preferably has 3 to 12 carbon atoms.

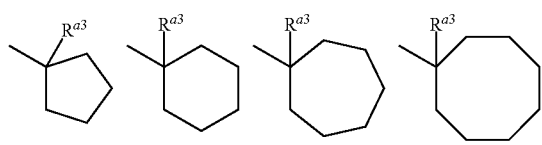

-continued

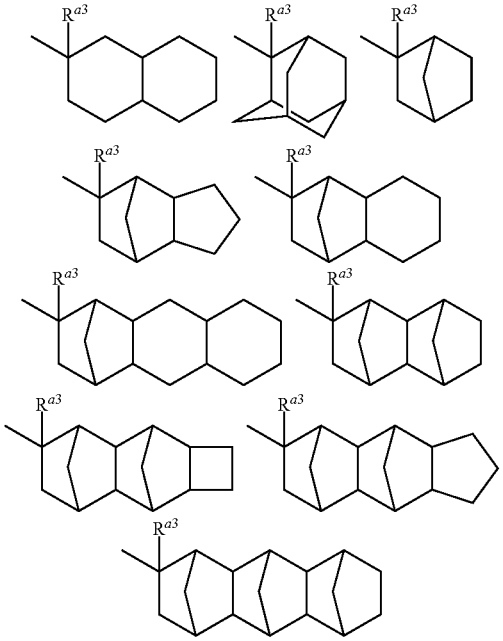

wherein $R^{a1}$ is the same as defined above.

The group represented by the formula (I) wherein $R^{a1}$, $R^{a2}$ and $R^{a3}$ independently each represent a C1-C8 alkyl group such as tert-butyl group, the group represented by the formula (I) wherein $R^{a1}$ and $R^{a2}$ are bonded each other to form an adamantyl ring and $R^{a3}$ is a C1-C8 alkyl group such as a 2-alkyl-2-adamantyl group, and the group represented by the formula (I) wherein $R^{a1}$ and $R^{a2}$ are C1-C8 alkyl groups and $R^{a3}$ is an adamantyl group such as a 1-(1-adamantyl)-1-alkylalkoxycarbonyl group are preferable.

Examples of the acid-labile group include a group represented by the formula (20):

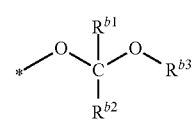

(20)

wherein $R^{b1}$ and $R^{b2}$ independently each represent a hydrogen atom or a C1-C12 hydrocarbon group, and $R^{b3}$ represents a C1-C20 hydrocarbon group, and $R^{b2}$ and $R^{b3}$ can be bonded each other to form a C3-C20 ring together with the carbon atom and the oxygen atom to which they are bonded, and one or more —CH$_2$— in the hydrocarbon group and the ring can be replaced by —O—, —S— or —CO—.

The group represented by the formula (20) has an acetal structure.

Examples of the hydrocarbon group include an aliphatic hydrocarbon group, an alicyclic hydrocarbon group and an aromatic hydrocarbon group. Examples of the aliphatic hydrocarbon group and the alicyclic hydrocarbon group include the same as described above. Examples of the aromatic hydrocarbon group include an aryl group such as a phenyl group, a naphthyl group, a p-methylphenyl group, a p-tert-butylphenyl group, a p-adamantylphenyl group, a tolyl group, a xylyl group, a cumyl group, a mesityl group, a biphenyl group, an anthryl group, a phenanthryl group, a 2,6-diethylphenyl group and a 2-methyl-6-ethylphenyl group.

It is preferred that at least one of $R^{b1}$ and $R^{b2}$ is a hydrogen atom.

Examples of the group represented by the formula (20) include the following.

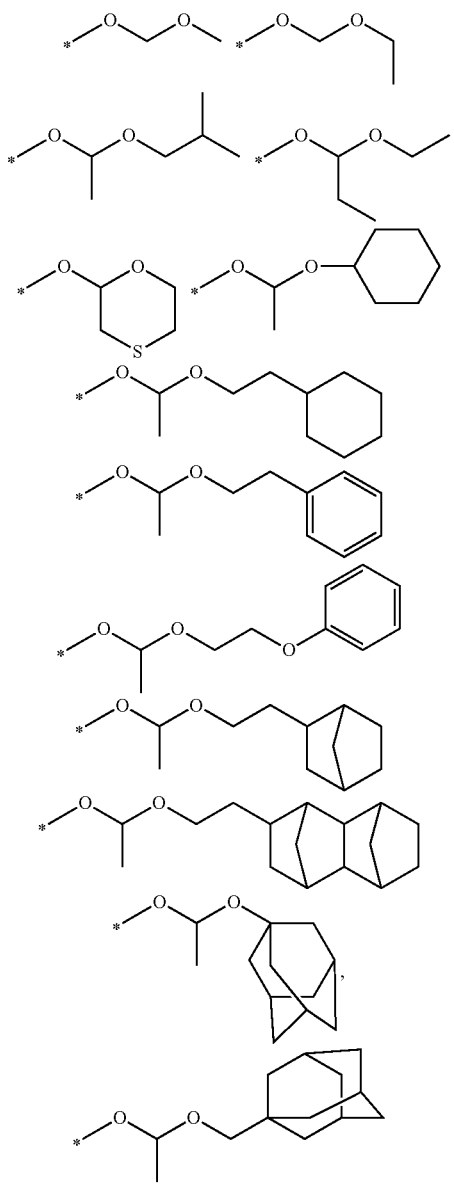

The compound having an acid-labile group is preferably a monomer having an acid-labile group in its side chain and a carbon-carbon double bond, and is more preferably an acrylate monomer having an acid-labile group in its side chain or a methacryalte monomer having an acid-labile group in its side chain.

A monomer having the group represented by the formula (10) or (20) in its side chain and a carbon-carbon double bond is preferable, and an acrylate monomer having the group represented by the formula (10) in its side chain or a methacryalte monomer having the group represented by the formula (10) in its side chain is more preferable.

An acrylate monomer having the group represented by the formula (10) in which $R^{a1}$ and $R^{a2}$ are bonded each other to form a C5-C20 alicycle together with the carbon atom to which they are bonded in its side chain or a methacryalte monomer having the group represented by the formula (10) in which $R^{a1}$ and $R^{a2}$ are bonded each other to form a C5-C20 alicycle together with the carbon atom to which they are bonded in its side chain is especially preferable.

Preferable examples of the compound having an acid-labile group include monomers represented by the formulae (a1-1) and (a1-2):

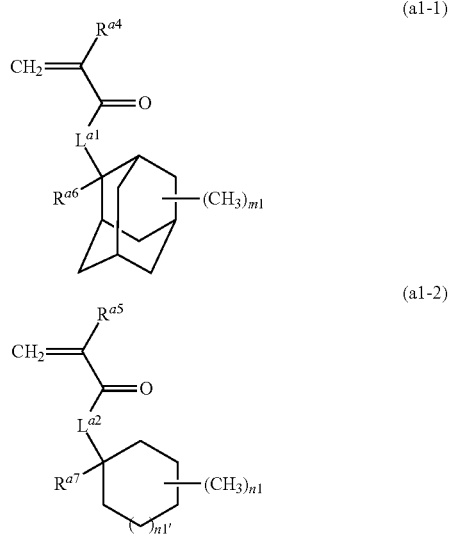

wherein $R^{a4}$ and $R^{a5}$ each independently represents a hydrogen atom or a methyl group, $R^{a6}$ and $R^{a7}$ each independently represents a C1-C8 aliphatic hydrocarbon group or a C3-C10 alicyclic hydrocarbon group, $L^{a1}$ and $L^{a2}$ each independently represents *—O— or *—O—$(CH_2)_{k1}$—CO—O— in which * represents a binding position to —CO—, and k1 represents an integer of 1 to 7, and m1 represents an integer of 0 to 14, n1 represents an integer of 0 to 10, and n1' represents 0 or 1.

The aliphatic hydrocarbon group preferably has 1 to 6 carbon atoms, and the alicyclic hydrocarbon group preferably has 3 to 8 carbon atoms and more preferably 3 to 6 carbon atoms. The alicyclic hydrocarbon group is preferably a saturated aliphatic cyclic hydrocarbon group.

Examples of the aliphatic hydrocarbon group include a C1-C8 alkyl group such as a methyl group, an ethyl group, a propyl group, an isopropyl group, a butyl group, a tert-butyl group, a 2,2-dimethylethyl group, a 1-methylpropyl group, a 2,2-dimethylpropyl group, a 1-ethylpropyl group, a 1-methylbutyl group, a 2-methylbutyl group, a 3-methylbutyl group, a 1-propylbutyl group, a pentyl group, a 1-methylpentyl group, a hexyl group, a 1,4-dimethylhexyl group, a heptyl group, a 1-methylheptyl group and an octyl group. Examples of the saturated cyclic hydrocarbon group include a cyclohexyl group, a methylcyclohexyl group, a dimethylcyclohexyl group, a cycloheptyl group, a methylcycloheptyl group, a norbornyl group and a methylnorbornyl group.

$L^{a1}$ is preferably *—O— or *—O—$(CH_2)_{f1}$—CO—O— in which * represents a binding position to —CO—, and f1 represents an integer of 1 to 4, and is more preferably *—O— or *—O—$CH_2$—CO—O—, and is especially preferably *—O—. $L^{a2}$ is preferably *—O— or *—O—$(CH_2)_{f1}$—CO—O— in which * represents a binding position to —CO—, and f1 is the same as defined above, and is more preferably *—O— or *—O—CH$_2$—CO—O—, and is especially preferably *—O—.

In the formula (a1-1), m1 is preferably an integer of 0 to 3, and is more preferably 0 or 1. In the formula (a1-2), n1 is preferably an integer of 0 to 3, and is more preferably 0 or 1, and n1' is preferably 0 or 1.

$R^{a4}$ and $R^{a5}$ are preferably methyl groups.

Particularly when the photoresist composition contains a resin derived from a monomer having a bulky structure such as a saturated cyclic hydrocarbon group, the photoresist composition having excellent resolution tends to be obtained.

Examples of the monomer represented by the formula (a1-1) include the followings.

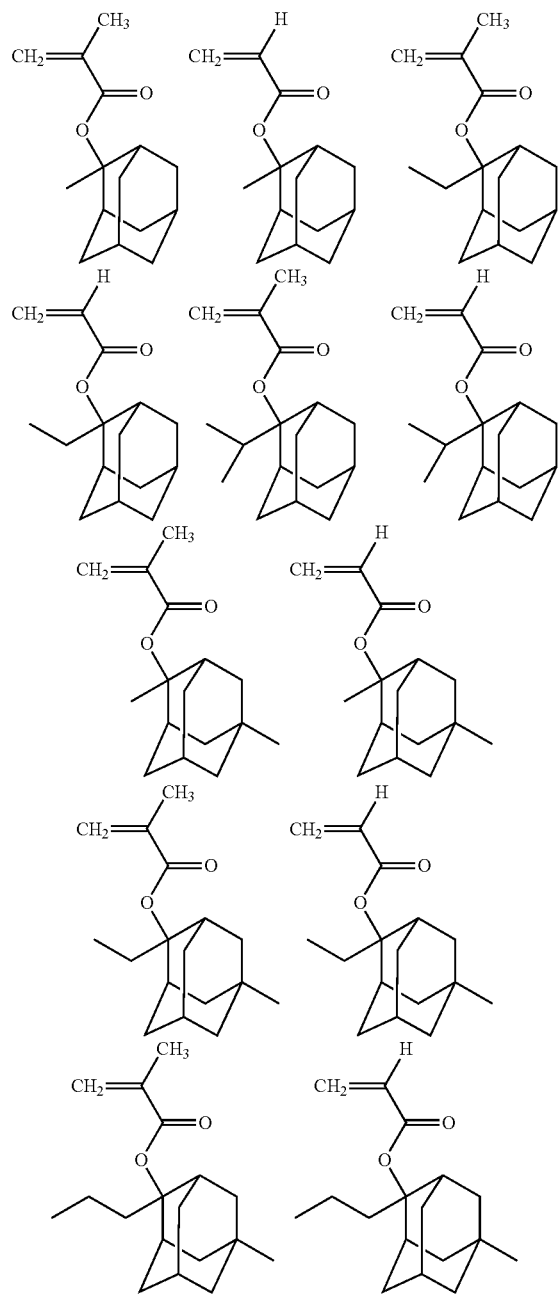

-continued

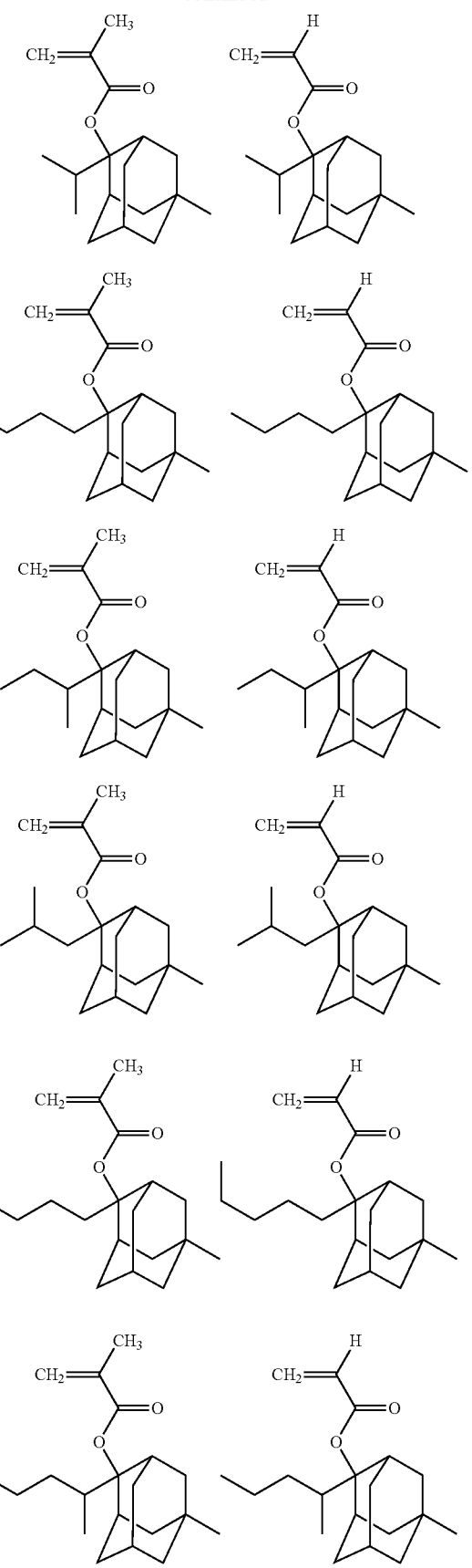

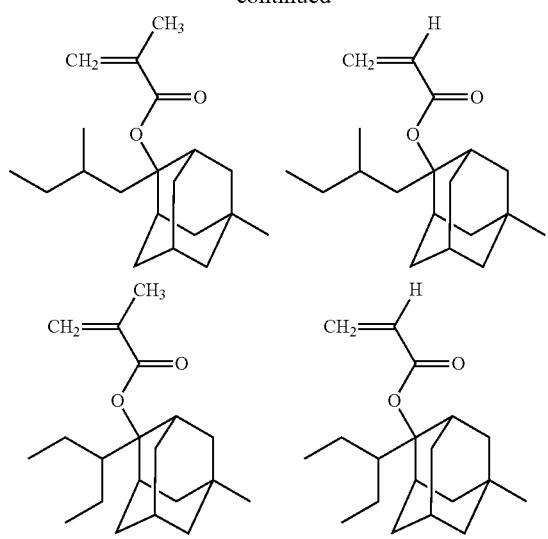
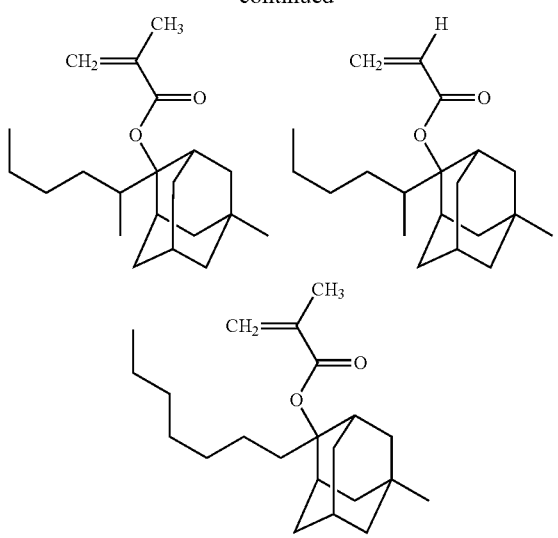

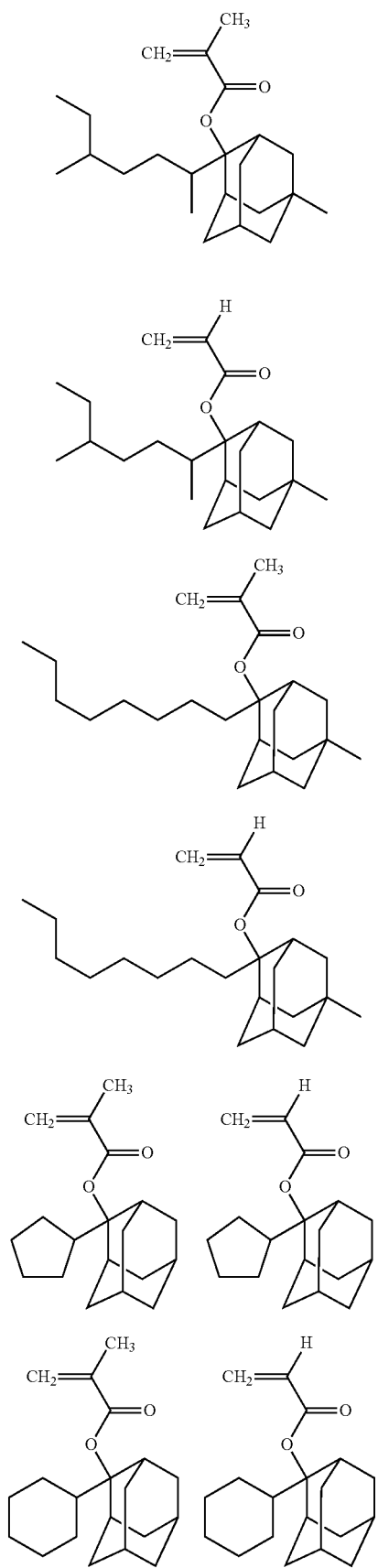
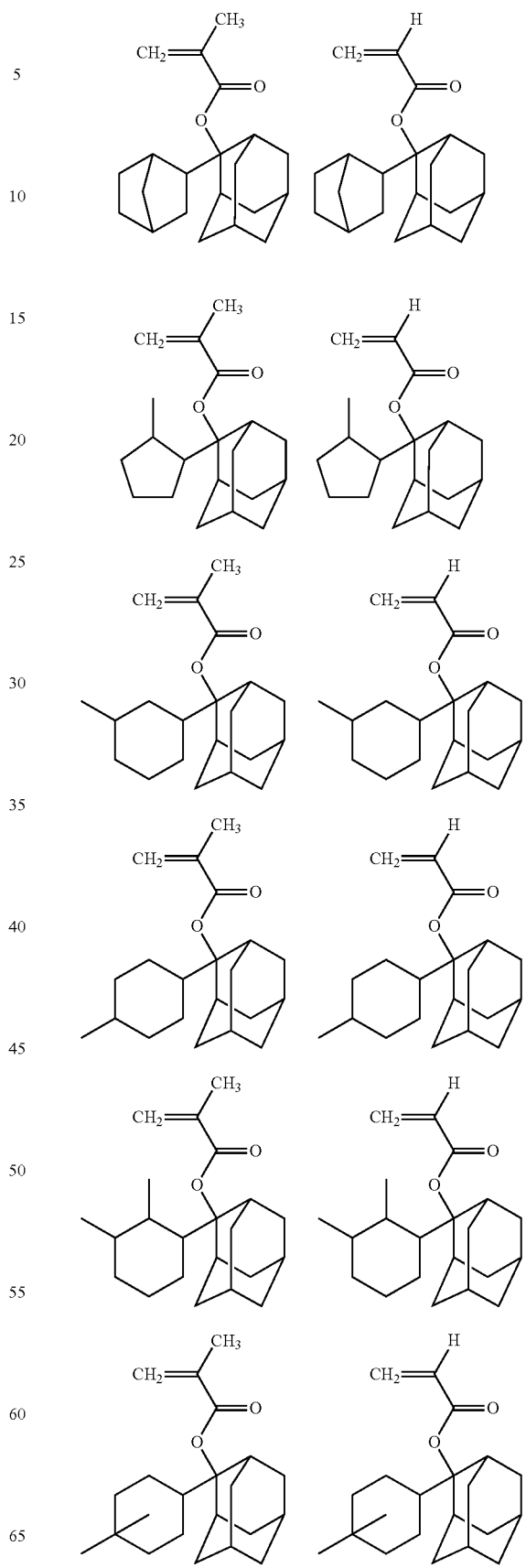

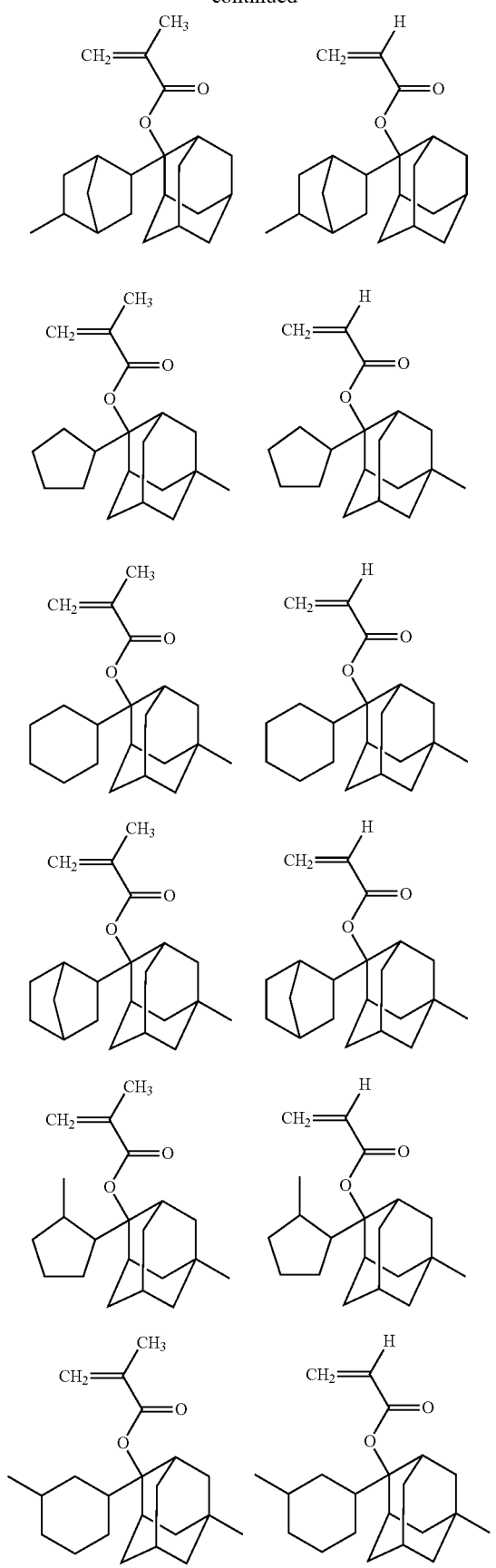
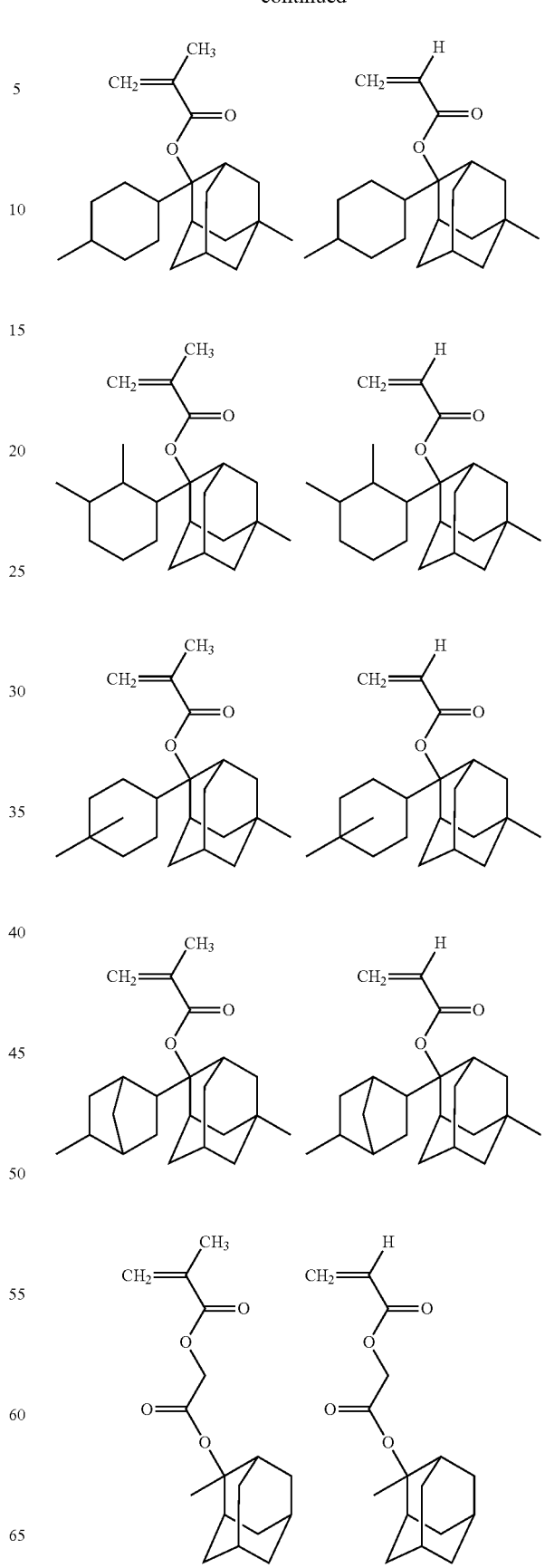

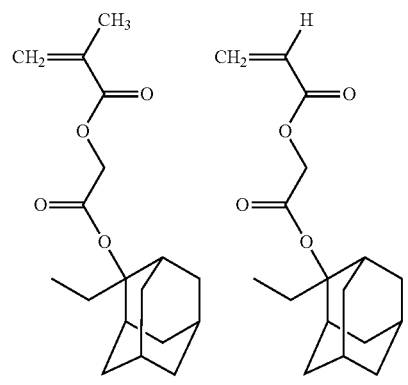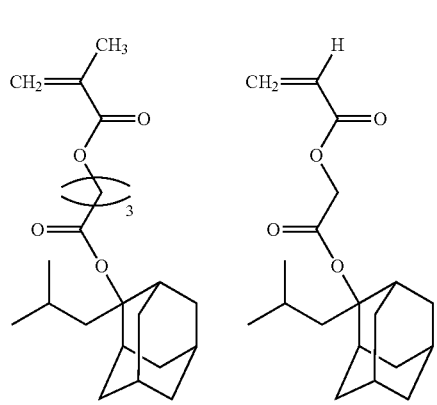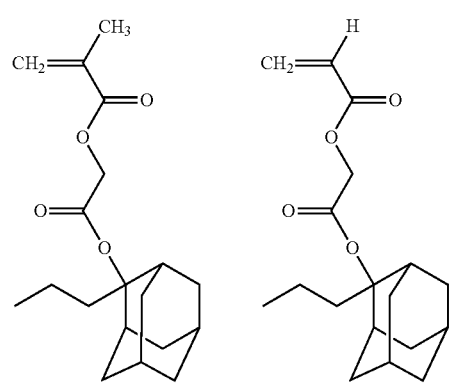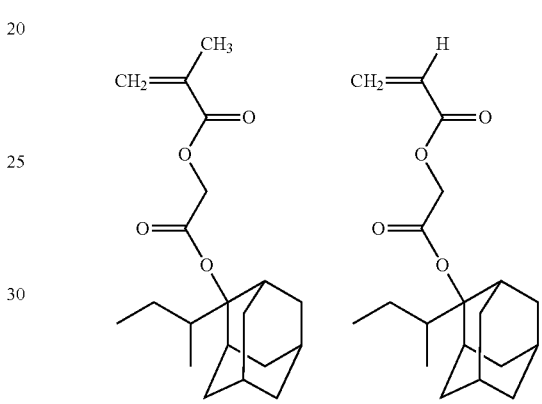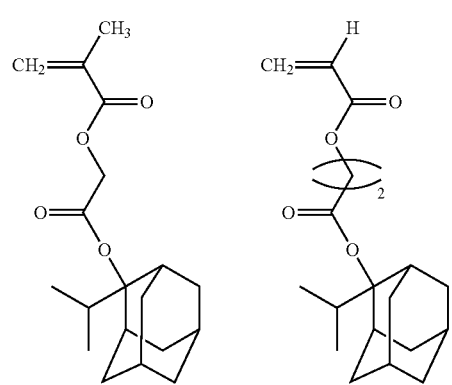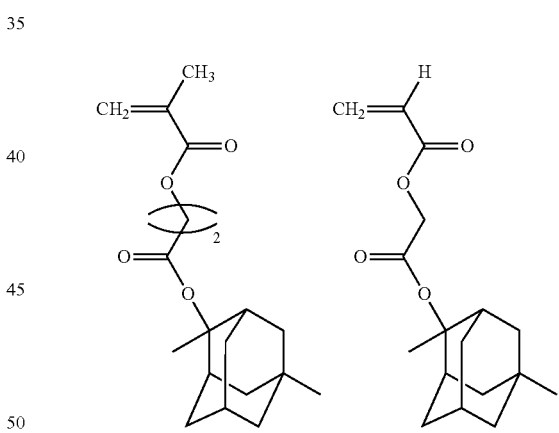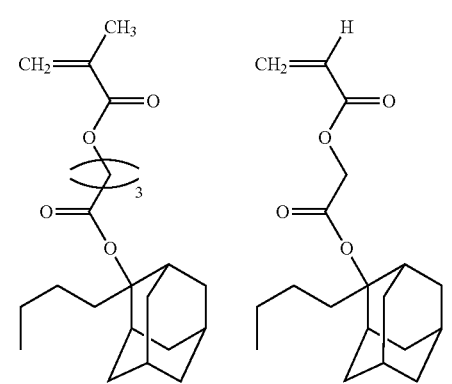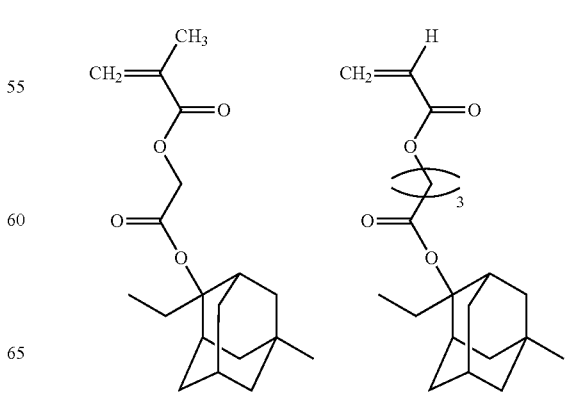

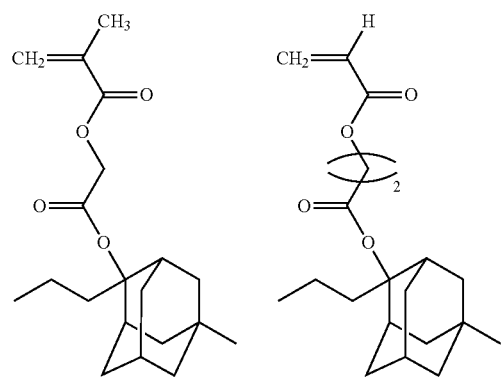
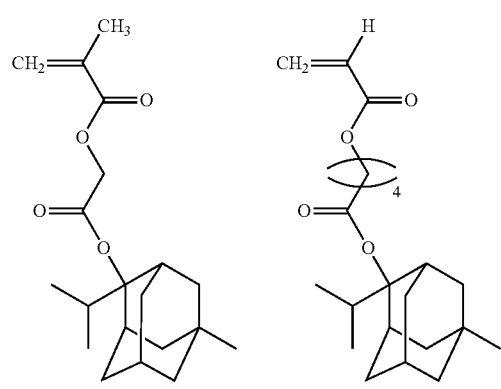
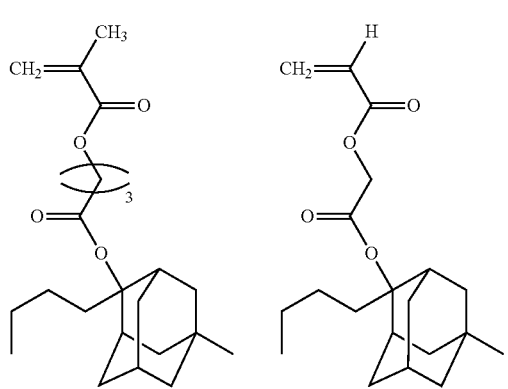
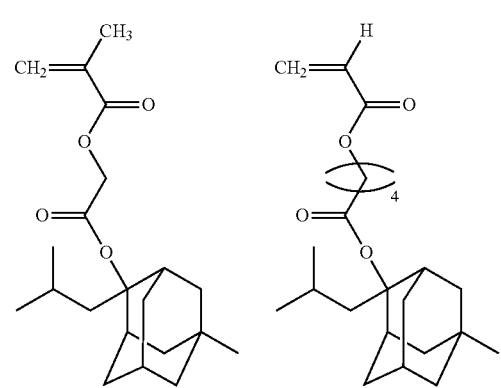
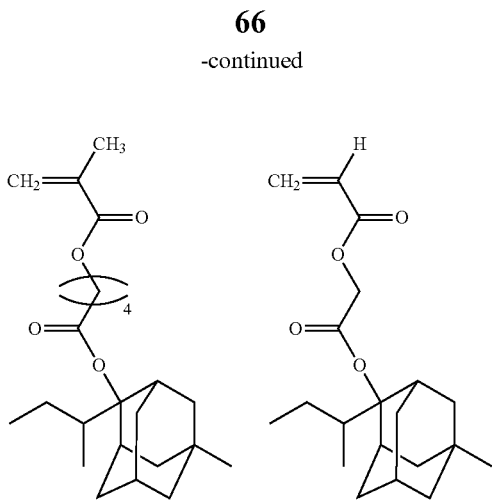
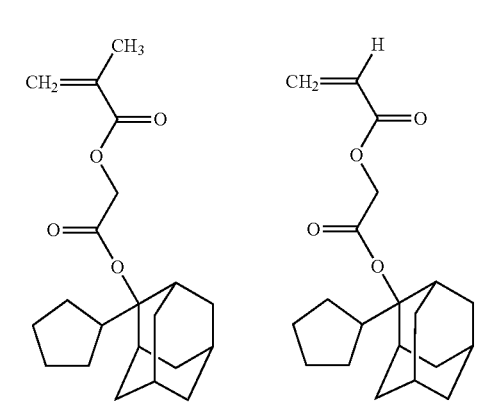
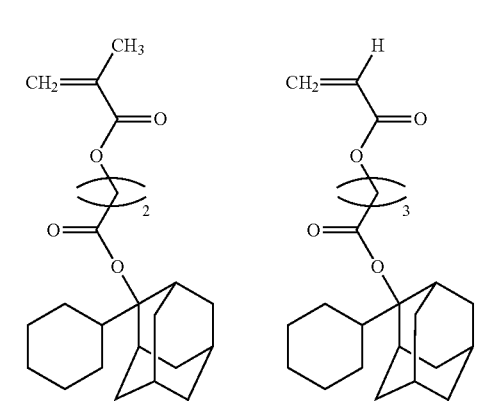
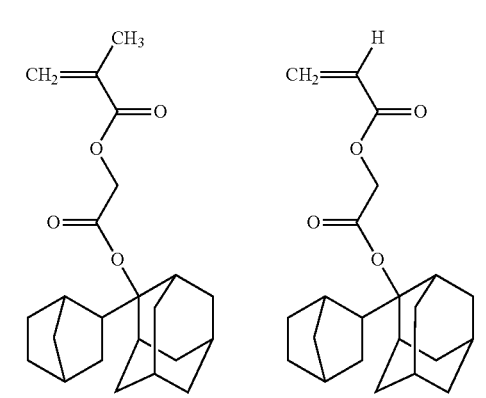

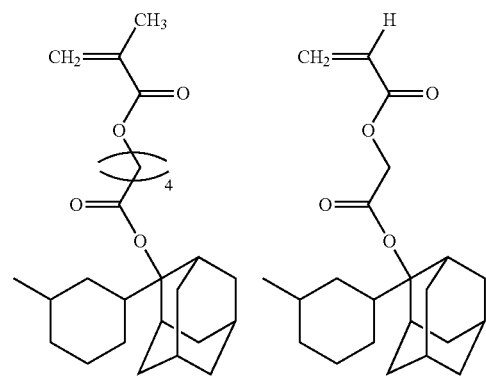
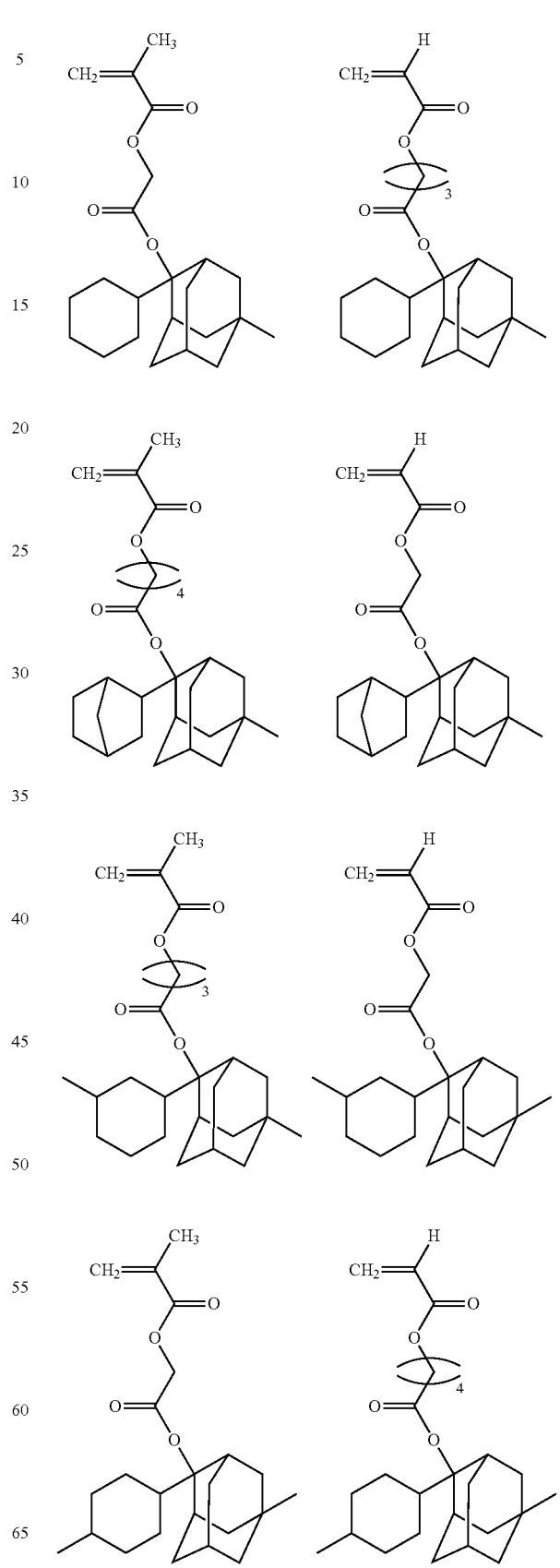

-continued

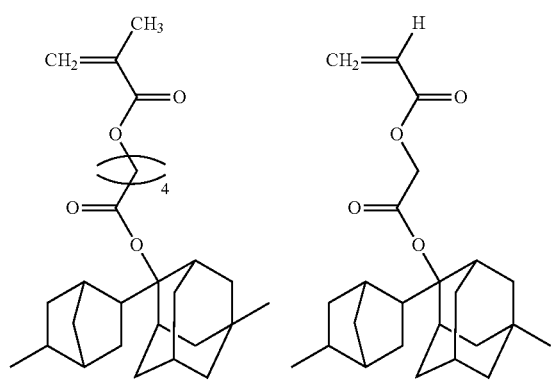

Among them, preferred are 2-methyl-2-adamantyl acrylate, 2-methyl-2-adamantyl methacrylate, 2-ethyl-2-adamantyl acrylate, 2-ethyl-2-adamantyl methacrylate, 2-isopropyl-2-adamantyl acrylate and 2-isopropyl-2-adamantyl methacrylate, and more preferred are 2-methyl-2-adamantyl methacrylate, 2-ethyl-2-adamantyl methacrylate, and 2-isopropyl-2-adamantyl methacrylate.

Examples of the monomer represented by the formula (a1-2) include the followings.

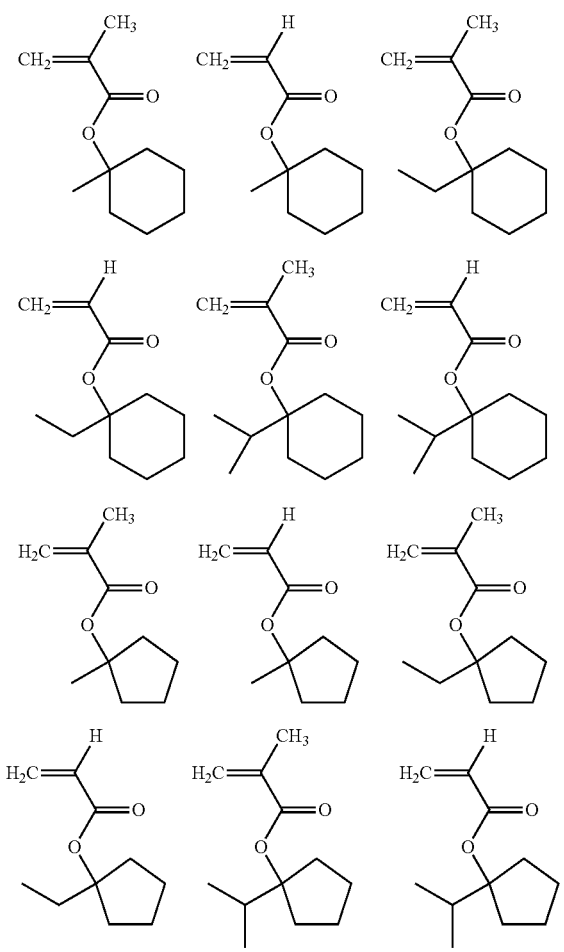

-continued

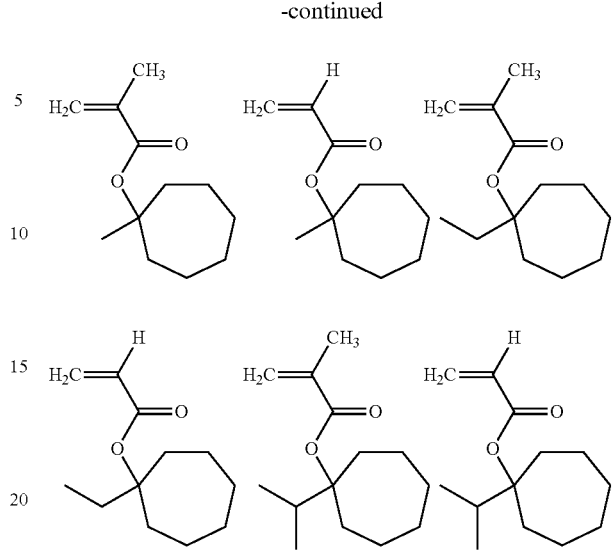

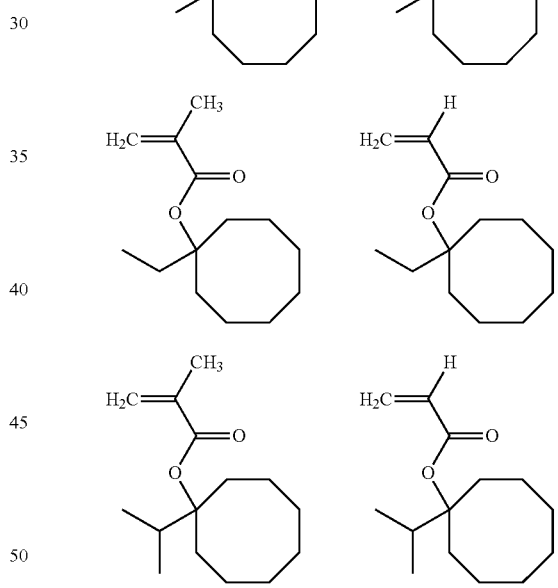

Among them, preferred are 1-ethyl-1-cyclohexyl acrylate and 1-ethyl-1-cyclohexyl methacrylate, and more preferred is 1-ethyl-1-cyclohexyl methacrylate.

The content of the structural unit derived from a monomer having an acid-labile group in the resin is usually 10 to 95% by mole, preferably 15 to 90% by mole and more preferably 20 to 85% by mole based on 100% by mole of all the structural units of the resin.

Other examples of the monomer having an acid-labile group include a monomer represented by the formula (a1-3):

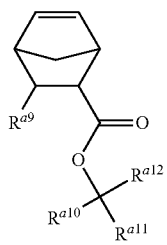

(a1-3)

wherein $R^{a9}$ represents a hydrogen atom, a C1-C3 aliphatic hydrocarbon group which can have one or more hydroxyl groups, a carboxyl group, a cyano group or a —$COOR^{a13}$ group in which $R^{a13}$ represents a C1-C8 aliphatic hydrocarbon group or a C3-C8 saturated cyclic hydrocarbon group, and the C1-C8 aliphatic hydrocarbon group and the C3-C8 saturated cyclic hydrocarbon group can have one or more hydroxyl groups, and one or more —$CH_2$— in the C1-C8 aliphatic hydrocarbon group and the C3-C8 saturated cyclic hydrocarbon group can be replaced by —O— or —CO—, $R^{a10}$, $R^{a11}$ and $R^{a12}$ each independently represent a C1-C12 aliphatic hydrocarbon group or a C3-C12 saturated cyclic hydrocarbon group, and $R^{a10}$ and $R^{a11}$ can be bonded each other to form a C3-C20 ring together with the carbon atom to which $R^{a10}$ and $R^{a11}$ are bonded, and the C1-C12 aliphatic hydrocarbon group and the C3-C12 saturated cyclic hydrocarbon group can have one or more hydroxyl groups, and one or more —$CH_2$— in the C1-C12 aliphatic hydrocarbon group and the C3-C12 saturated cyclic hydrocarbon group can be replaced by —O— or —CO—.

Examples of the C1-C3 aliphatic hydrocarbon group which can have one or more hydroxyl groups include a methyl group, an ethyl group, a propyl group, a hydroxymethyl group and a 2-hydroxyethyl group. Examples of $R^{a13}$ include a methyl group, an ethyl group, a propyl group, a 2-oxo-oxolan-3-yl group and a 2-oxo-oxolan-4-yl group. Examples of $R^{a10}$, $R^{a11}$ and $R^{a12}$ include a methyl group, an ethyl group, a cyclohexyl group, a methylcyclohexyl group, a hydroxycyclohexyl group, an oxocyclohexyl group and an adamantyl group, and examples of the C3-C20 ring formed by bonding $R^{a10}$ and $R^{a11}$ each other together with the carbon atom to which $R^{a10}$ and $R^{a11}$ are bonded include a cyclohexane ring and an adamantane ring.

Examples of the monomer represented by the formula (a1-3) include tert-butyl 5-norbornene-2-carboxylate, 1-cyclohexyl-1-methylethyl 5-norbornene-2-carboxylate, 1-methylcyclohexyl 5-norbornene-2-carboxylate, 2-methyl-2-adamantyl 5-norbornene-2-carboxylate, 2-ethyl-2-adamantyl 5-norbornene-2-carboxylate, 1-(4-methylcyclohexyl)-1-methylethyl 5-norbornene-2-carboxylate, 1-(4-hydroxylcyclohexyl)-1-methylethyl 5-norbornene-2-carboxylate, 1-methyl-1-(4-oxocyclohexyl) ethyl 5-norbornene-2-carboxylate and 1-(1-adamantyl)-1-methylethyl 5-norbornene-2-carboxylate.

When the resin has a structural unit derived from the monomer represented by the formula (a1-3), the photoresist composition having excellent resolution and higher dry-etching resistance tends to be obtained.

When the resin contains the structural unit derived form the monomer represented by the formula (a1-3), the content of the structural unit derived from the monomer represented by the formula (a1-3) is usually 10 to 95% by mole and preferably 15 to 90% by mole and more preferably 20 to 85% by mole based on total molar of all the structural units of the resin.

Other examples of the compound having an acid-labile group include a monomer represented by the formula (a1-4):

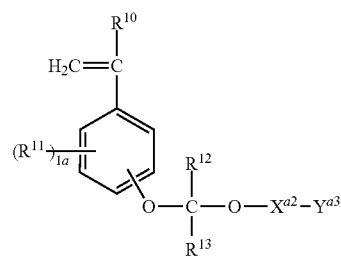

(a1-4)

wherein $R^{10}$ represents a hydrogen atom, a halogen atom, a C1-C6 alkyl group or a C1-C6 halogenated alkyl group, $R^{11}$ is independently in each occurrence a halogen atom, a hydroxyl group, a C1-C6 alkyl group, a C1-C6 alkoxy group, a C2-C4 acyl group, a C2-C4 acyloxy group, an acryloyl group or a methacryloyl group, la represents an integer of 0 to 4, $R^{12}$ and $R^{13}$ each independently represent a hydrogen atom or a C1-C12 hydrocarbon group, $X^{a2}$ represents a single bond or a C1-C17 divalent saturated hydrocarbon group in which one or more —$CH_2$— can be replaced by —O—, —CO—, —S—, —$SO_2$— or —$N(R^c)$— wherein $R^c$ represents a hydrogen atom or a C1-C6 alkyl group, and $Y^{a3}$ represents a C1-C12 aliphatic hydrocarbon group, a C3-C18 saturated cyclic hydrocarbon group or a C6-C18 aromatic hydrocarbon group, and the C1-C17 divalent saturated hydrocarbon group, the C1-C12 aliphatic hydrocarbon group, the C2-C18 saturated cyclic hydrocarbon group and the C6-C18 aromatic hydrocarbon group can have one or more substituents selected from the group consisting of a halogen atom, a hydroxyl group, a C1-C6 alkyl group, a C1-C6 alkoxy group, a C2-C4 acyl group and a C2-C4 acyloxy group.

Examples of the halogen atom include a fluorine atom, a chlorine atom, a bromine atom and an iodine atom.

Examples of the C1-C6 alkyl group include a methyl group, an ethyl group, a propyl group, an isopropyl group, a butyl, group, an isobutyl group, a sec-butyl group, a tert-butyl group, a pentyl group and a hexyl group, and a C1-C4 alkyl group is preferable and a C1-C2 alkyl group is more preferable and a methyl group is especially preferable.

Examples of the C1-C6 halogenated alkyl group include a trifluoromethyl group, a pentafluoroethyl group, a heptafluoropropyl group, a heptafluoroisopropyl group, a nonafluorobutyl group, a nonafluoro-sec-butyl group, a nonafluoro-tert-butyl group, a perfluoropentyl group, a perfluorohexyl group, a perchloromethyl group, a perbromomethyl group and a periodomethyl group.

Examples of the C1-C6 alkoxy group include a methoxy group, an ethoxy group, a propoxy group, an isopropoxy group, a butoxy group, an isobutoxy group, a sec-butoxy group, a tert-butoxy group, a pentyloxy group and a hexyloxy group, and a C1-C4 alkoxy group is preferable and a C1-C2 alkoxy group is more preferable and a methoxy group is especially preferable.

Examples of the C2-C4 acyl group include an acetyl group, a propionyl group and a butyryl group, and examples of the C2-C4 acyloxy group include an acetyloxy group, a propionyloxy group and a butyryloxy group.

Examples of the C1-C12 hydrocarbon group include a C1-C12 aliphatic hydrocarbon group such as a methyl group, an ethyl group, a propyl group, an isopropyl group, a butyl group, an isobutyl group, a sec-butyl group, a tart-butyl group, a pentyl group, a hexyl group, a heptyl group, an octyl group, a 2-ethylhexyl group, a nonyl group, a decyl group, an undecyl group and a dodecyl group, a C3-C12 alicyclic hydrocarbon group such as a cyclohexyl group, an adamantyl group, a 2-alkyl-2-adamantyl group, a 1-(1-adamantyl)-1-alkyl group and an isobornyl group, an C6-C12 aromatic hydrocarbon group and a group formed by combining one or more above-mentioned groups. Among them, preferred are an isopropyl group, a butyl group, a sec-butyl group, a tert-butyl group, a pentyl group, a hexyl group, an octyl group, a 2-ethylhexyl group, a cyclohexyl group, an adamantyl group, a 2-alkyl-2-adamantyl group, a 1-(1-adamantyl)-1-alkyl group and an isobornyl group.

Examples of the C1-C17 divalent saturated hydrocarbon group include a C1-C17 alkanediyl group such as a methylene group, an ethylene group, a propane-1,3-diyl group, a butane-1,4-diyl group, a pentane-1,5-diyl group, a hexane-1,6-diyl group, a heptane-1,7-diyl group, an octane-1,8-diyl group, a nonane-1,9-diyl group, a decane-1,10-diyl group, a undecane-1,11-diyl group, a dodecane-1,12-diyl group, a tridecane-1,13-diyl group, a tetradecane-1,14-diyl group, a pentadecane-1,15-diyl group, a hexadecane-1,16-diyl group and a heptadecane-1,17-diyl group.

Examples of the C1-C12 aliphatic hydrocarbon group include a methyl group, an ethyl group, a propyl group, an isopropyl group, a butyl group, an isobutyl group, a sec-butyl group, a tert-butyl group, a pentyl group, a hexyl group, a heptyl group, an octyl group, a 2-ethylhexyl group, a nonyl group, a decyl group, an undecyl group and a dodecyl group. Examples of the C3-C18 saturated cyclic hydrocarbon group include a cyclopropyl group, a cyclobutyl group, a cyclopentyl group, a cyclohexyl group, a cycloheptyl group, a cyclooctyl group, a cyclononyl group, a cyclodecyl group, a norbornyl group, a 1-adamantyl group, a 2-adamantyl group, an isobornyl group and the following groups:

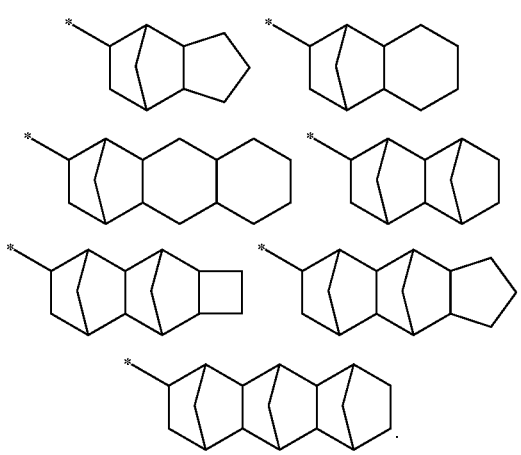

Examples of the C6-C18 aromatic hydrocarbon group include a phenyl group, a naphthyl group, an anthryl group, a p-methylphenyl group, a p-tert-butylphenyl group and a p-adamantylphenyl group.

Preferred substituents of $X^{a2}$ and $X^{a3}$ is a hydroxyl group.

Examples of the monomer represented by the formula (a1-4) include the followings.

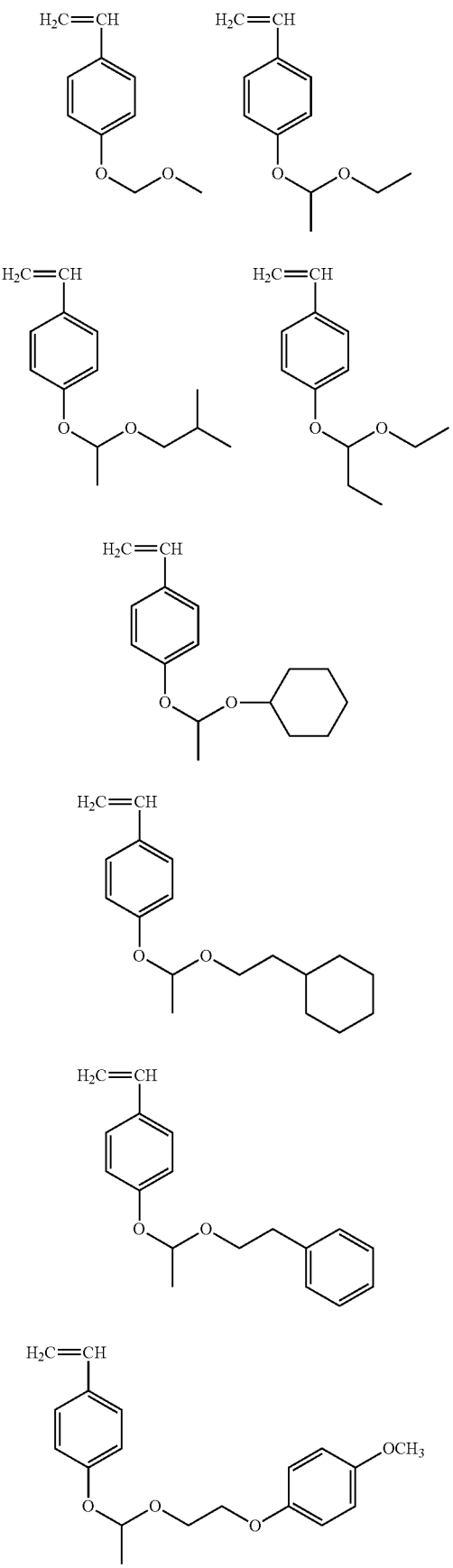

-continued
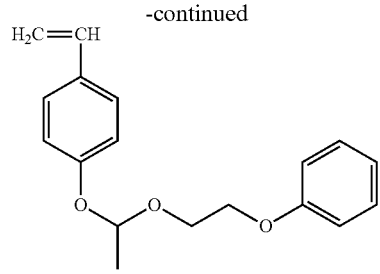
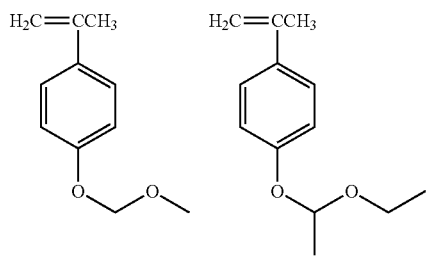
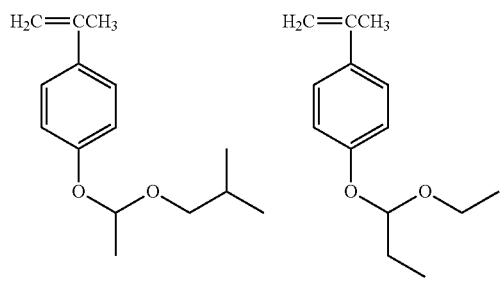
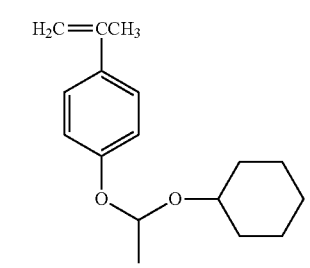
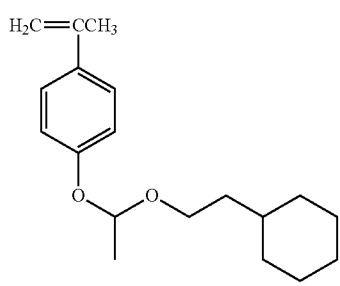
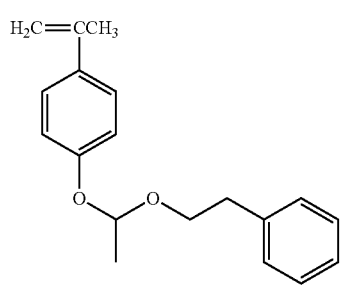
-continued
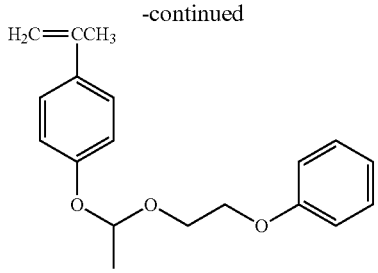
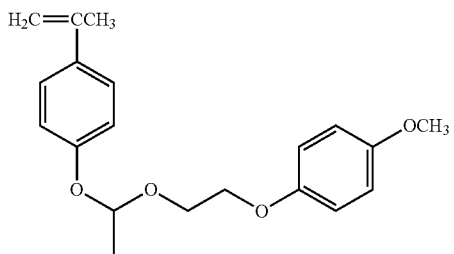
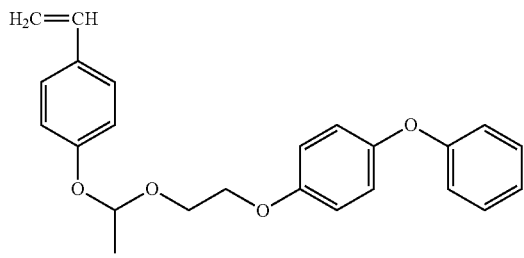
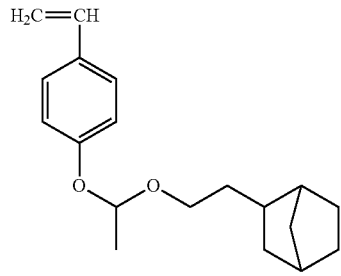
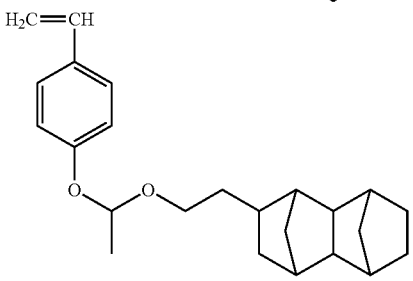
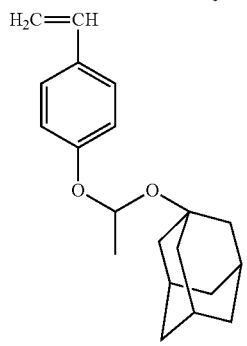

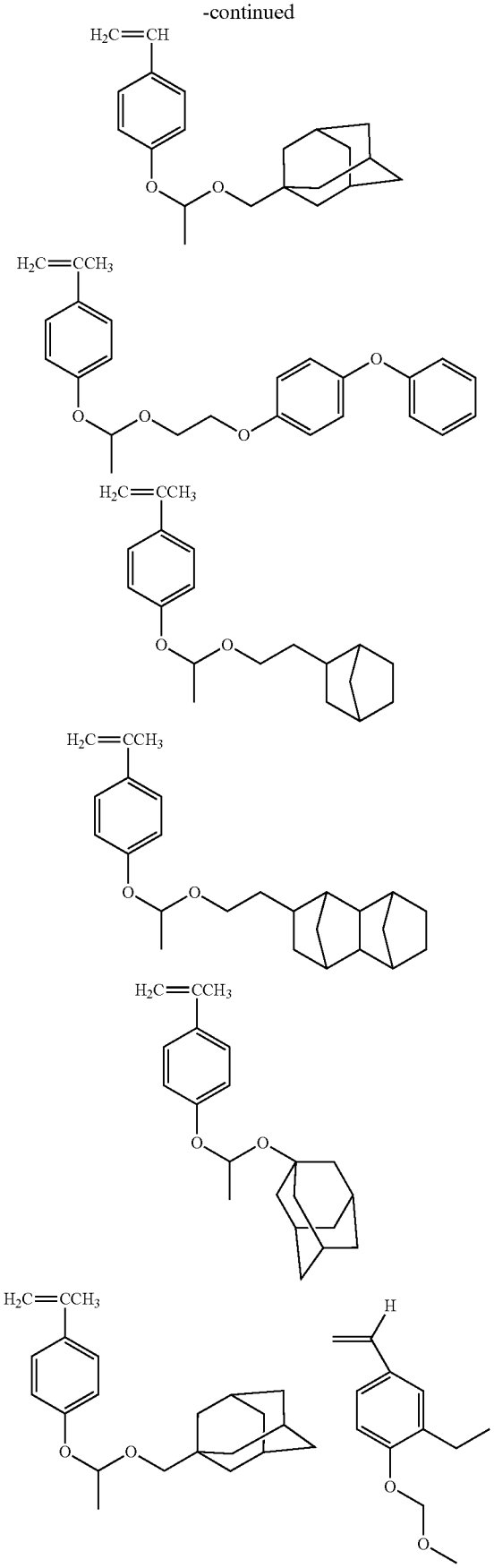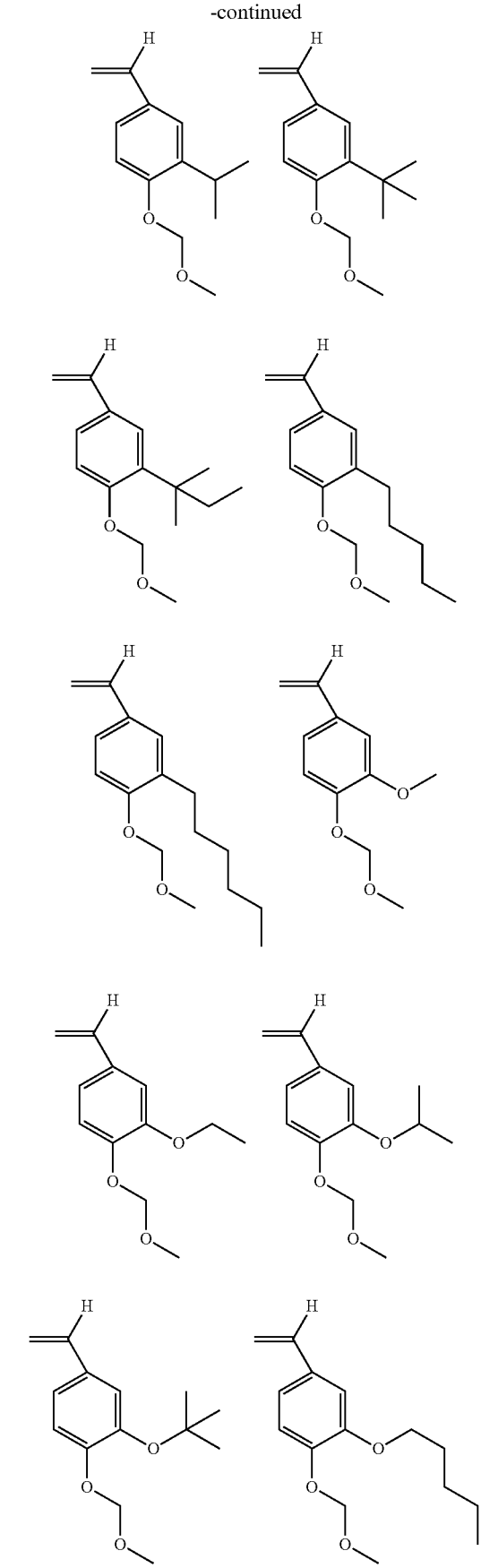

-continued
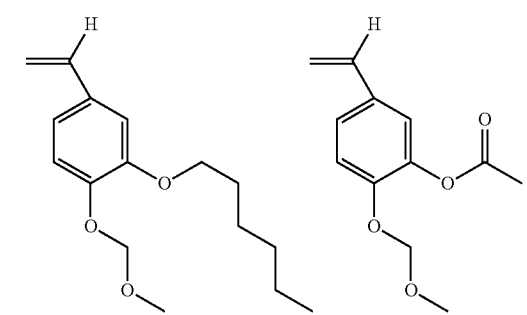
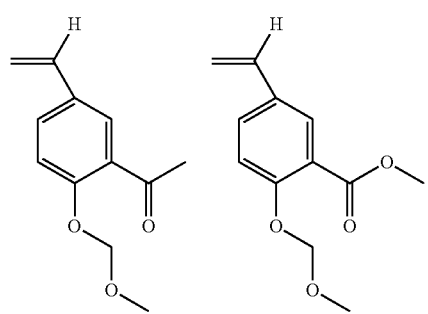
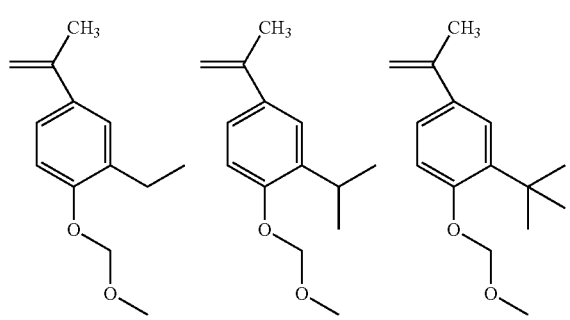
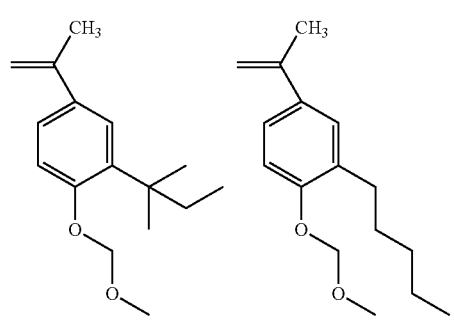
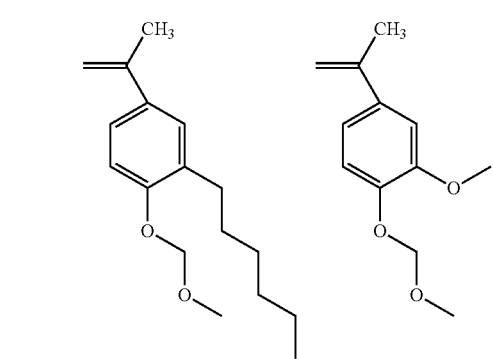
-continued
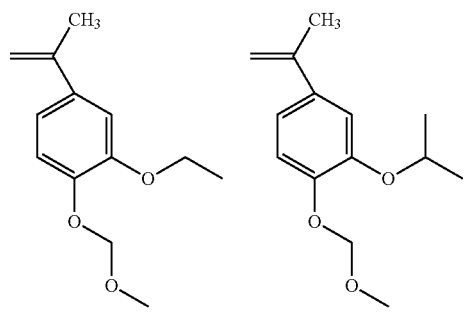
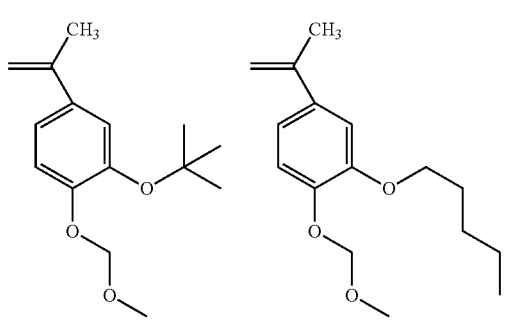
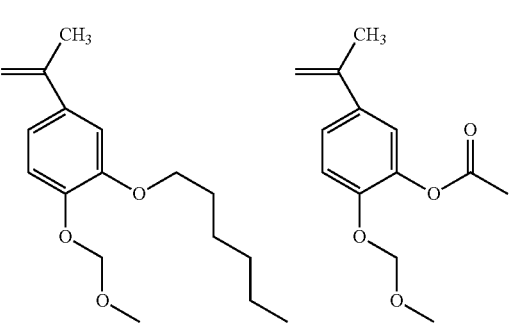
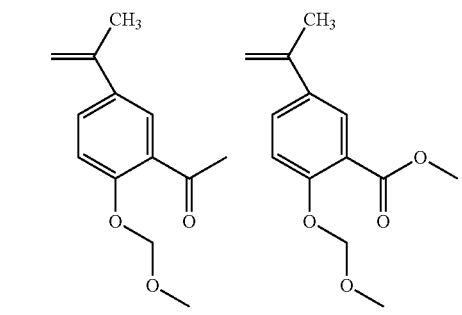
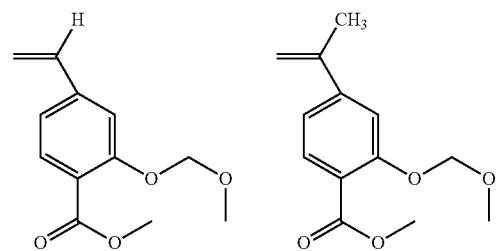

-continued

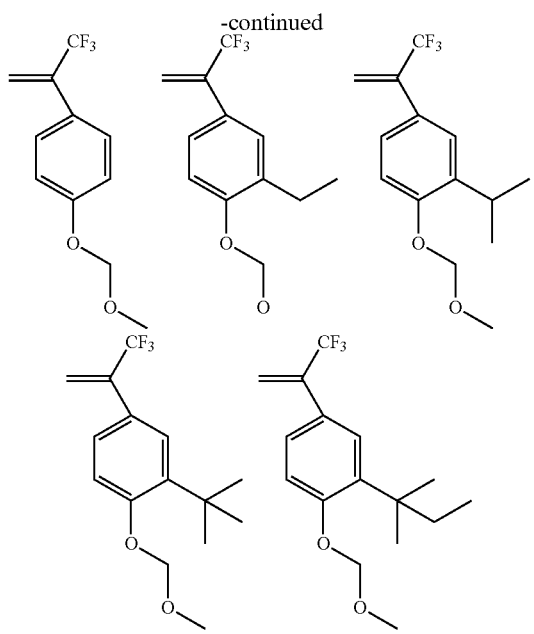

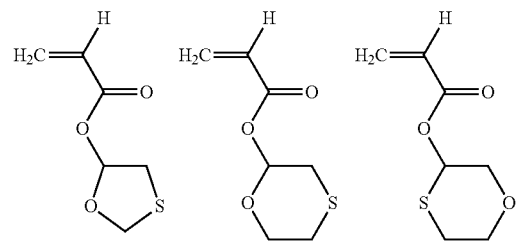

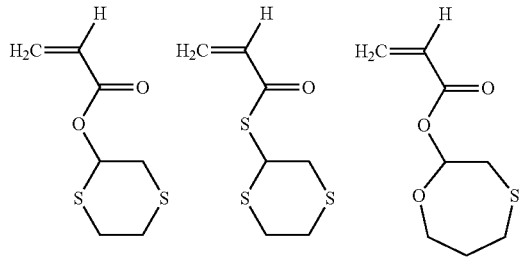

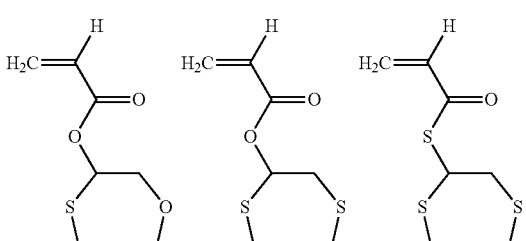

When the resin contains the structural unit derived form the monomer represented by the formula (a1-4), the content of the structural unit derived from the monomer represented by the formula (a1-4) is usually 10 to 95% by mole and preferably 15 to 90% by mole and more preferably 20 to 85% by mole based on total molar of all the structural units of the resin.

Other examples of the compound having an acid-labile group include a monomer represented by the formula (a1-5):

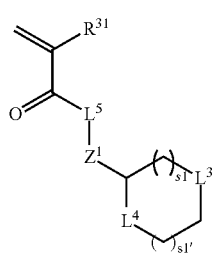

(a1-5)

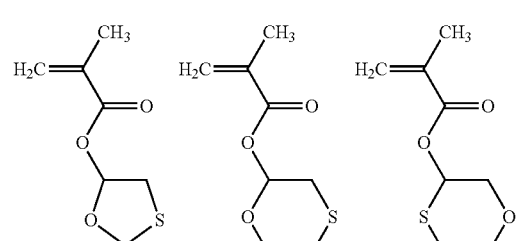

wherein $R^{31}$ represents a hydrogen atom, a halogen atom, a C1-C4 alkyl group which may be substituted with a halogen atom, $L^5$ represents —O—, —S— or *—O—$(CH_2)_{k1}$—CO—O—, k1 represents an integer of 1 to 7, * represents a binding position to —CO—, $L^3$ and $L^4$ independently each represent —O— or —S—, $Z^1$ represents a single bond or a C1-C6 alkylene group in which one or more —$CH_2$— may be replaced by —O— or —CO—, s1 and s1' independently each represent an integer of 0 to 4.

$R^{31}$ is preferably a hydrogen atom or a methyl groups $L^5$ is preferably —O—.

It is preferred that one of $L^3$ and $L^4$ is —O— and the other is —S—.

In the formula (a1-5), s1 is preferably 1 and s1' is preferably 0, 1 or 2.

$Z^1$ is preferably a single bond or —$CH_2$—CO—O—.

Examples of the monomer represented by the formula (a1-5) include the following.

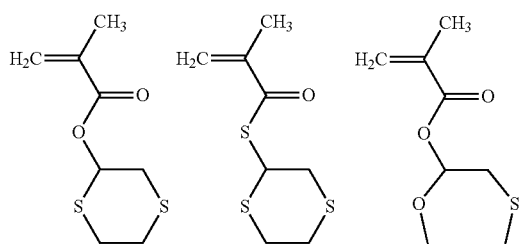

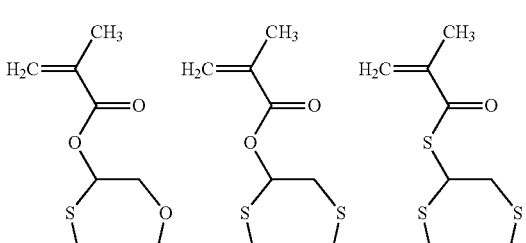

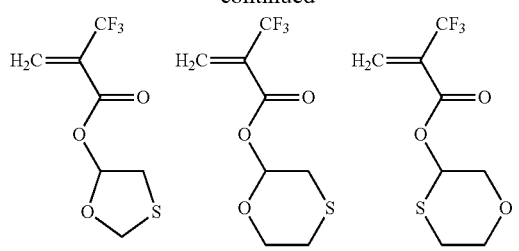
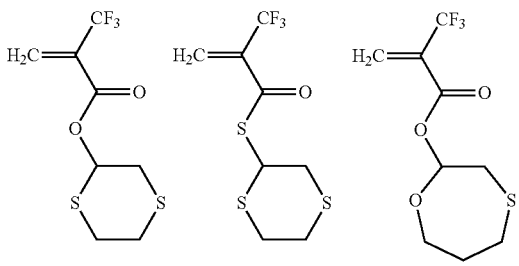
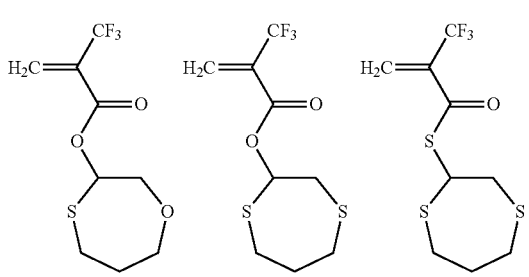
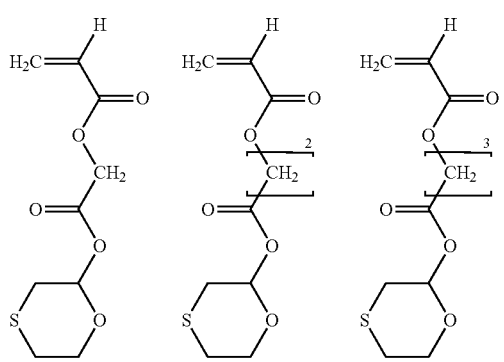
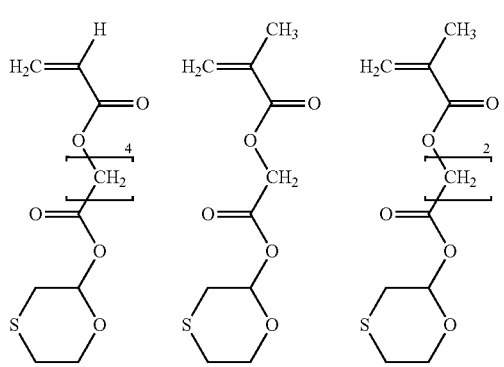
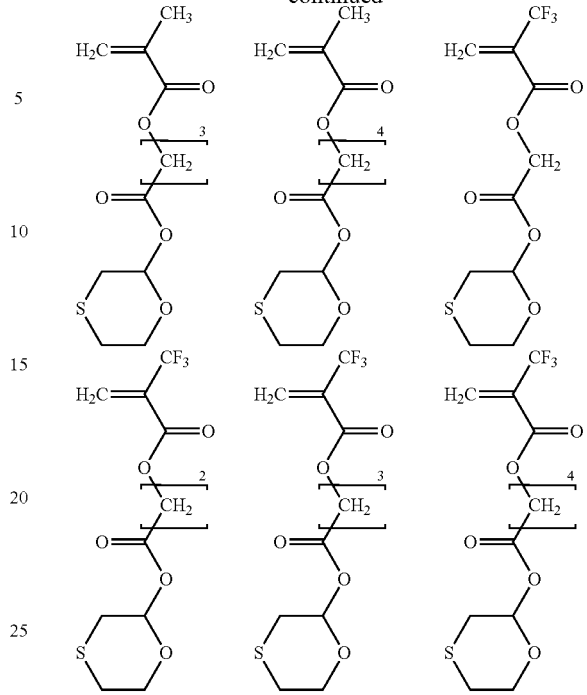

When the resin contains the structural unit derived form the monomer represented by the formula (a1-5), the content of the structural unit derived from the monomer represented by the formula (a1-5) is usually 10 to 95% by mole and preferably 15 to 90% by mole and more preferably 20 to 85% by mole based on total molar of all the structural units of the resin.

The resin can have two or more kinds of structural units derived from the monomers having an acid-labile group.

The resin preferably contains the structural unit derived from the monomer having an acid-labile group and a structural unit derived from the monomer having no acid-labile group. The resin can have two or more kinds of structural units derived from the monomers having no acid-labile group. When the resin contains the structural unit derived from the monomer having an acid-labile group and the structural unit derived from the monomer having no acid-labile group, the content of the structural unit derived from the monomer having an acid-labile group is usually 10 to 80% by mole and preferably 20 to 60% by mole based on total molar of all the structural units of the resin. The content of the structural unit derived from a monomer having an adamantyl group, especially the monomer represented by the formula (a1-1) in the structural unit derived from the compound having no acid-labile group is preferably 15% by mole or more from the viewpoint of dry-etching resistance of the photoresist composition.

The monomer having no acid-labile group preferably contains one or more hydroxyl groups or a lactone ring, when the resin contains the structural unit derived from the monomer having no acid-labile group and having one or more hydroxyl groups or a lactone ring, a photoresist composition having good resolution and adhesiveness of photoresist to a substrate tends to be obtained.

Examples of the monomer having no acid-labile group and having one or more hydroxyl groups include a monomer represented by the formula (a2-0):

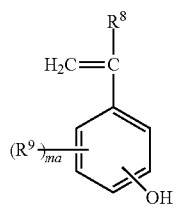

(a2-0)

wherein $R^8$ represents a hydrogen atom, a halogen atom, a C1-C6 alkyl group or a C1-C6 halogenated alkyl group, $R^9$ is independently in each occurrence a halogen atom, a hydroxyl group, a C1-C6 alkyl group, a C1-C6 alkoxy group, a C2-C4 acyl group, a C2-C4 acyloxy group, an acryloyl group or a methacryloyl group, ma represents an integer of 0 to 4, and a monomer represented by the formula (a2-1):

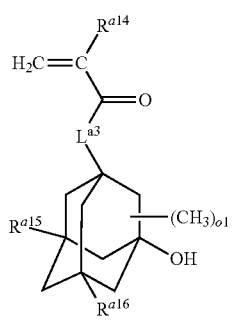

(a2-1)

wherein $R^{a14}$ represents a hydrogen atom or a methyl group, $R^{a15}$ and $R^{a16}$ each independently represent a hydrogen atom, a methyl group or a hydroxyl group, $L^{a3}$ represents *—O— or *—O—$(CH_2)_{k2}$—CO—O— in which * represents a binding position to —CO—, and k2 represents an integer of 1 to 7, and of represents an integer of 0 to 10.

When KrF excimer laser (wavelength: 248 nm) lithography system, or a high energy laser such as electron beam and extreme ultraviolet is used as an exposure system, the resin containing the structural unit derived from the monomer represented by the formula (a2-0) is preferable, and when ArF excimer laser (wavelength: 193 nm) is used as an exposure system, the resin containing the structural unit derived from the monomer represented by the formula (a2-1) is preferable.

In the formula (a2-0), examples of the halogen atom include a fluorine atom, examples of the C1-C6 alkyl group include a methyl group, an ethyl group, a propyl group, an isopropyl group, a butyl group, an isobutyl group, a sec-butyl group, a tert-butyl group, a pentyl group and a hexyl group, and a C1-C4 alkyl group is preferable and a C1-C2 alkyl group is more preferable and a methyl group is especially preferable. Examples of the C1-C6 halogenated alkyl group include a trifluoromethyl group, a pentafluoroethyl group, a heptafluoropropyl group, a heptafluoroisopropyl group, a nonafluorobutyl group, a nonafluoro-sec-butyl group, a nonafluoro-tert-butyl group, a perfluoropentyl group and a perfluorohexyl group. Examples of the C1-C6 alkoxy group include a methoxy group, an ethoxy group, a propoxy group, an isopropoxy group, a butoxy group, an isobutoxy group, a sec-butoxy group, a tert-butoxy group, a pentyloxy group and a hexyloxy group, and a C1-C4 alkoxy group is preferable and a C1-C2 alkoxy group is more preferable and a methoxy group is especially preferable. Examples of the C2-C4 acyl group include an acetyl group, a propionyl group and a butyryl group, and examples of the C2-C4 acyloxy group include an acetyloxy group, a propionyloxy group and a butyryloxy group. In the formula (a2-0), ma is preferably 0, 1 or 2, and is more preferably 0 or 1, and especially preferably 0.

The resin containing the structural unit derived from the monomer represented by the formula (a2-0) can be produced, for example, by polymerizing a monomer obtained by protecting a hydroxyl group of the monomer represented by the formula (a2-0) with a protecting group such as an acetyl group followed by conducting deprotection of the obtained polymer with an acid or a base.

Examples of the monomer represented by the formula (a2-0) include the followings.

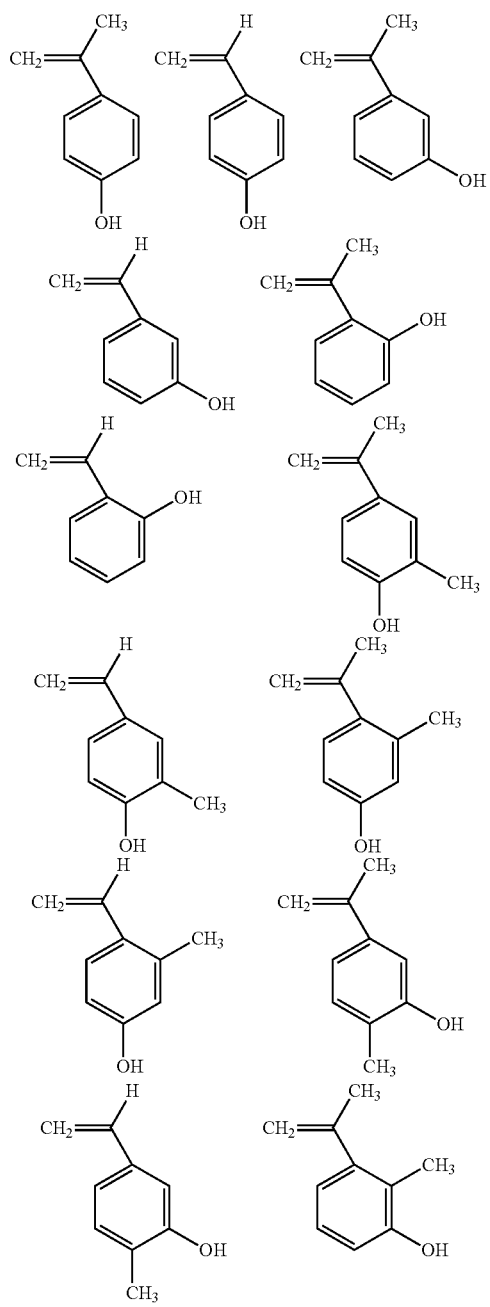

-continued
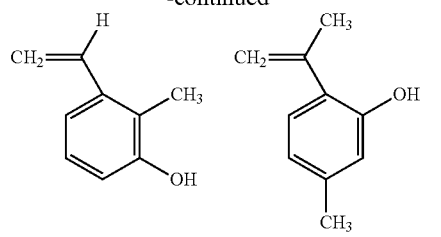
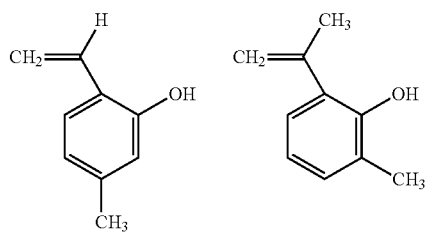
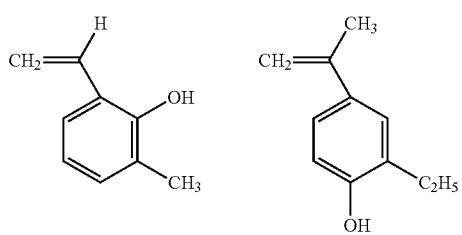
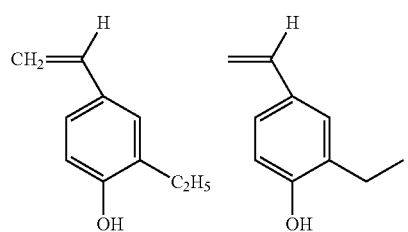
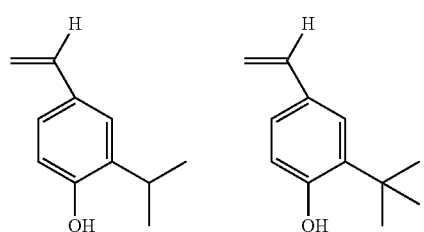
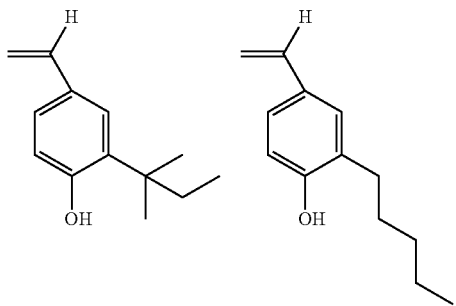
-continued
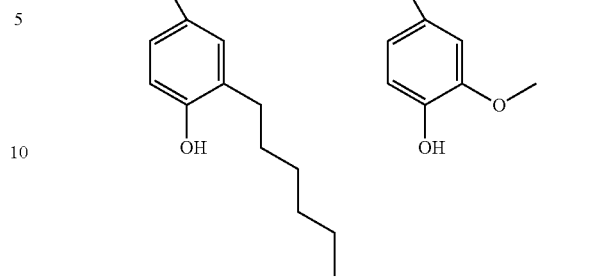
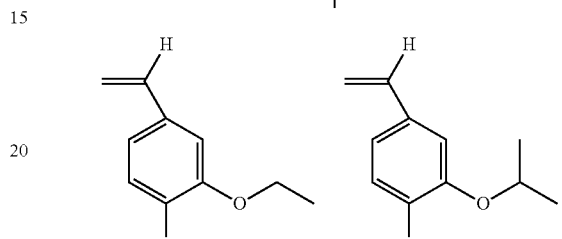
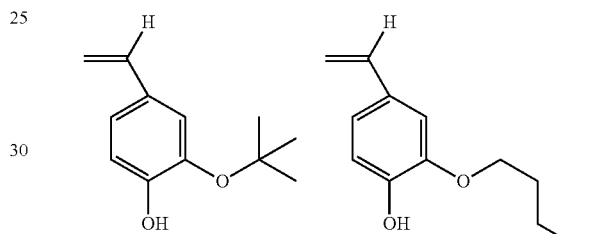
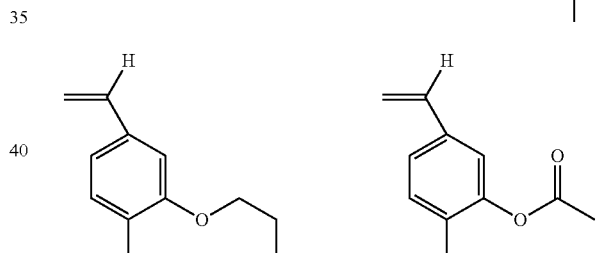
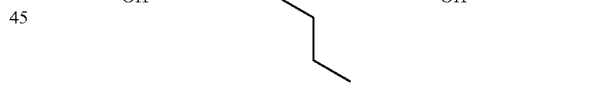
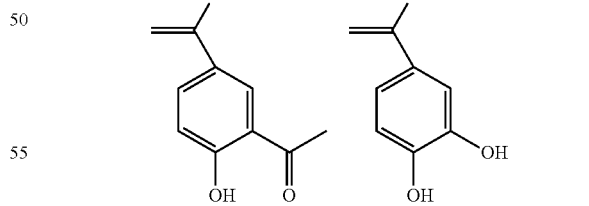
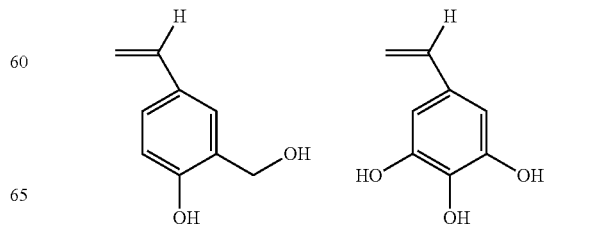

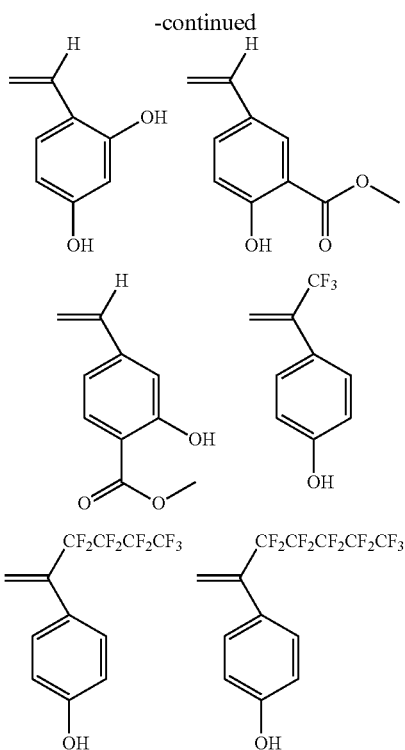

Among them, preferred are 4-hydroxystyrene and 4-hydroxy-α-methylstyrene.

When the resin contains the structural unit derived from the monomer represented by the formula (a2-0), the content of the structural unit derived from the monomer represented by the formula (a2-0) is usually 5 to 95% by mole and preferably 10 to 80% by mole and more preferably 15 to 80% by mole based on total molar of all the structural units of the resin.

In the formula (a2-1), $R^{a14}$ is preferably a methyl group. $R^{a15}$ is preferably a hydrogen atom, $R^{a16}$ is preferably a hydrogen atom or a hydroxyl group, $L^{a3}$ is preferably *—O— or *—O—$(CH_2)_{f2}$—CO—O— in which * represents a binding position to —CO—, and f2 represents an integer of 1 to 4, and is more preferably *—O—, and o1 is preferably 0, 1, 2 or 3 and is more preferably 0 or 1.

Examples of the monomer represented by the formula (a2-1) include the following.

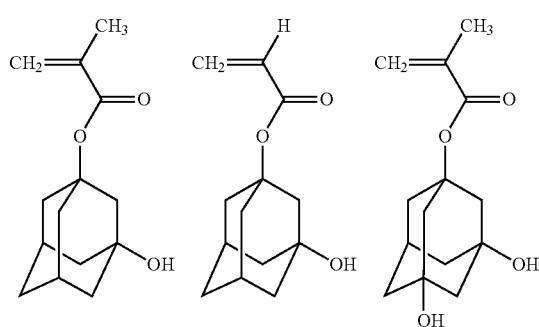

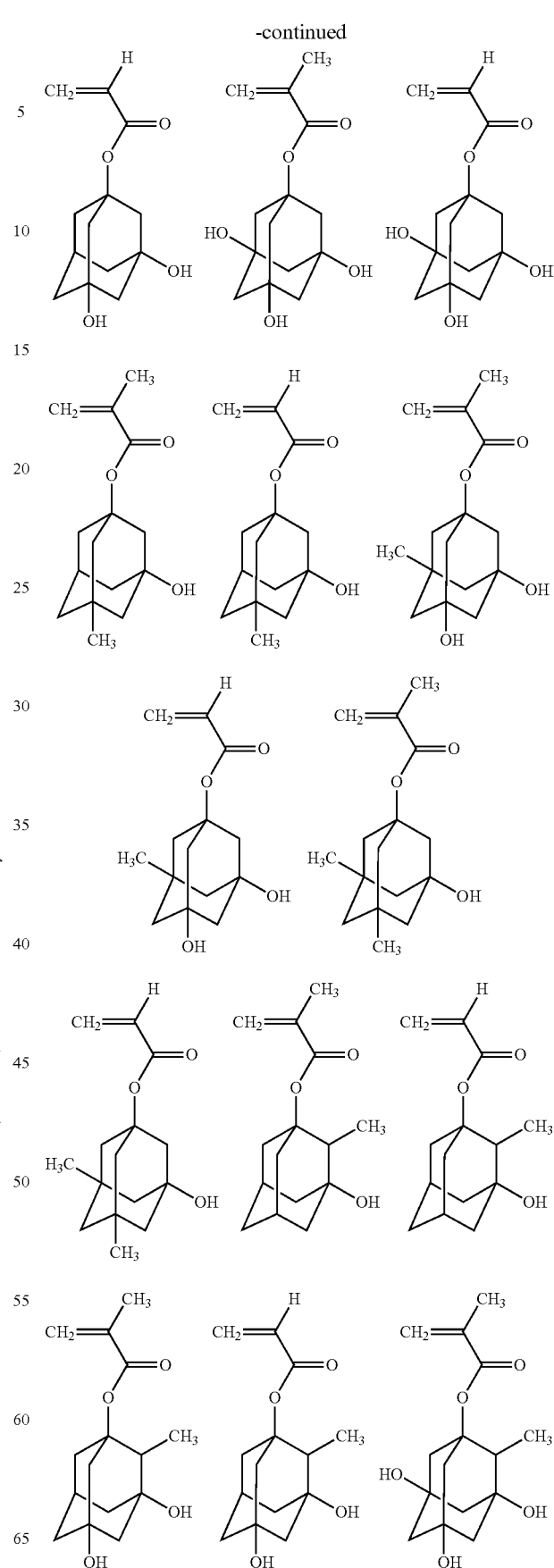

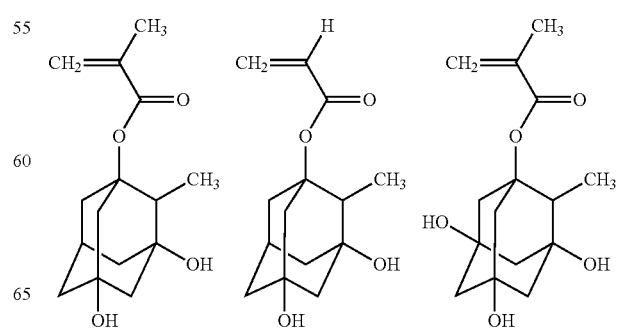

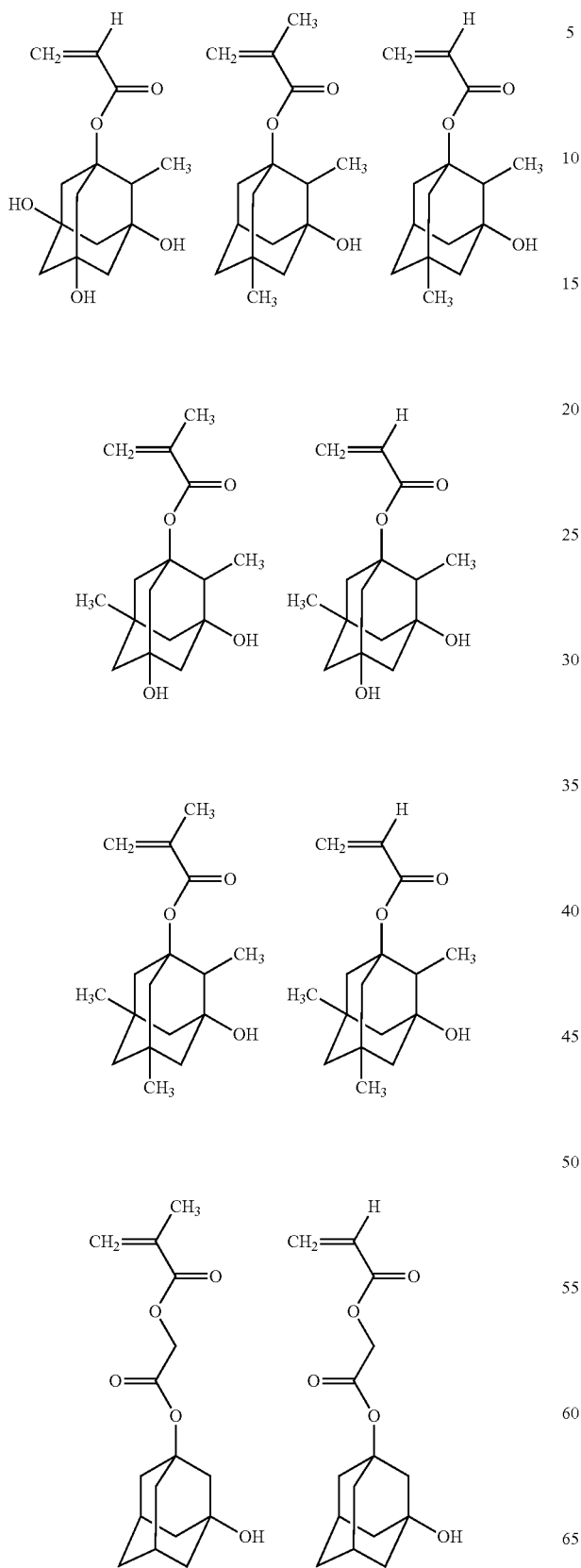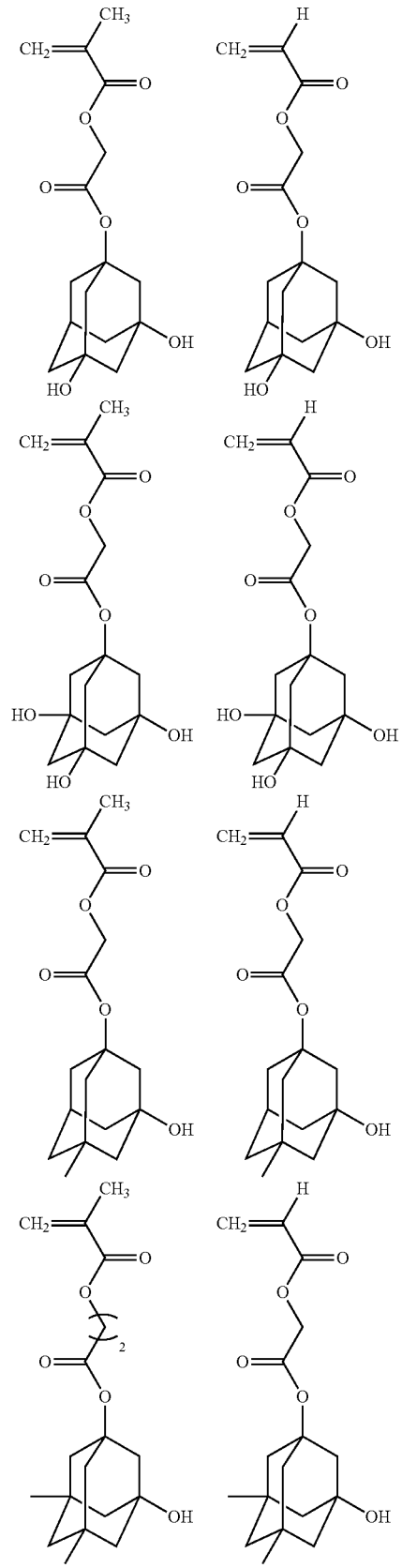

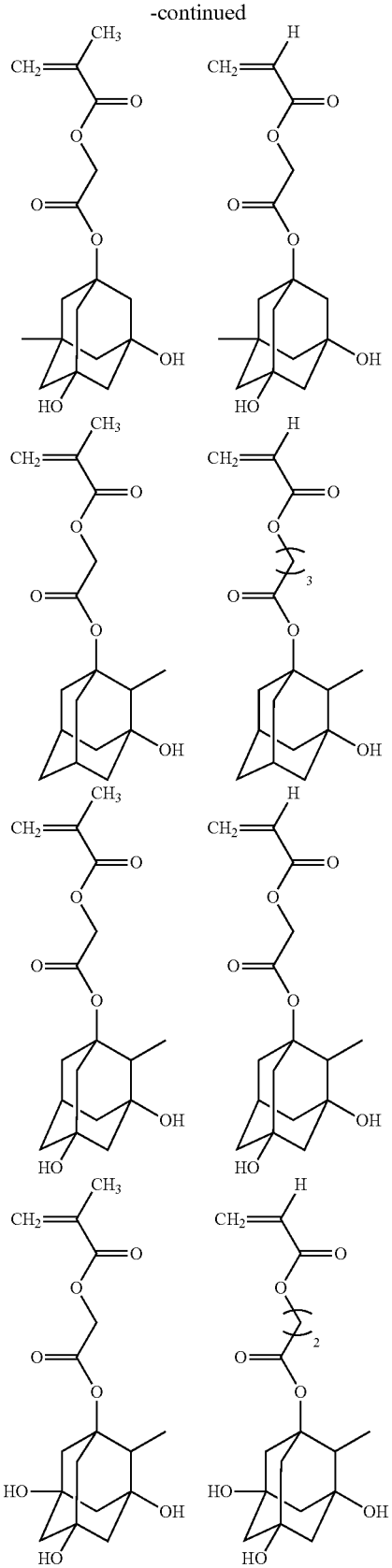

Among them, preferred are 3-hydroxy-1-adamantyl acrylate, 3-hydroxy-1-adamantyl methacrylate, 3,5-dihydroxy-1-adamantyl acrylate, 3,5-dihydroxy-1-adamantyl methacrylate, 1-(3,5-dihydroxy-1-adamantyloxycarbonyl)methyl acrylate and 1-(3,5-dihydroxy-1-adamantyloxycarbonyl)methyl methacrylate, and more preferred are 3-hydroxy-1-adamantyl methacrylate and 3,5-dihydroxy-1-adamantyl methacrylate.

When the resin contains the structural unit derived from the monomer represented by the formula (a2-1), the content of the structural unit derived from the monomer represented by the formula (a2-1) is usually 3 to 40% by mole based on total molar of all the structural units of the resin, and preferably 5 to 35% by mole, and more preferably 5 to 30% by mole, and especially preferably 5 to 20% by mole.

Examples of the lactone ring of the monomer having no acid-labile group and a lactone ring include a monocyclic lactone ring such as β-propiolactone ring, γ-butyrolactone ring and γ-valerolactone ring, and a condensed ring formed from a monocyclic lactone ring and the other ring. Among them, preferred are γ-butyrolactone ring and a condensed lactone ring formed from γ-butyrolactone ring and the other ring.

Preferable examples of the monomer having no acid-labile group and a lactone ring include the monomers represented by the formulae (a3-1), (a3-2) and (a3-3):

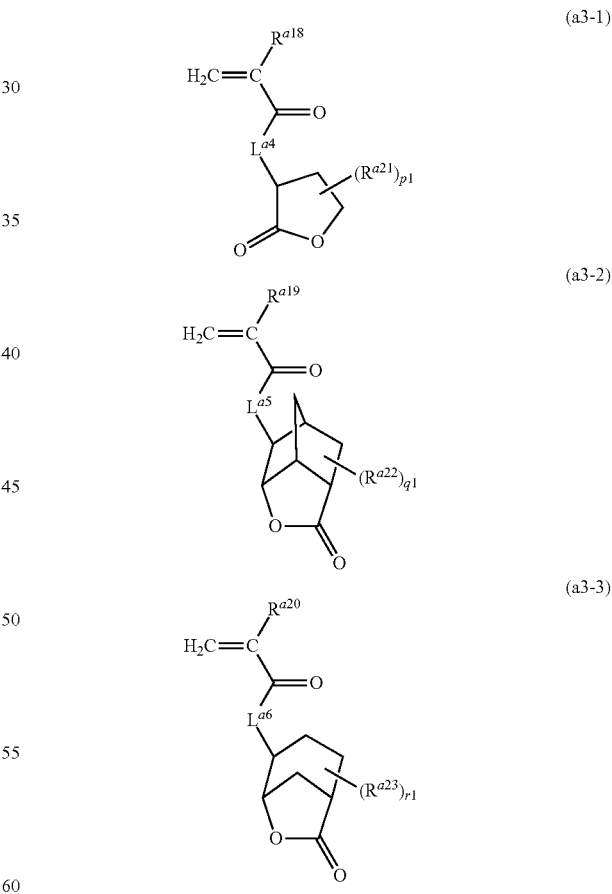

wherein $L^{a4}$, $L^{a5}$ and $L^{a6}$ each independently represent *—O— or —O—$(CH_2)_{k3}$—CO—O— in which * represents a binding position to —CO— and k3 represents an integer of 1 to 7, $R^{a18}$, $R^{a19}$ and $R^{a20}$ each independently represent a hydrogen atom or a methyl group, $R^{a21}$ represents a C1-C4 aliphatic hydrocarbon group, $R^{a22}$ and $R^{a23}$ are independently in each occurrence a carboxyl group, a cyano group or a C1-C4 aliphatic hydrocarbon group, and p1 represents an integer of 0 to 5, q1 and r1 independently each represent an integer of 0 to 3.

It is preferred that $L^{a4}$, $L^{a5}$ and $L^{a6}$ each independently represent —O— or *—O—$(CH_2)_{d1}$—CO—O— in which * represents a binding position to —CO— and d1 represents an integer of 1 to 4, and it is more preferred that $L^{a4}$, $L^{a5}$ and $L^{a6}$ are *—O—. $R^{a18}$, $R^{a19}$ and $R^{a20}$ are preferably methyl groups. $R^{a21}$ is preferably a methyl group. It is preferred that $R^{a22}$ and $R^{a23}$ are independently in each occurrence a carboxyl group, a cyano group or a methyl group. It is preferred that p1 is an integer of 0 to 2, and it is more preferred that p1 is 0 or 1. It is preferred that q1 and r1 independently each represent an integer of 0 to 2, and it is more preferred that q1 and r1 independently each represent 0 or 2.

Examples of the monomer represented by the formula (a3-1) include the following.

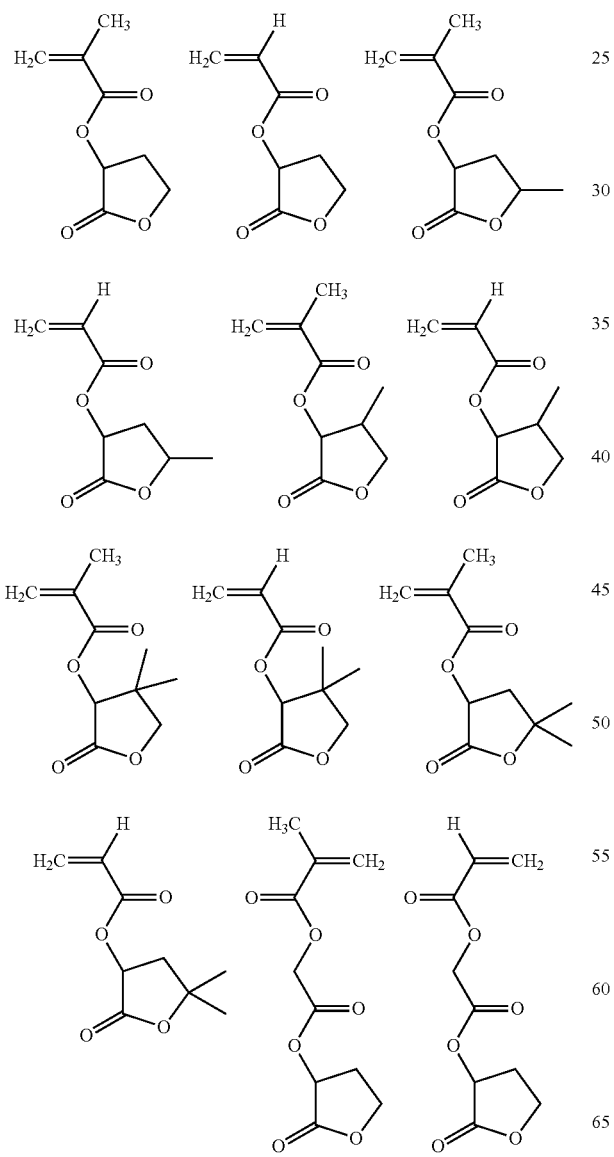
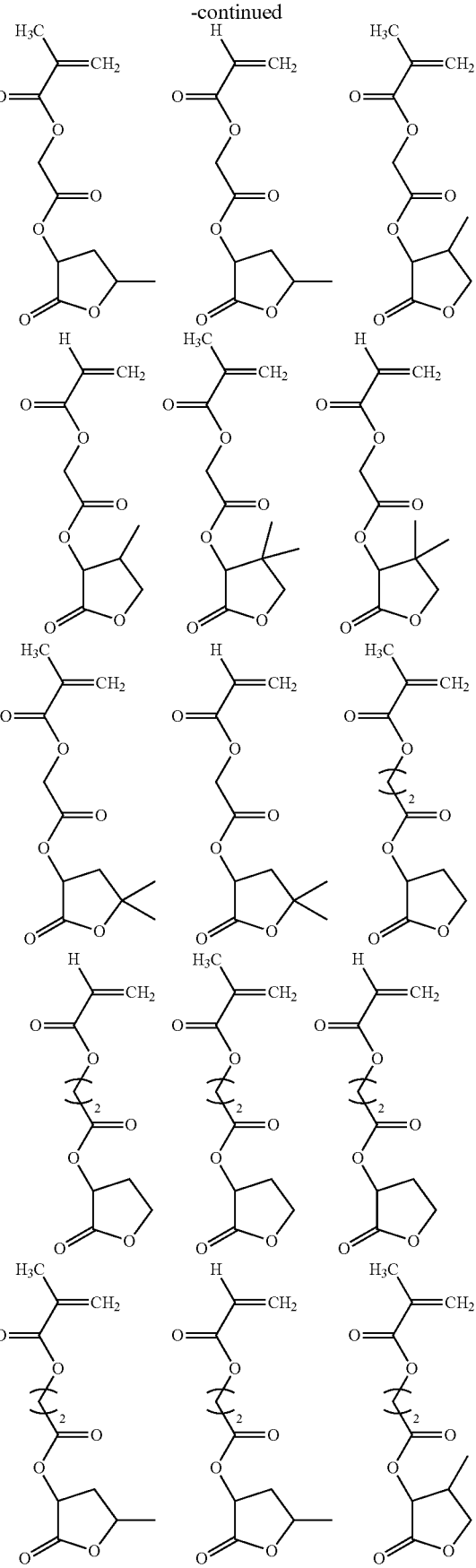

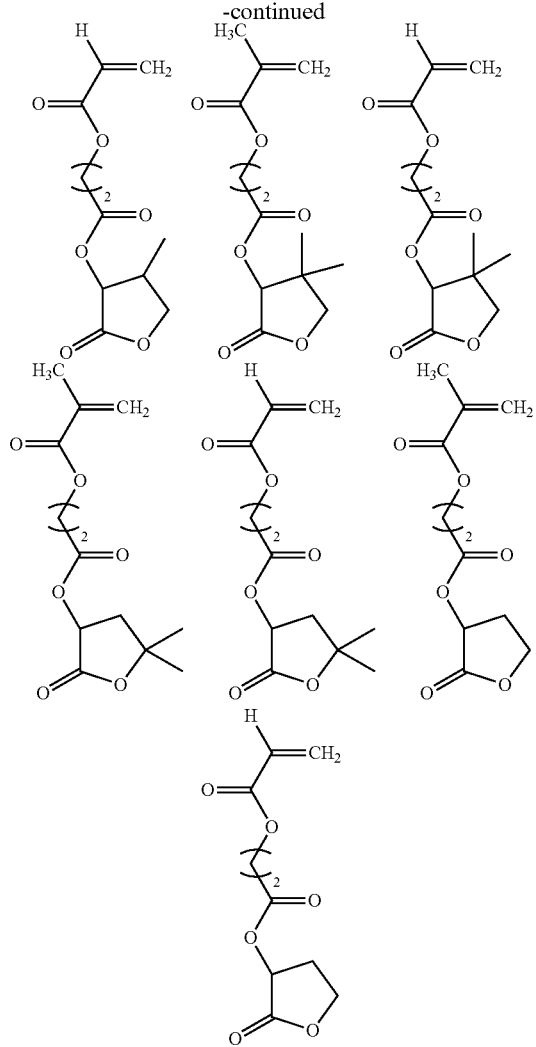
Examples of the monomer represented by the formula (a3-2) include the following.
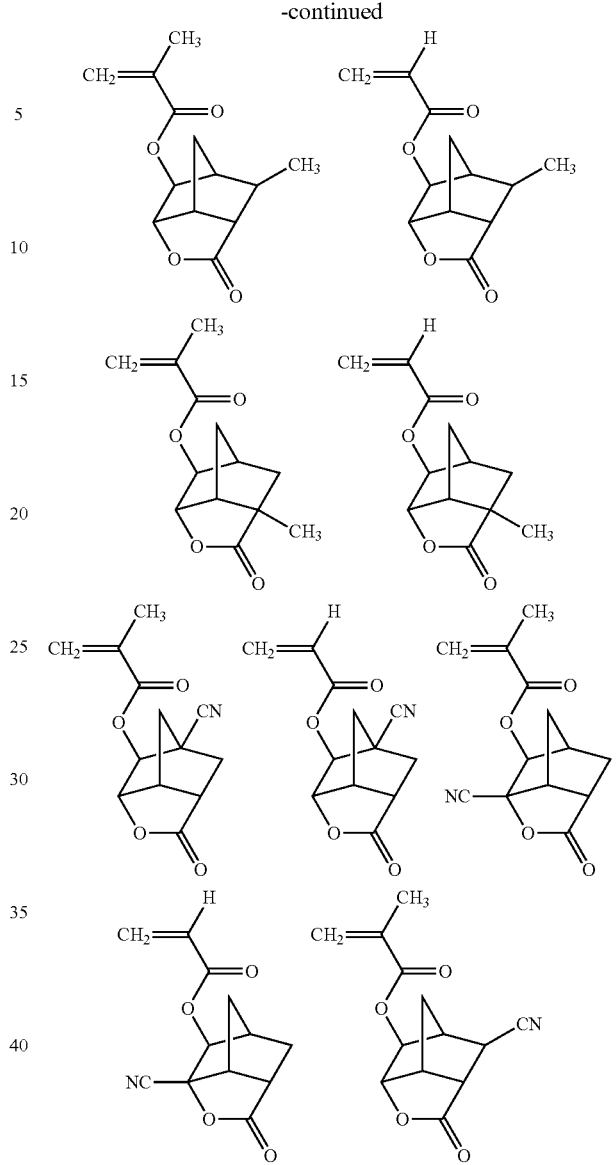
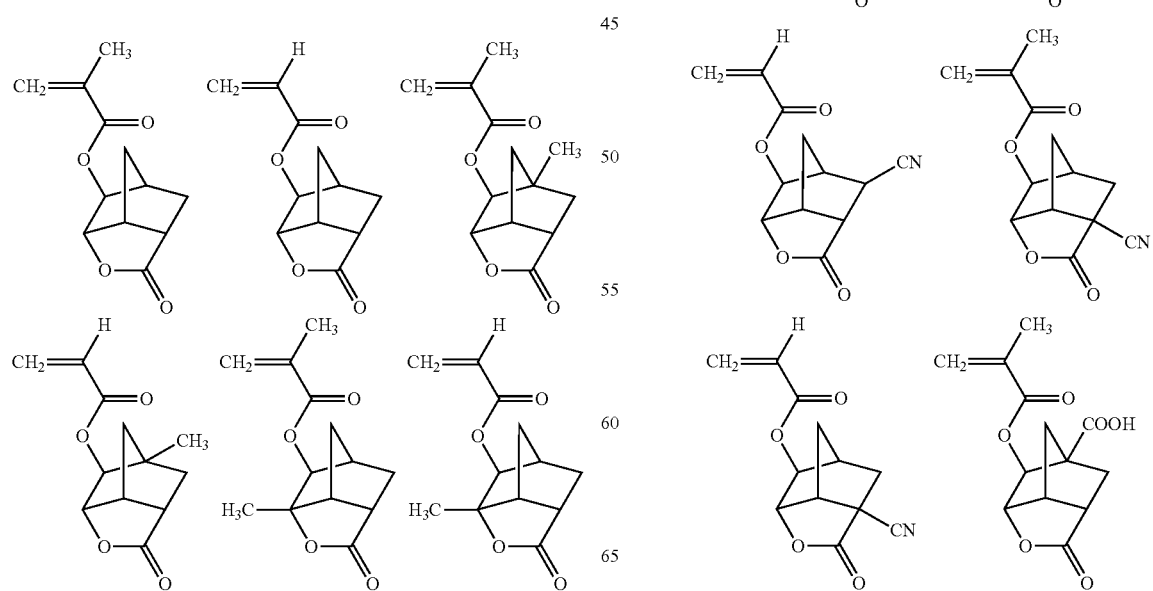

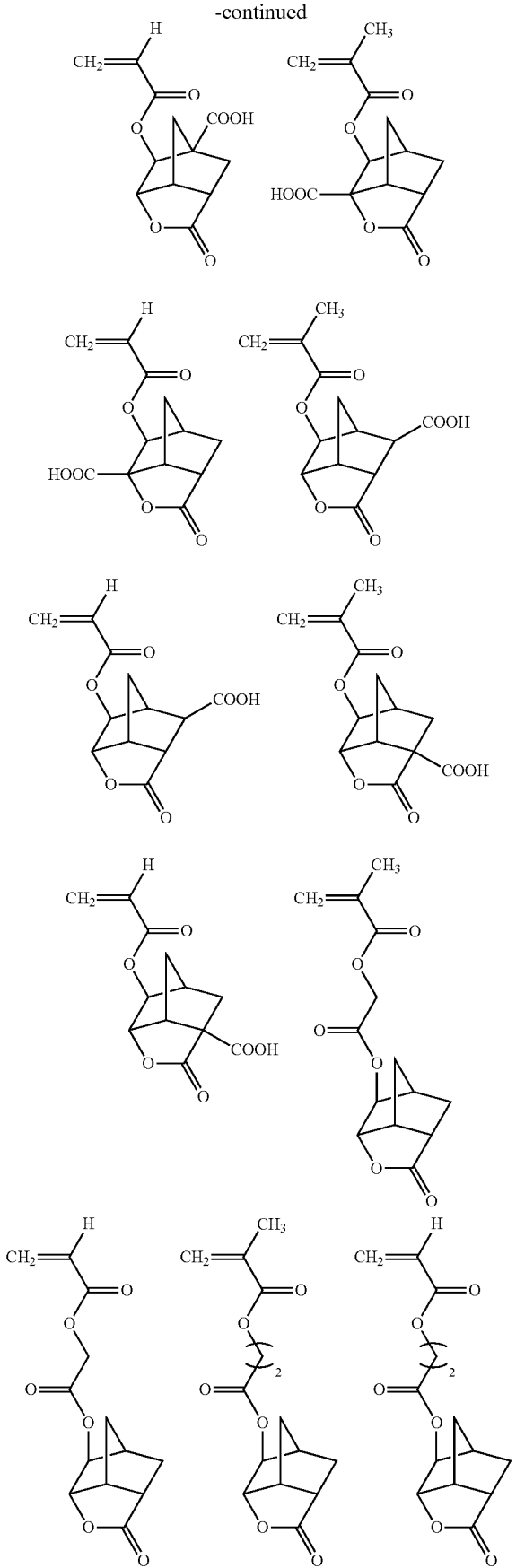
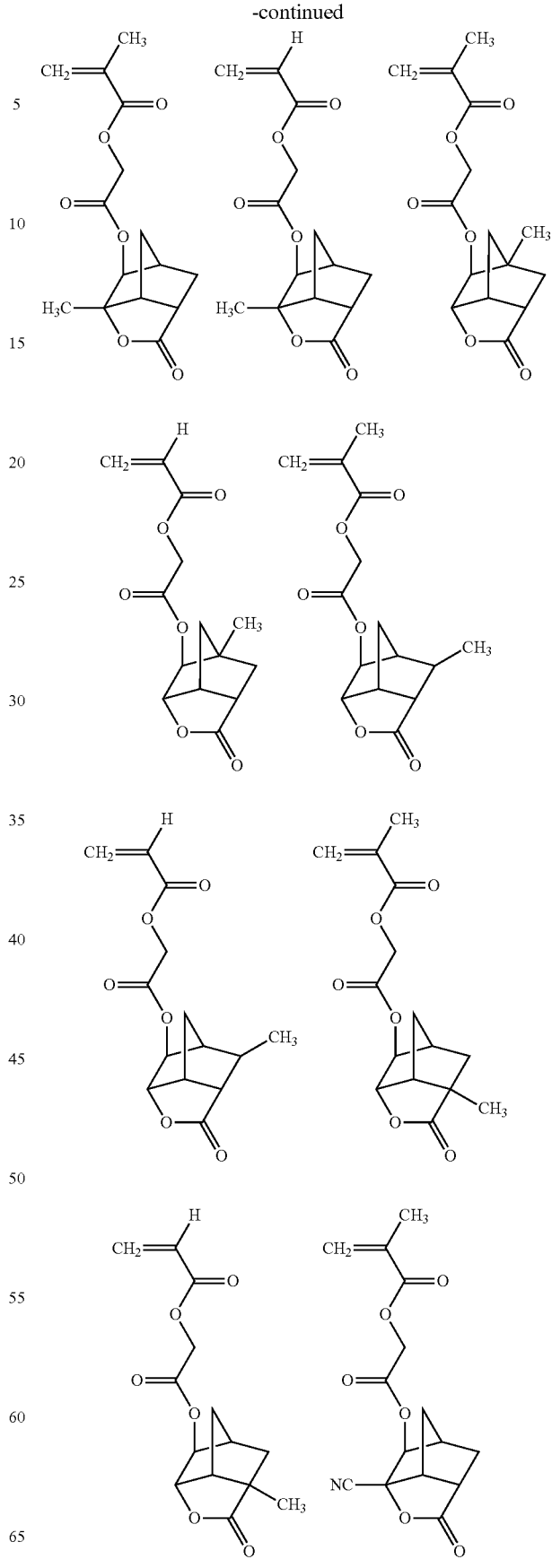

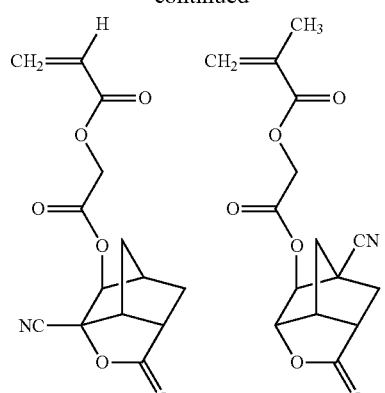
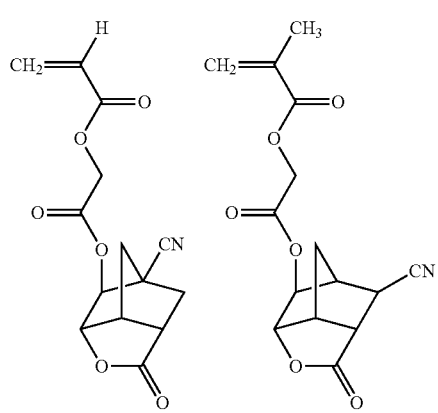
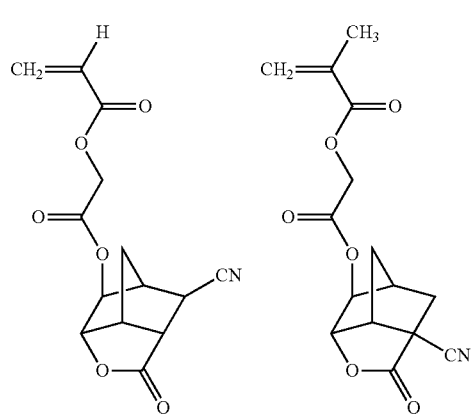
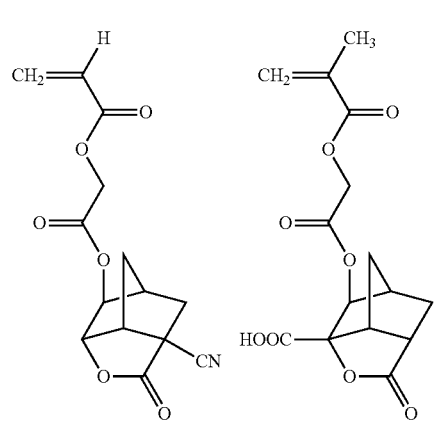
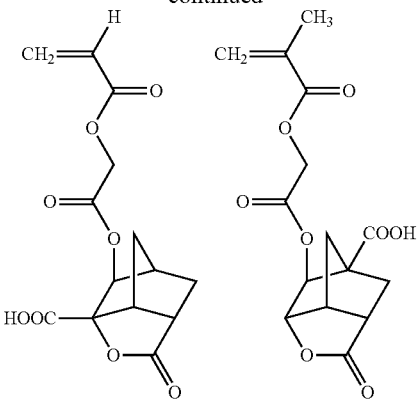
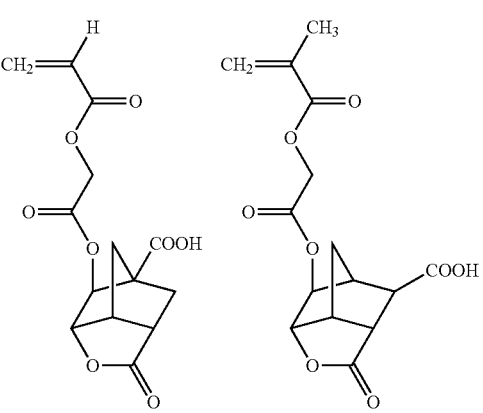
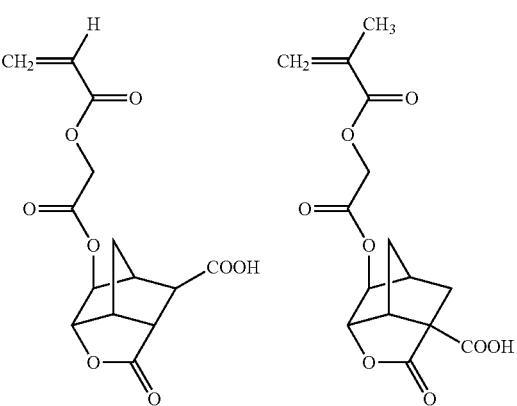
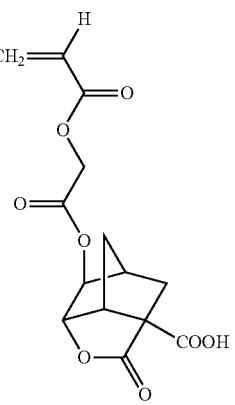
Examples of the monomer represented by the formula (a3-3) include the following.

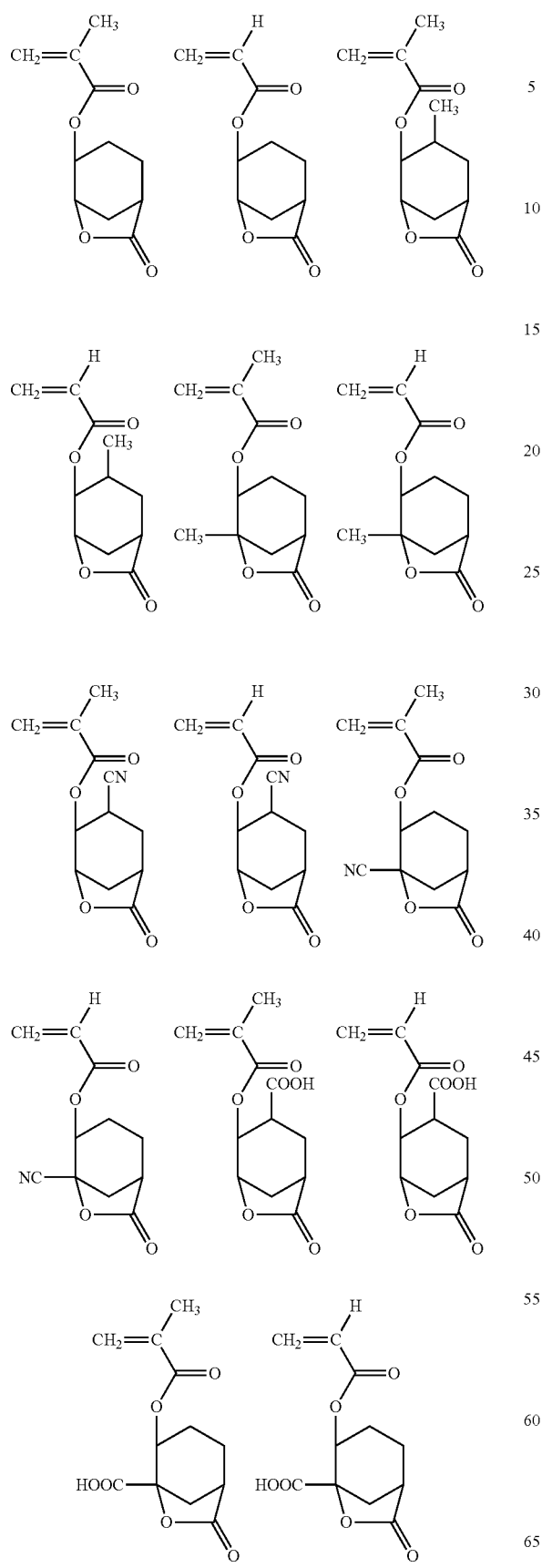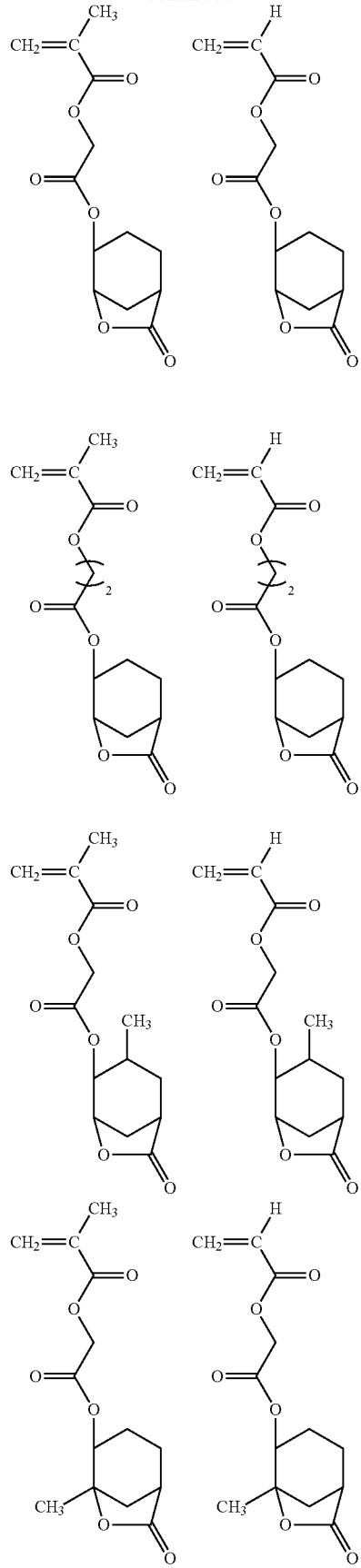

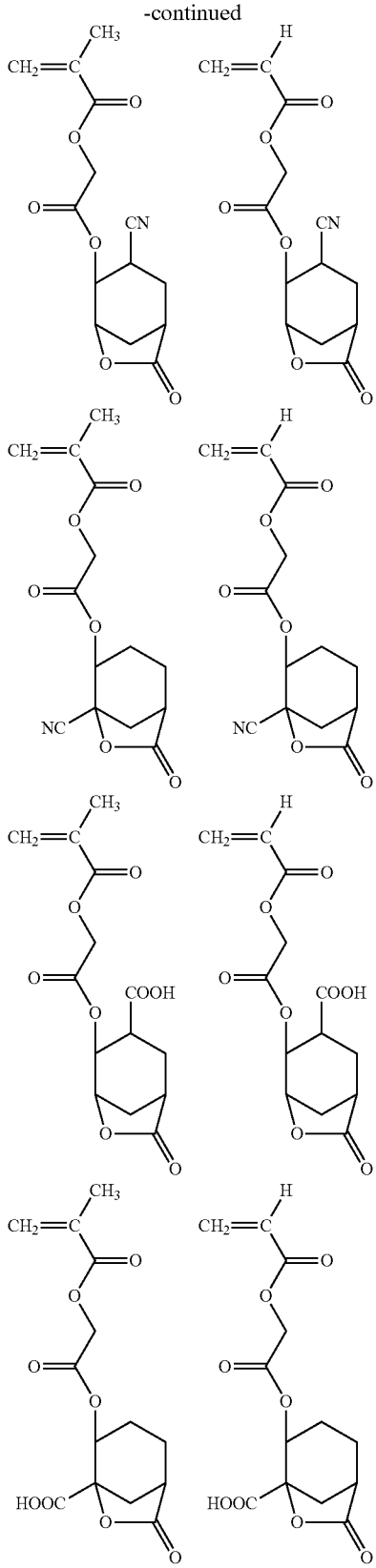

Among them, preferred are 5-oxo-4-oxatricyclo[4.2.1.0³,⁷]nonan-2-yl acrylate, 5-oxo-4-oxatricyclo[4.2.1.0³,⁷]nonan-2-yl methacrylate, tetrahydro-2-oxo-3-furyl acrylate, tetrahydro-2-oxo-3-furyl methacrylate, 2-(5-oxo-4-oxatricyclo[4.2.1.0³,⁷]nonan-2-yloxy)-2-oxoethyl acrylate and 2-(5-oxo-4-oxatricyclo[4.2.1.0³,⁷]nonan-2-yloxy)-2-oxoethyl methacrylate, and more preferred are 5-oxo-4-oxatricyclo[4.2.1.0³,⁷]nonan-2-yl methacrylate, tetrahydro-2-oxo-3-furyl methacrylate and 2-(5-oxo-4-oxatricyclo[4.2.1.0³,⁷]nonan-2-yloxy)-2-oxoethyl methacrylate.

When the resin contains the structural unit derived from the monomer having no acid-labile group and having a lactone ring, the content thereof is usually 5 to 60% by mole based on total molar of all the structural units of the resin, and preferably 5 to 50% by mole and more preferably 10 to 40% by mole and especially preferably 15 to 40% by mole.

When the resin contains the structural unit derived from the monomer represented by the formula (a3-1), (a3-2) or (a3-3), the content thereof is usually 5 to 60% by mole based on total molar of all the structural units of the resin, and preferably 10 to 55% by mole and more preferably 20 to 50% by mole.

Examples of the other monomer having no acid-labile group include the monomers represented by the formulae (a4-1), (a4-2) and (a4-3):

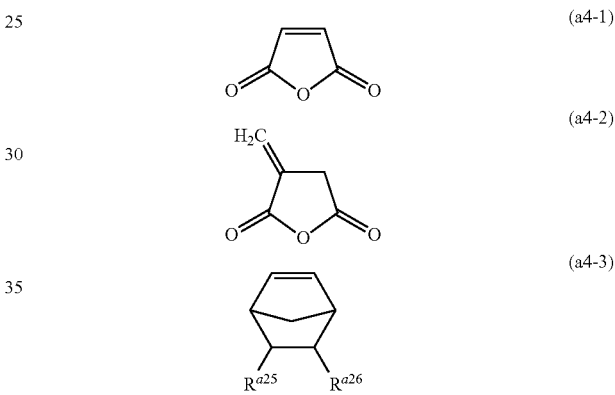

wherein $R^{a25}$ and $R^{a26}$ each independently represents a hydrogen atom, a C1-C3 aliphatic hydrocarbon group which can have one or more hydroxyl groups, a carboxyl group, a cyano group or a —COOR$^{a27}$ group in which R$^{a27}$ represents a C1-C18 aliphatic hydrocarbon group or a C3-C18 alicyclic hydrocarbon group, and one or more —CH$_2$— in the C1-C18 aliphatic hydrocarbon group and the C3-C18 alicyclic hydrocarbon group can be replaced by —O— or —CO—, with the proviso that the carbon atom bonded to —O— of —COO— of $R^{a27}$ is not a tertiary carbon atom, or $R^{a25}$ and $R^{a26}$ are bonded together to form a carboxylic anhydride residue represented by —C(=O)—O—C(=O)—.

Examples of the substituent of the C1-C3 aliphatic hydrocarbon group include a hydroxyl group. Examples of the C1-C3 aliphatic hydrocarbon group which can have one or more hydroxyl groups include a C1-C3 alkyl group such as a methyl group, an ethyl group and a propyl group, and a C1-C3 hydroxyalkyl group such a hydroxymethyl group and a 2-hydroxyethyl group. The C1-C18 aliphatic hydrocarbon group represented by R$^{a27}$ is preferably a C1-C8 aliphatic hydrocarbon group and is more preferably a C1-C6 aliphatic hydrocarbon group. The C3-C18 alicyclic hydrocarbon group represented by R$^{a27}$ is preferably a C4-C18 alicyclic hydrocarbon group, and is more preferably C4-C12 alicyclic hydrocarbon group. Examples of R$^{a27}$ include a methyl group, an ethyl group, a propyl group, a 2-oxo-oxolan-3-yl group and a 2-oxo-oxolan-4-yl group.

Examples of the monomer represented by the formula (a4-3) include 2-norbornene, 2-hydroxy-5-norbornene, 5-norbornene-2-carboxylic acid, methyl 5-norbornene-2-carboxylate, 2-hydroxyethyl 5-norbornene-2-carboxylate, 5-norbornene-2-methanol and 5-norbornene-2,3-dicarboxylic anhydride.

When the resin contains a structural unit derived from a monomer represented by the formula (a4-1), (a4-2) or (a4-3), the content thereof is usually 2 to 40% by mole and preferably 3 to 30% by mole and more preferably 5 to 20% by mole based on total molar of all the structural units of the resin.

Examples of the other monomer having no acid-labile group include a monomer represented by the formula (a4-4):

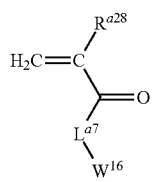
(a4-4)

wherein $R^{a28}$ represents a hydrogen atom or a methyl group, $L^{a7}$ represents —O— or *—O—$(CH_2)_{k2}$—CO—O— in which * represents a binding position to —CO— and k2 represents an integer of 1 to 7, and $W^{16}$ represents a group containing a sultone ring which may have one or more substituents.

Examples of the sultone ring include the following.

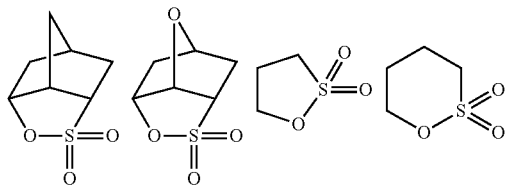

Examples of the group containing a sultone ring include groups formed by removing any one hydrogen atom from the above-mentioned sultone ring. Examples of the substituents include a hydroxyl group, a cyano group, a C1-C6 alkyl group, a C1-C6 fluorinated alkyl group, a C1-C6 hydroxyalkyl group, a C1-C6 alkoxy group, a C2-C7 alkoxycarbonyl group, a C2-C8 acyl group and a C2-C7 acyloxy group.

Examples of the fluorinated alkyl group include a difluoromethyl group, a trifluoromethyl group, a 1,1-difluoroethyl group, a 2,2-difluoroethyl group, a 2,2,2-trifluoroethyl group, a perfluoroethyl group, a 1,1,2,2-tetrafluoropropyl group, a 1,1,2,2,3,3-hexafluoropropyl group, a (perfluoroethyl)methyl group, a 1-(trifluoromethyl)-1,2,2,2-tetrafluoroethyl group, a perfluoropropyl group, a 1,1,2,2-tetrafluorobutyl group, a 1,1,2,2,3,3-hexafluorobutyl group, a 1,1,2,2,3,3,4,4-octafluorobutyl group, a perfluorobutyl group, a 1,1-bis(trifluoromethyl)-2,2,2-trifluoroethyl group, 2-(perfluoropropyl)ethyl group, a 1,1,2,2,3,3,4,4-octafluoropentyl group, a perfluoropentyl group, a 1,1,2,2,3,3,4,4,5,5-decafluoropentyl group, a 1,1-bis(trifluoromethyl)-2,2,3,3,3,-pentafluoropropyl group, a perfluoropentyl group, a 2-(perfluorobutyl)ethyl group, a 1,1,2,2,3,3,4,4,5,5-decafluorohexyl group, a 1,1,2,2, 3,3,4,4,5,5,6,6-dodecafluorohexyl group, a (perfluoropentyl)methyl group and a perfluorohexyl groups. Among them preferred is a C1-C4 fluorinated alkyl group, and more preferred are a trifluoromethyl group, a perfluoroethyl group and a perfluoropropyl group, and especially preferred is a trifluoromethyl group.

Examples of the hydroxyalkyl group include a hydroxymethyl group and a 2-hydroxyethyl group.

Examples of the monomer represented by the formula (a4-4), include the following.

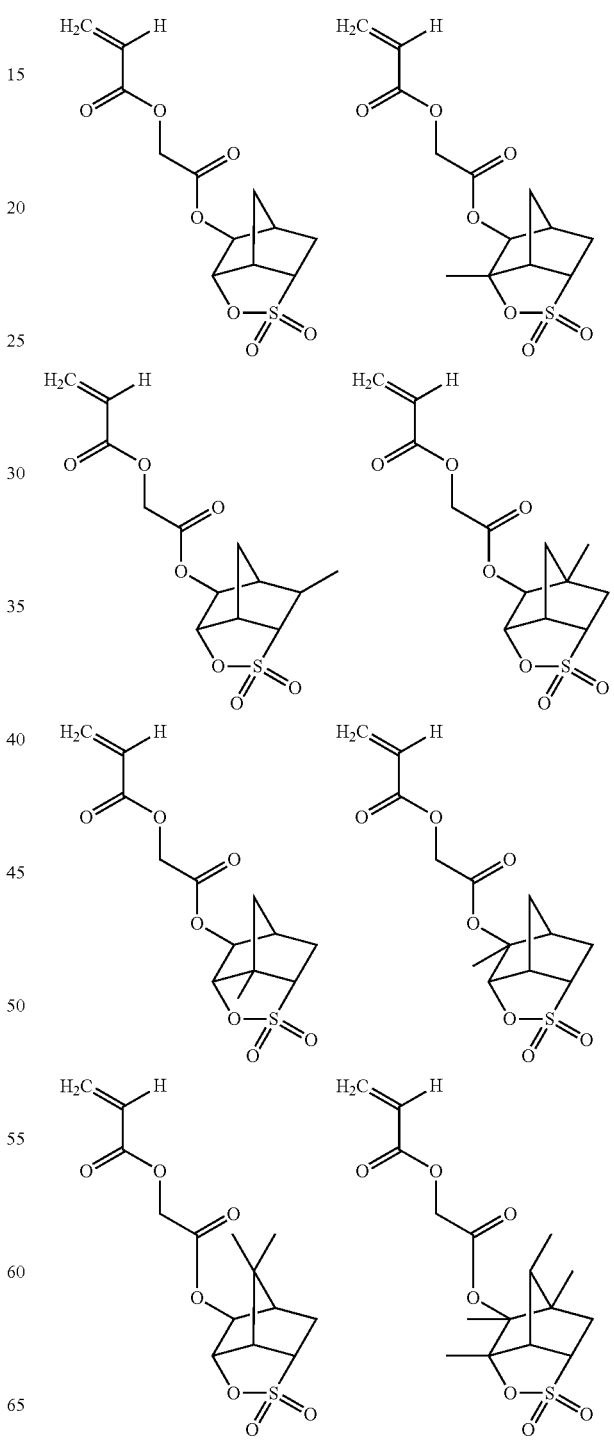

109
-continued
110
-continued
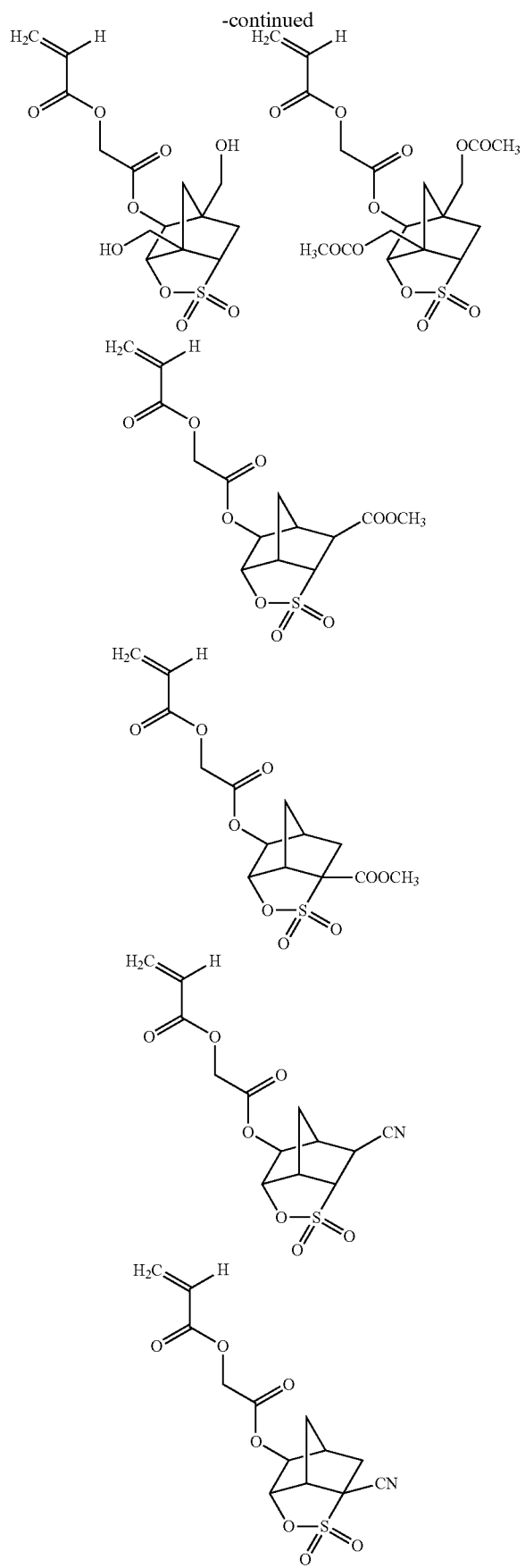
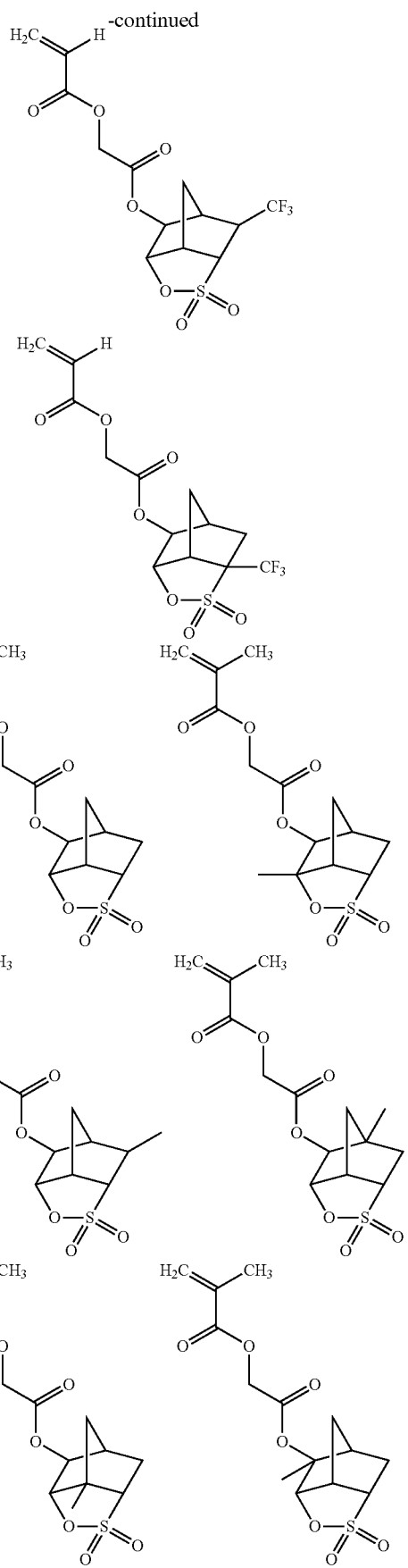

111
-continued
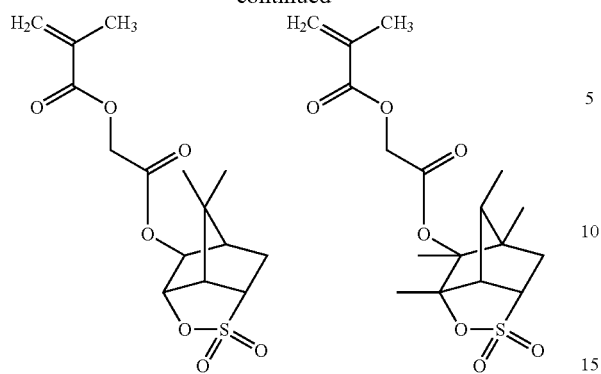
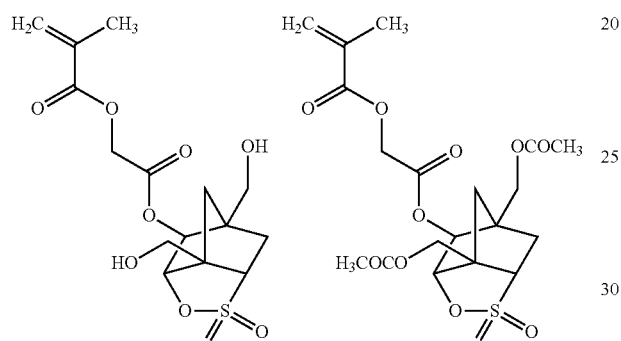
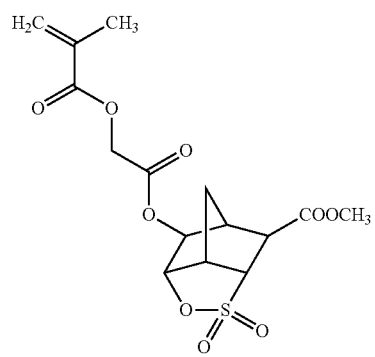
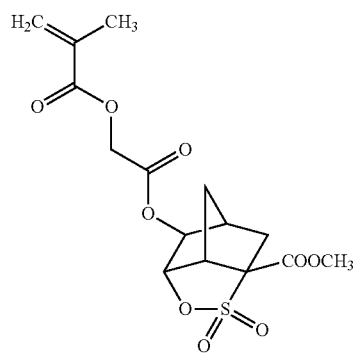
112
-continued
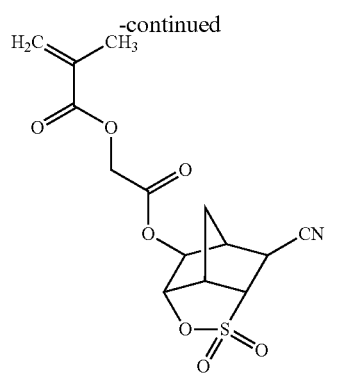
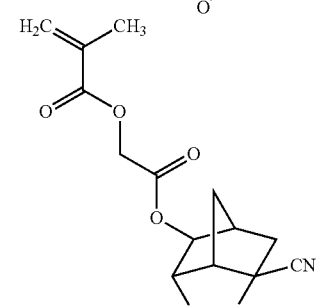
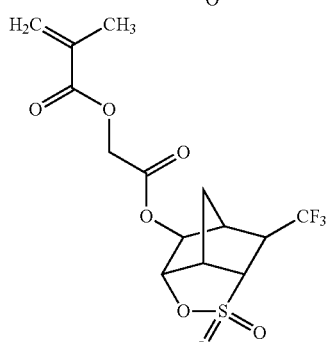
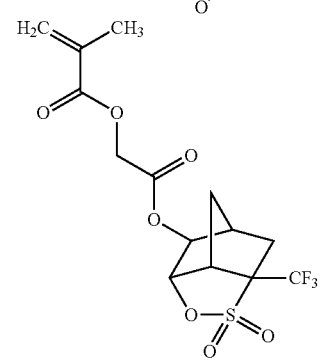
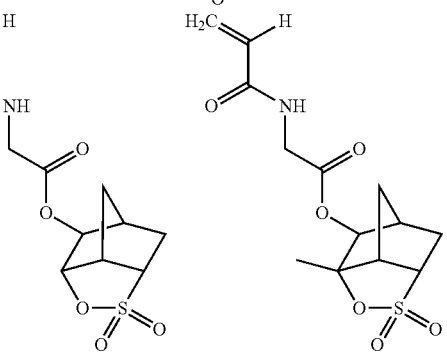

113
-continued
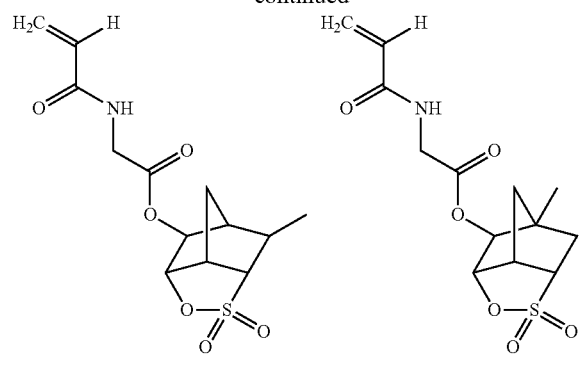
114
-continued
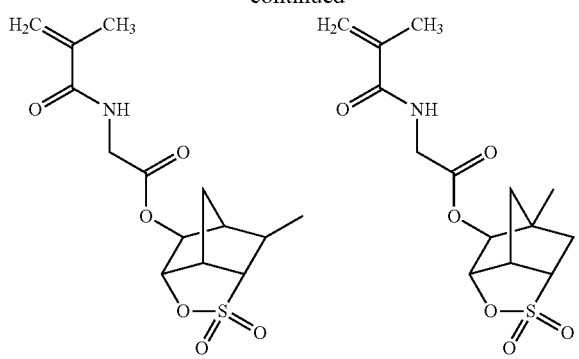
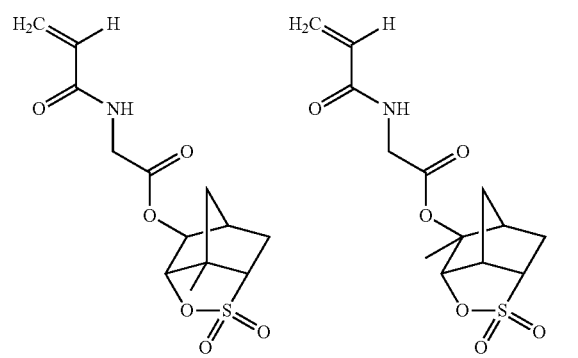
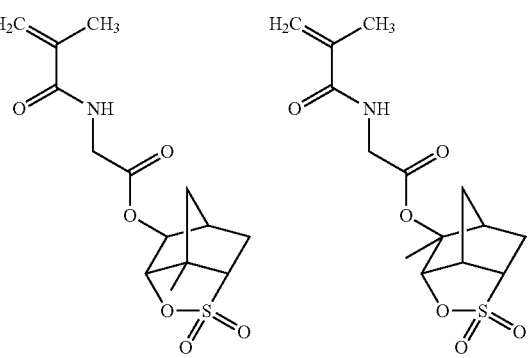
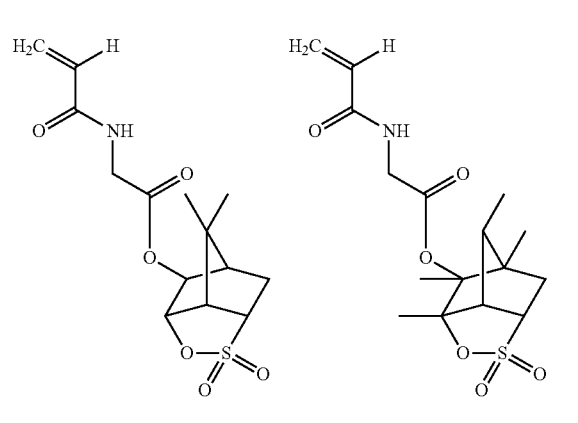
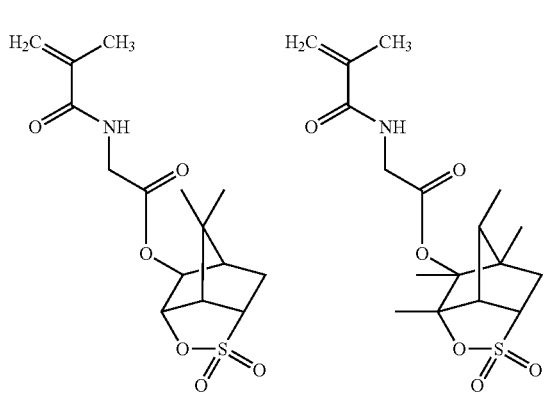
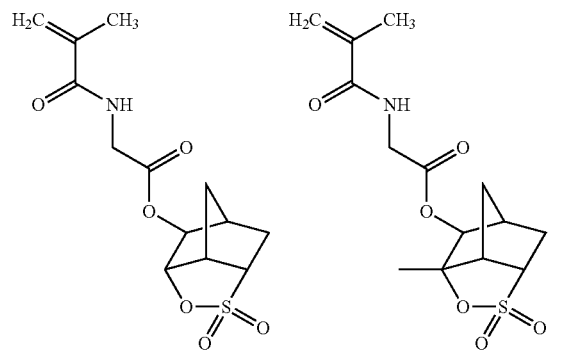
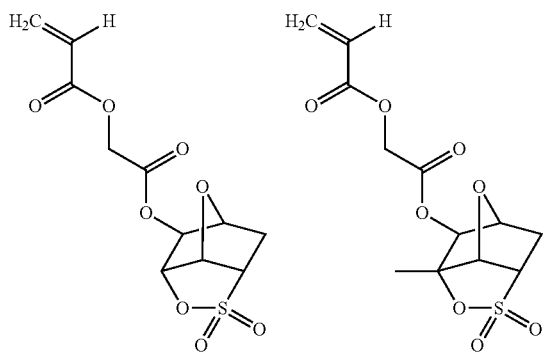

115
-continued
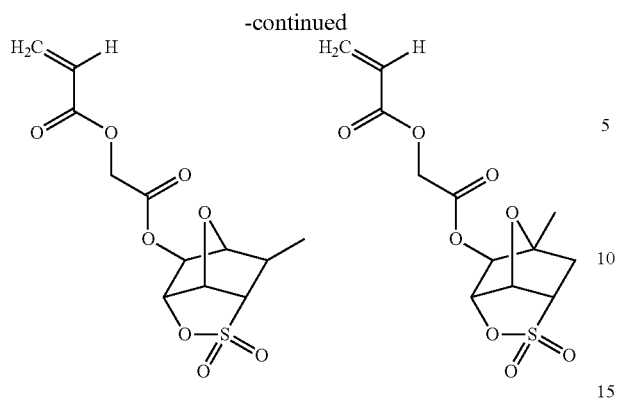
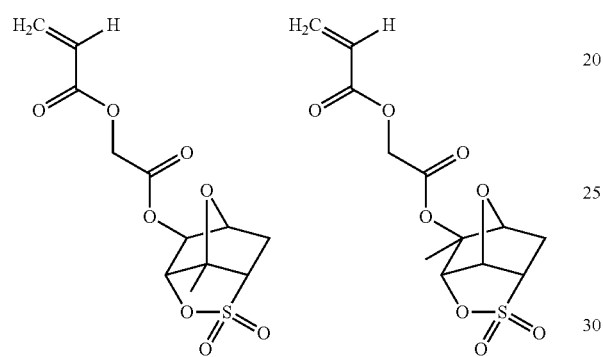
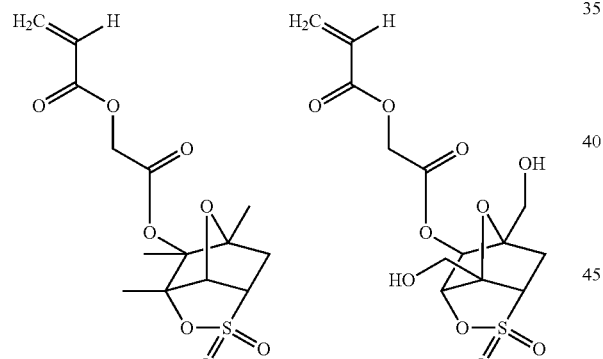
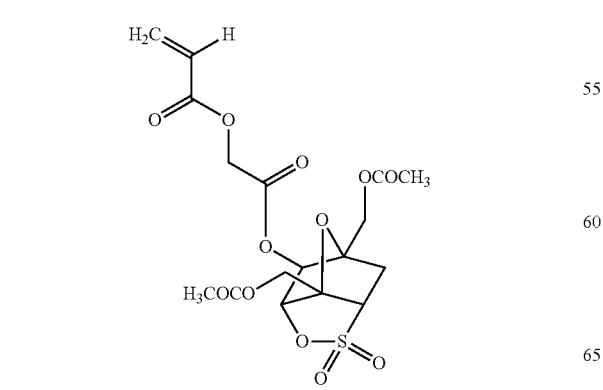
116
-continued
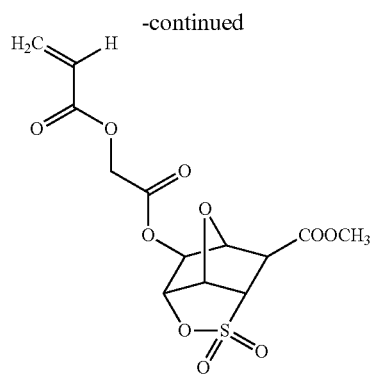
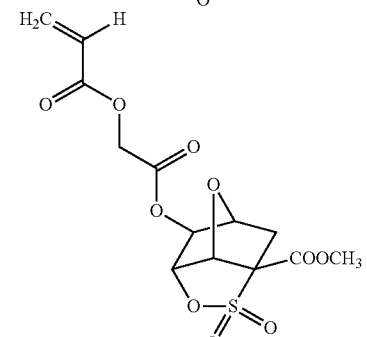
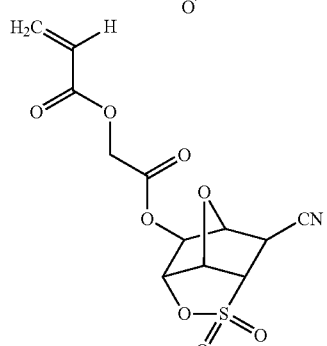
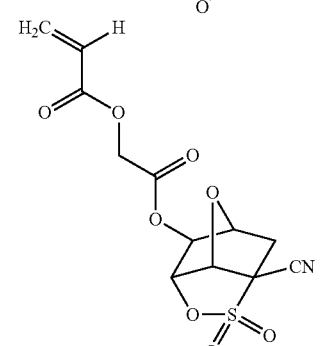
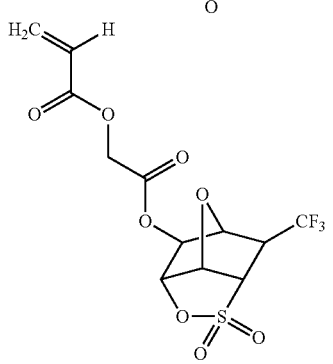

117
-continued
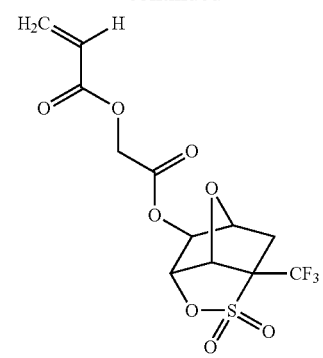
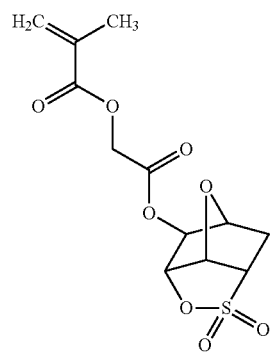 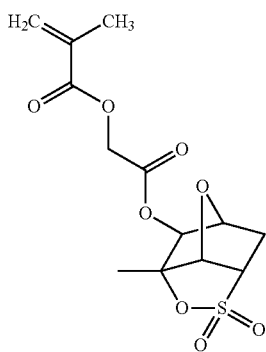
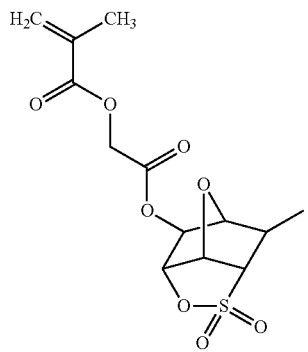 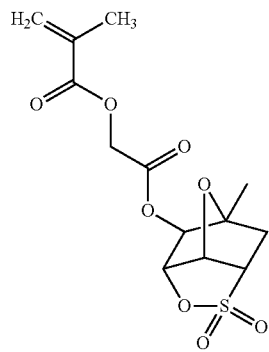
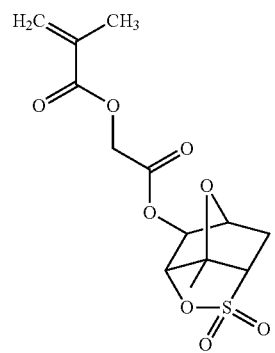 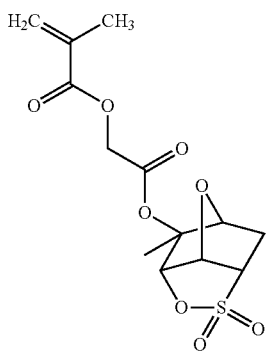
118
-continued
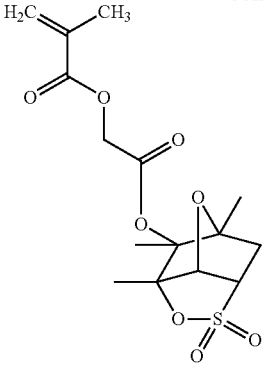 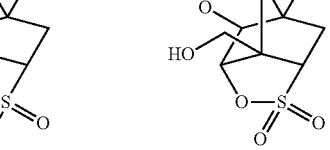
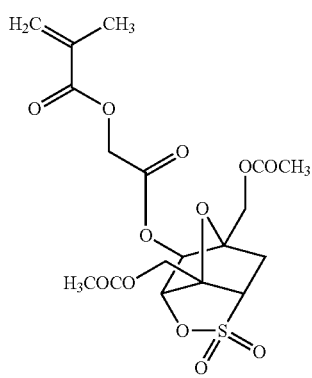
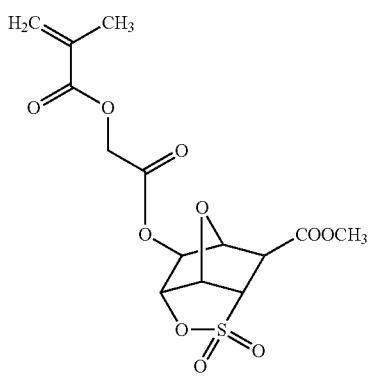
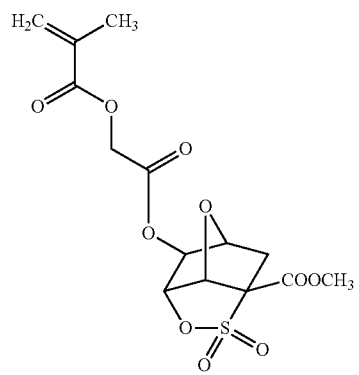

119
-continued
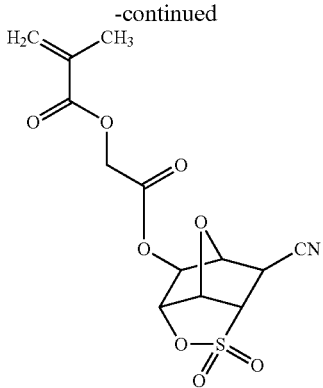
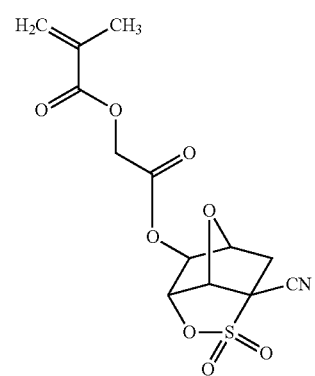
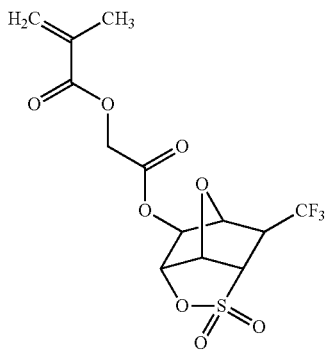
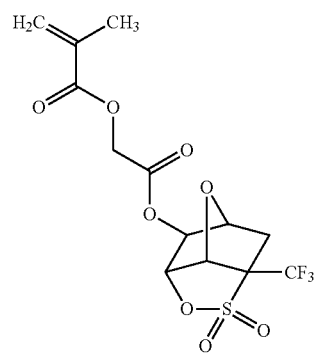
120
-continued
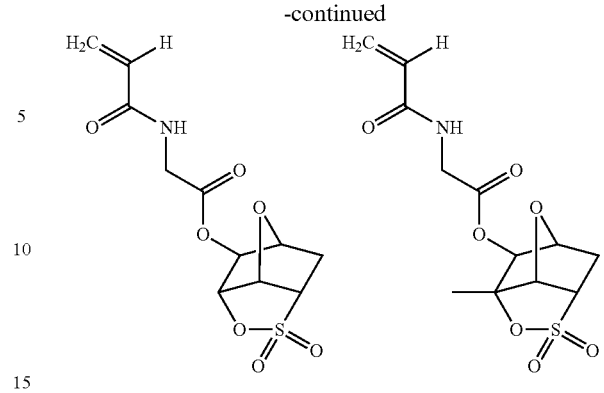
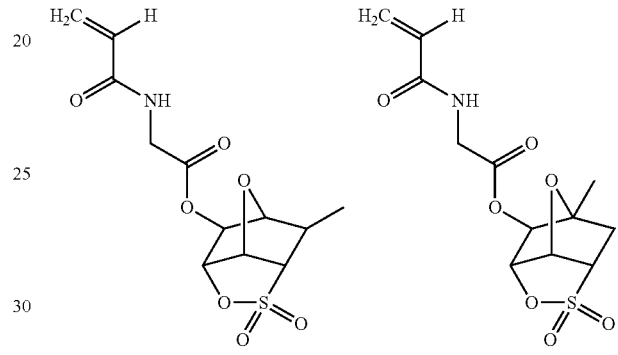
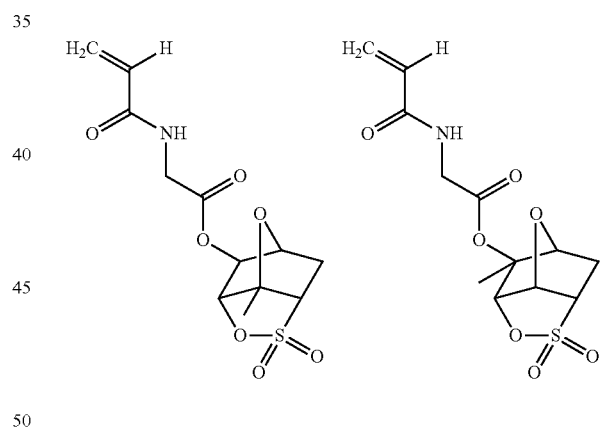
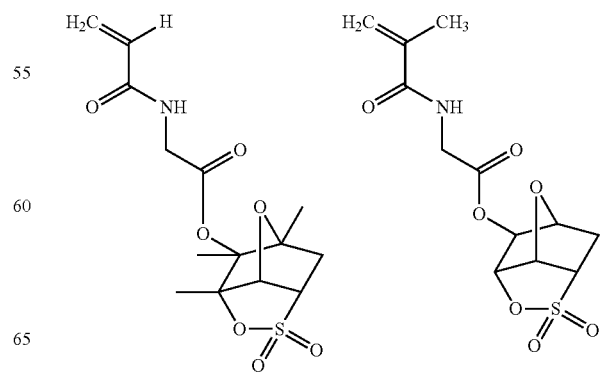

121
-continued
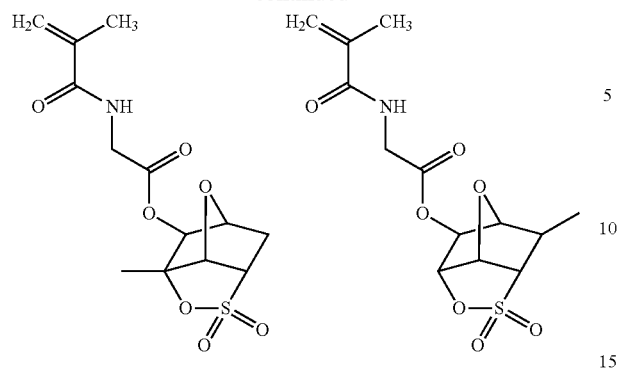
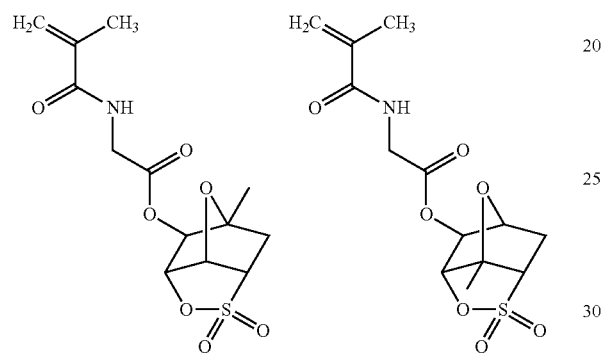
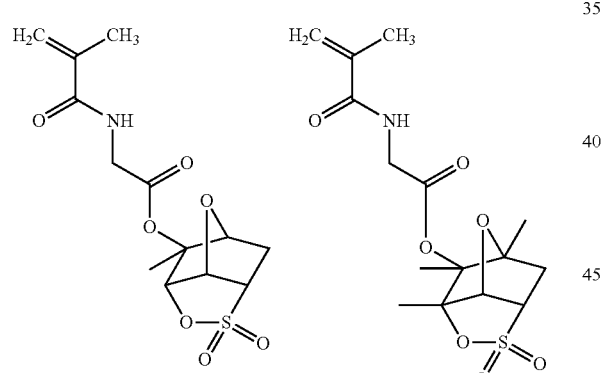
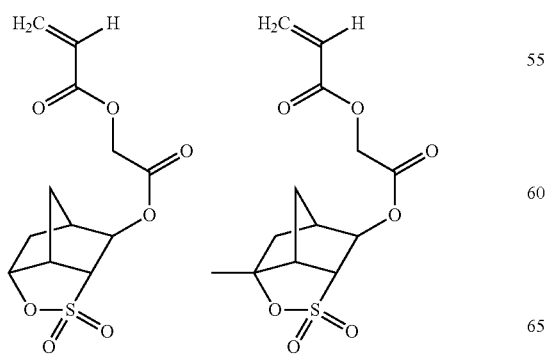
122
-continued
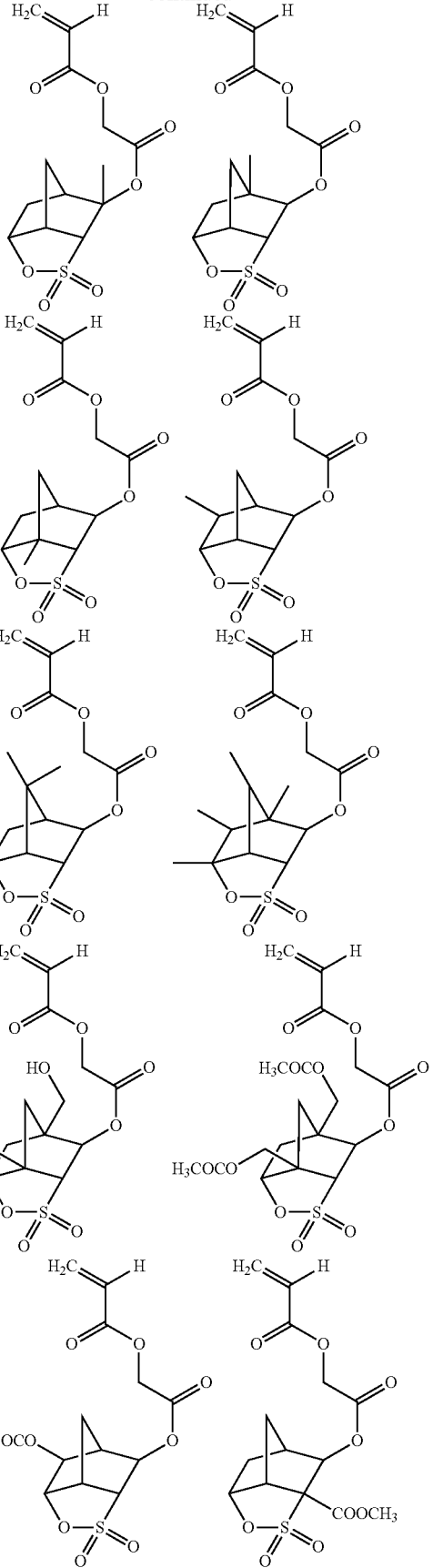

123
-continued
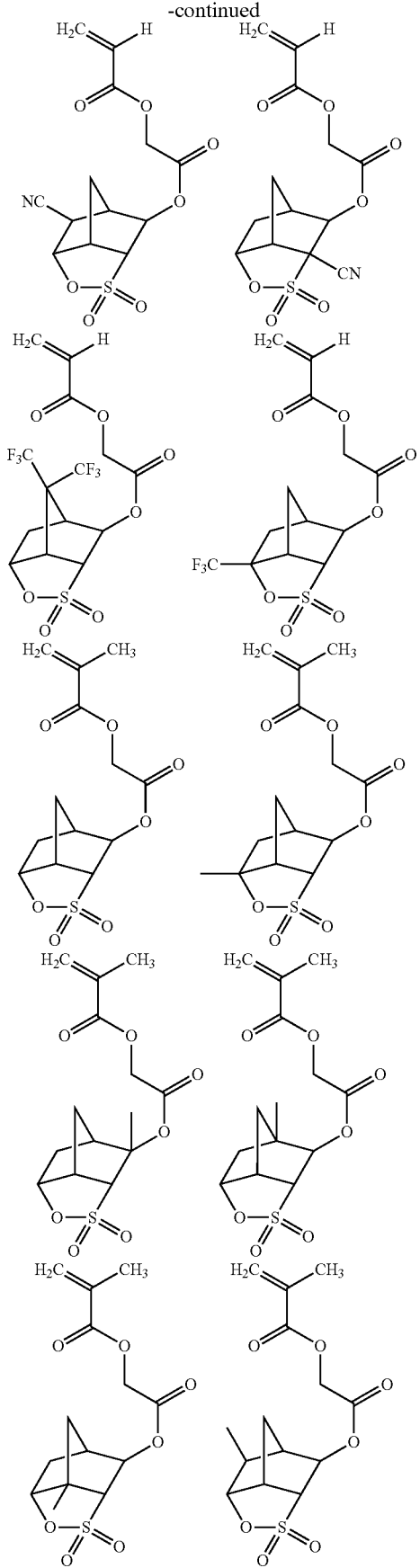
124
-continued
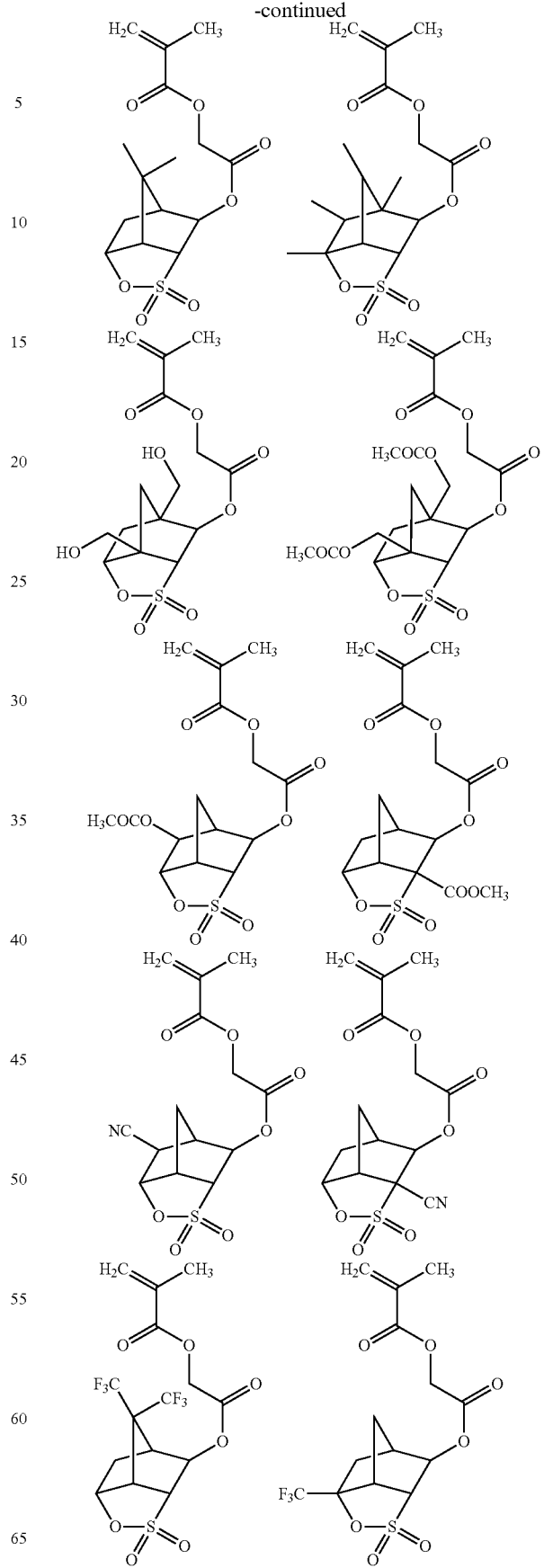

125
-continued
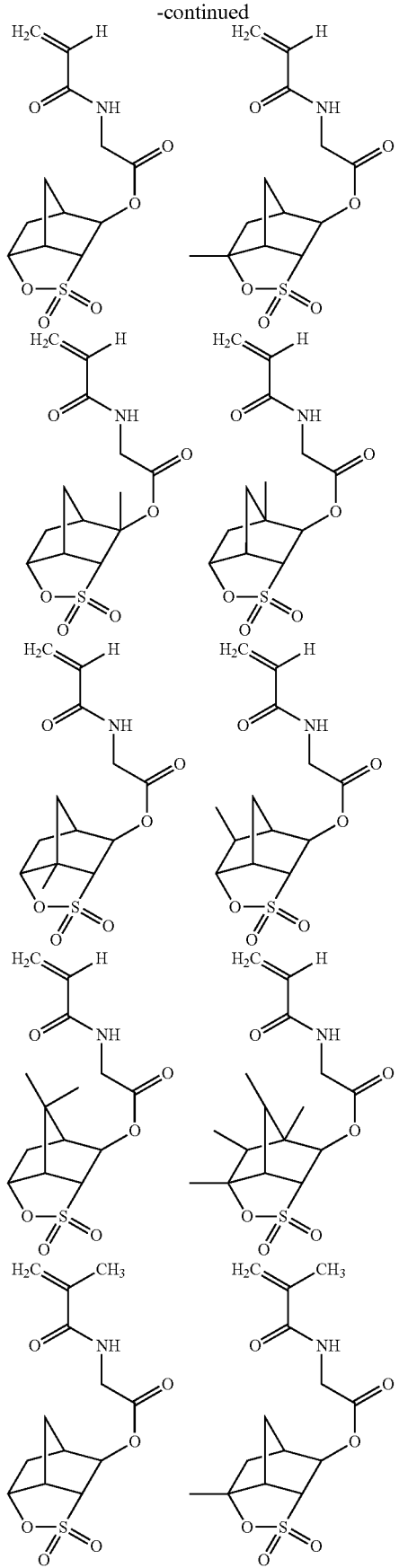
126
-continued
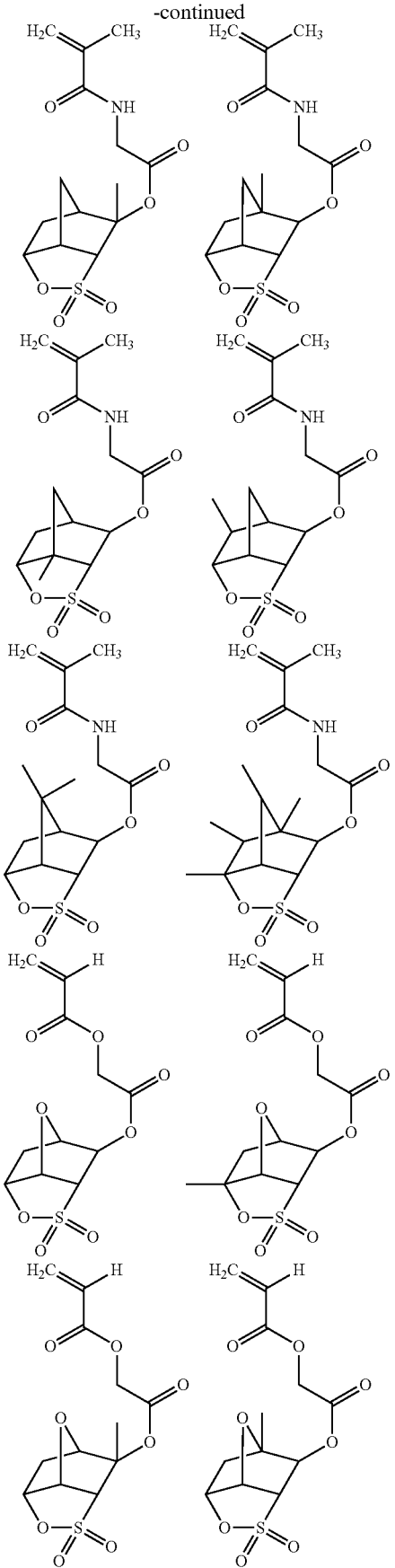

127
-continued
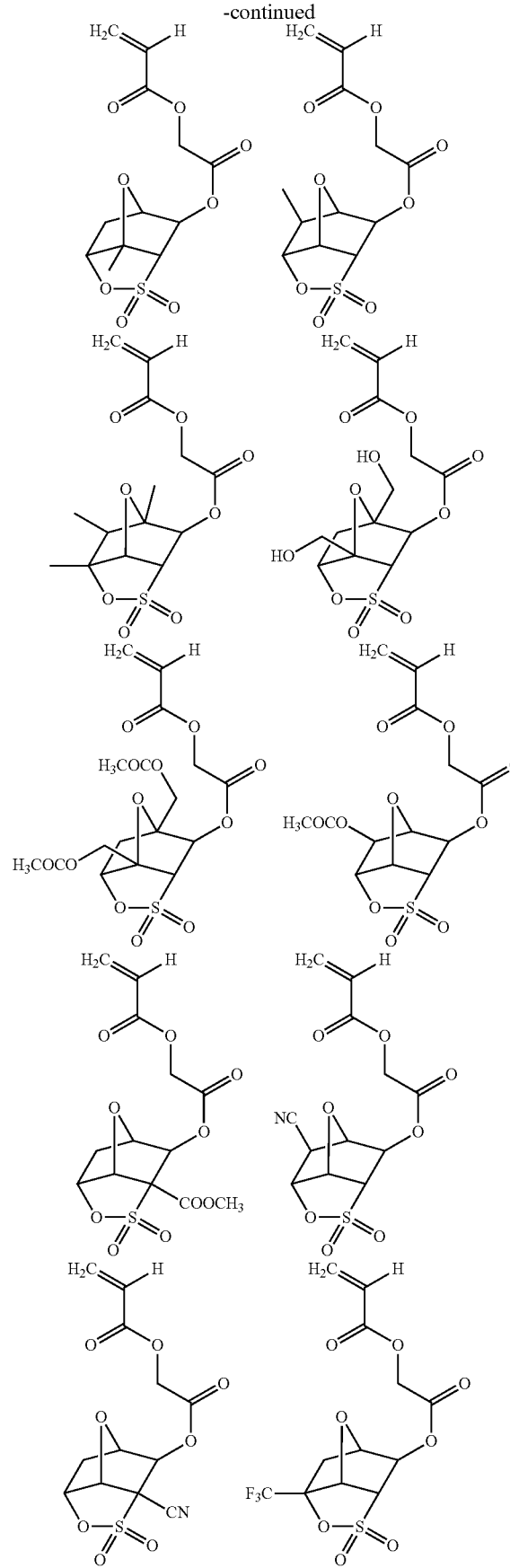
128
-continued
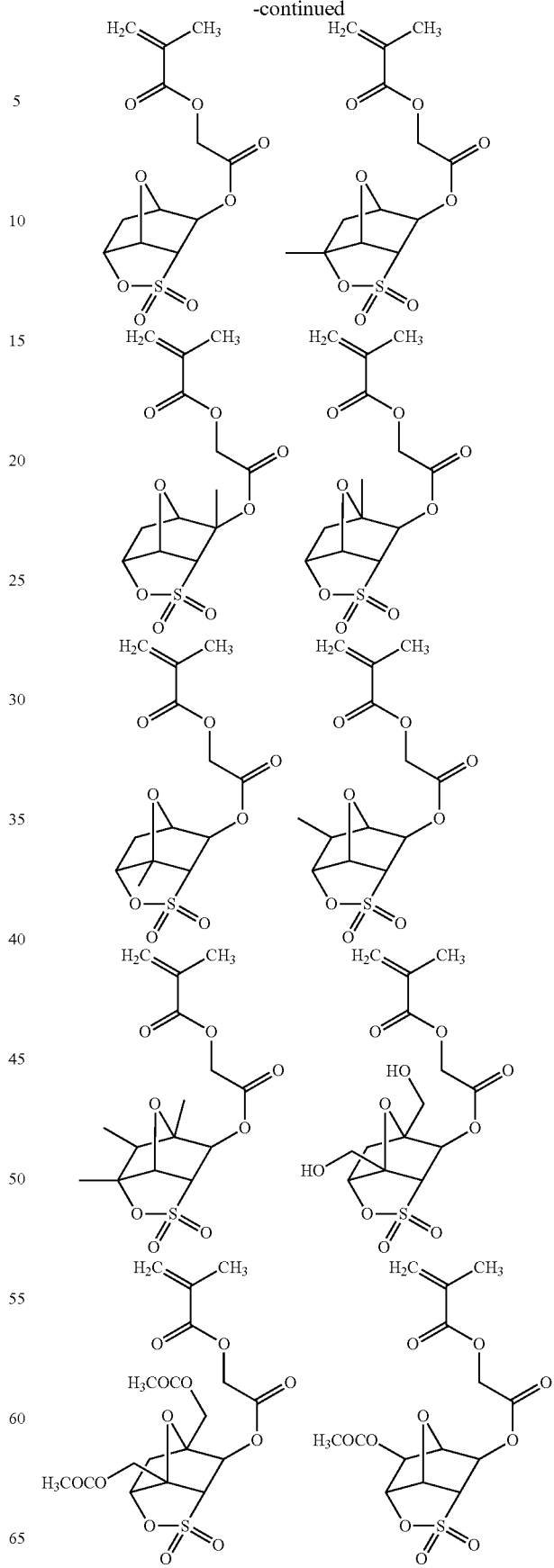

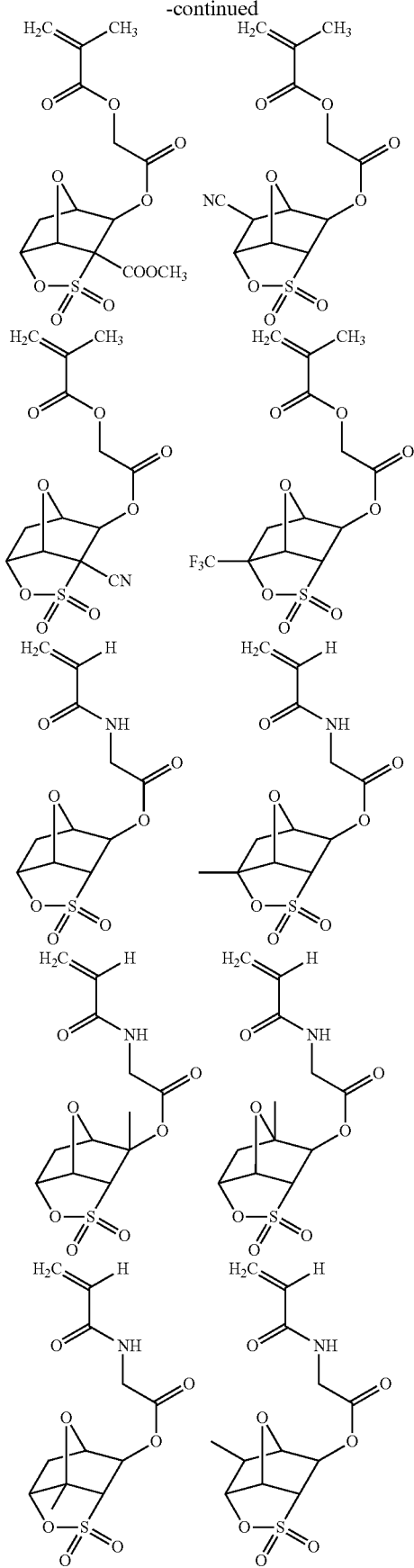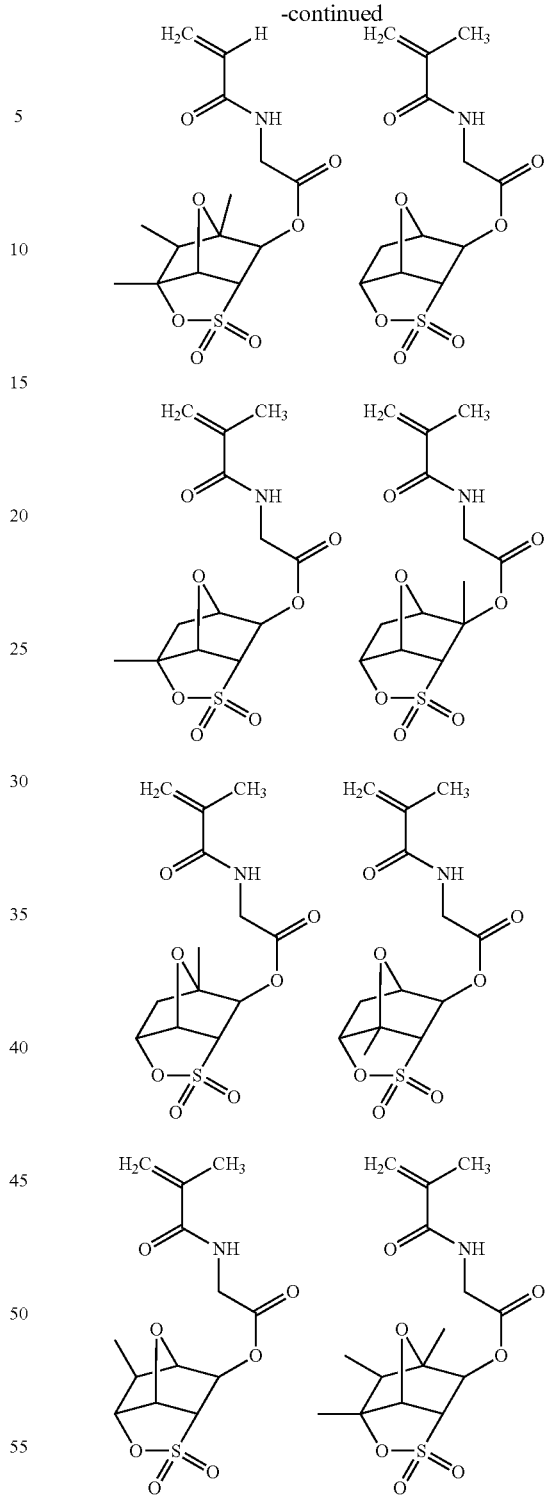

When the resin contains a structural unit derived from a monomer represented by the formula (a4-4), the content thereof is usually 2 to 40% by mole based on total molar of all the structural units of the resin, and preferably 3 to 35% by mole and more preferably 5 to 30% by mole.

Examples of the other monomer having no acid-labile group include the fluorine-containing monomers represented by the following formulae.

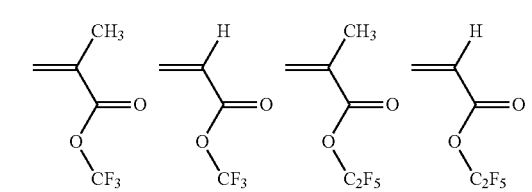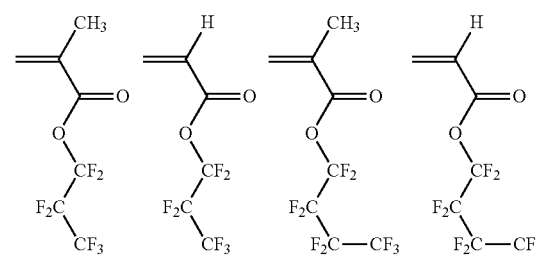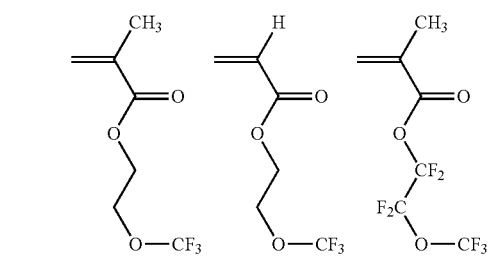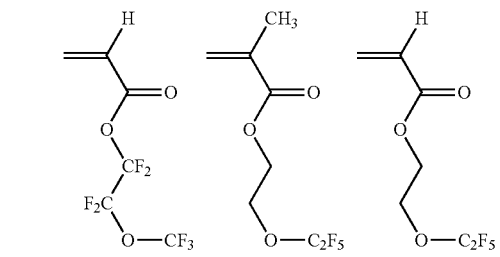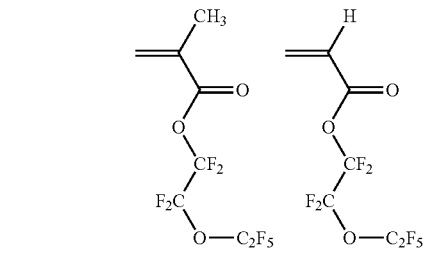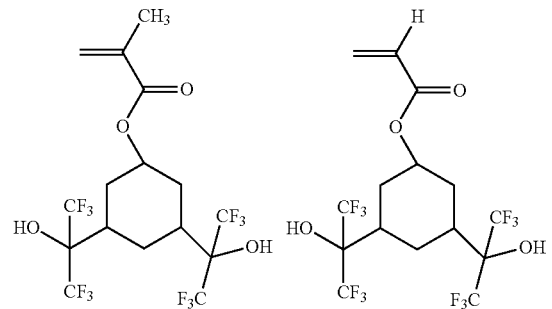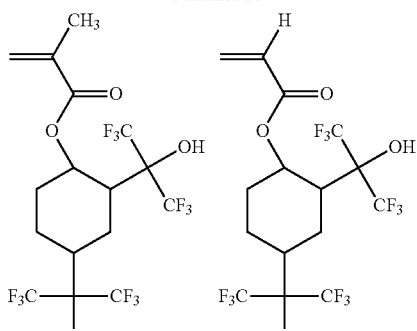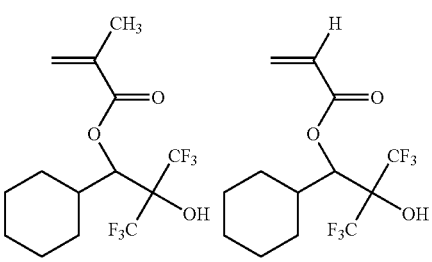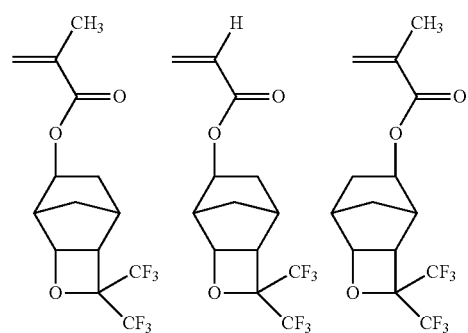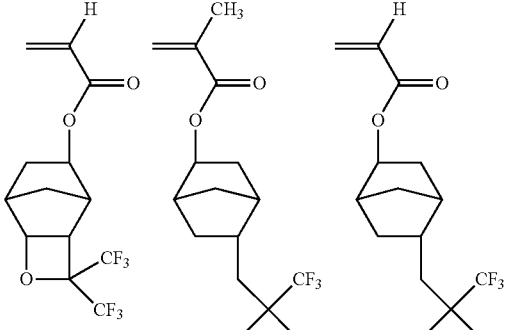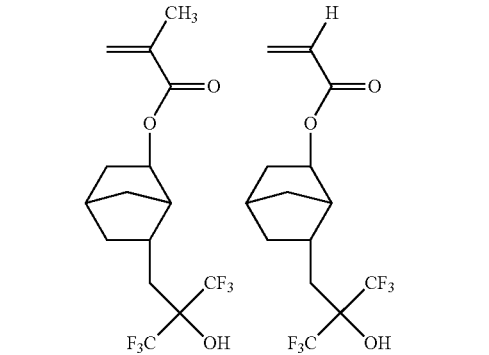

-continued

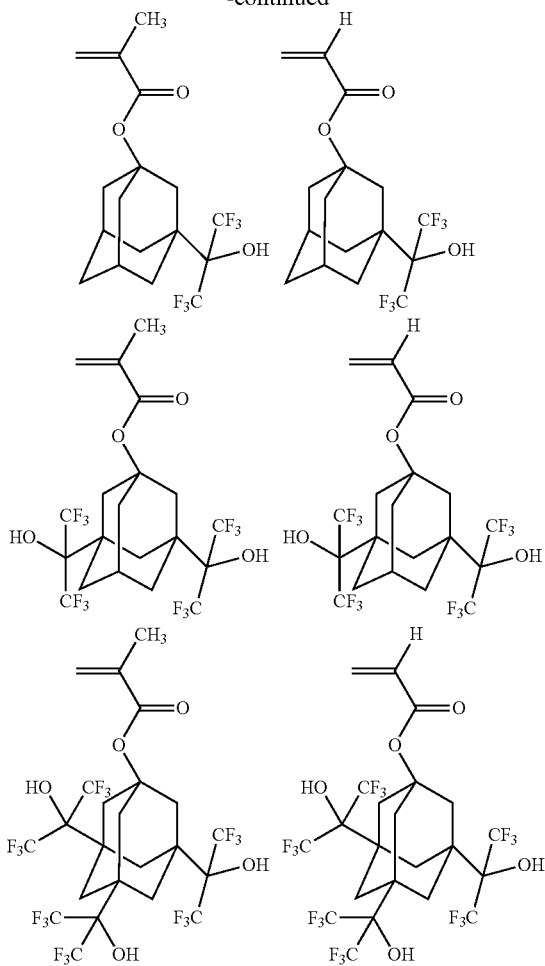

Among them, preferred are 5-(3,3,3-trifluoro-2-hydroxy-2-(trifluoromethyl)propyl)bicyclo[2.2.1]hept-2-yl acrylate, 5-(3,3,3-trifluoro-2-hydroxy-2-(trifluoromethyl)propyl)bicyclo[2.2.1]hept-2-yl methacrylate, 6-(3,3,3-trifluoro-2-hydroxy-2-(trifluoromethyl)propyl)bicyclo[2.2.1]hept-2-yl acrylate, 5-(3,3,3-trifluoro-2-hydroxy-2-(trifluoromethyl) propyl)bicyclo[2.2.1]hept-2-yl methacrylate, 4,4-bis(trifluoromethyl)-3-oxatricyclo[4.2.1.0$^{2,5}$]nonyl acrylate and 4,4-bis(trifluoromethyl)-3-oxatricyclo[4.2.1.0$^{2,5}$]nonyl methacrylate.

When the resin contains a structural unit derived from the above-mentioned fluorine-containing monomer, the content thereof is usually 1 to 20% by mole based on total molar of all the structural units of the resin, and preferably 2 to 15% by mole and more preferably 3 to 10% by mole.

Examples of the other monomer having no acid-labile group include the monomers having a group represented by the formula (3):

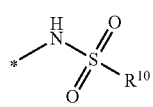 (3)

wherein $R^{10}$ represents a C1-C6 fluorinated alkyl group, in its side chain.

Examples of the C1-C6 fluorinated alkyl group include a difluoromethyl group, a trifluoromethyl group, a 1,1-difluoroethyl group, a 2,2-difluoroethyl group, a 2,2,2-trifluoroethyl group, a perfluoroethyl group, a 1,1,2,2-tetrafluoropropyl group, a 1,1,2,2,3,3-hexafluoropropyl group, a (perfluoroethyl)methyl group, a 1-(trifluoromethyl)-1,2,2,2-tetrafluoroethyl group, a perfluoropropyl group, a 1,1,2,2-tetrafluorobutyl group, a 1,1,2,2,3,3-hexafluorobutyl group, a 1,1,2,2,3,3,4,4-octafluorobutyl group, a perfluorobutyl group, a 1,1-bis(trifluoromethyl)-2,2,2-trifluoroethyl group, 2-(perfluoropropyl)ethyl group, a 1,1,2,2,3,3,4,4-octafluoropentyl group, a perfluoropentyl group, a 1,1,2,2,3,3,4,4,5,5-decafluoropentyl group, a 1,1-bis(trifluoromethyl)-2,2,3,3,3,-pentafluoropropyl group, a perfluoropentyl group, a 2-(perfluorobutyl)ethyl group, a 1,1,2,2,3,3,4,4,5,5-decafluorohexyl group, a 1,1,2,2,3,3,4,4,5,5,6,6-dodecafluorohexyl group, a (perfluoropentyl)methyl group and a perfluorohexyl group. Among them preferred is a C1-C4 fluorinated alkyl group, and more preferred are a trifluoromethyl group, a perfluoroethyl group and a perfluoropropyl group, and especially preferred is a trifluoromethyl group.

Examples of the monomer having the group represented by the formula (3) in its side chain include the following.

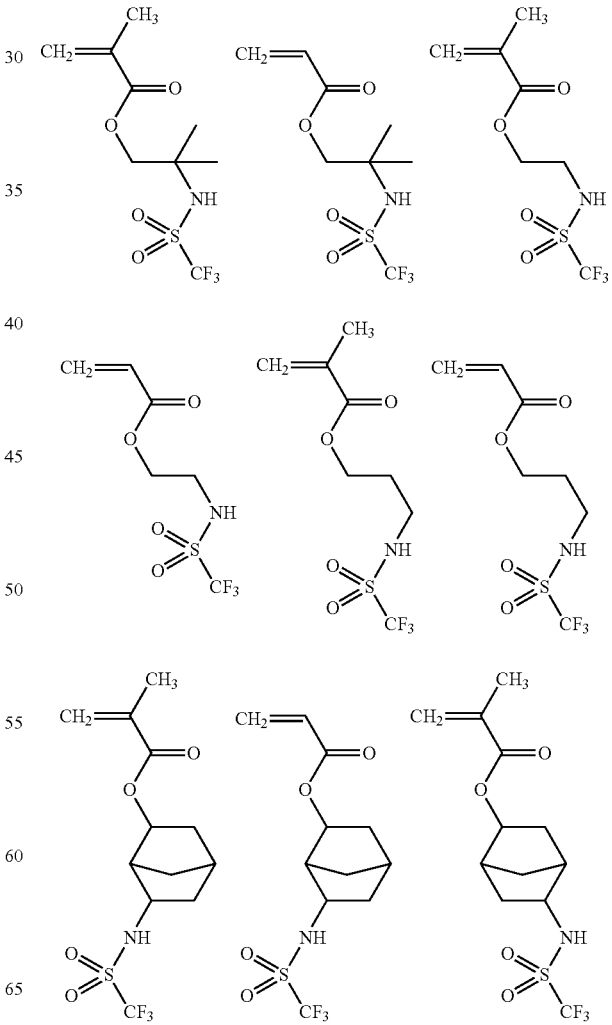

135
-continued
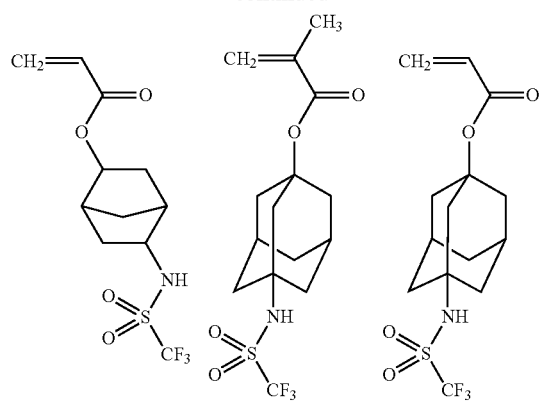
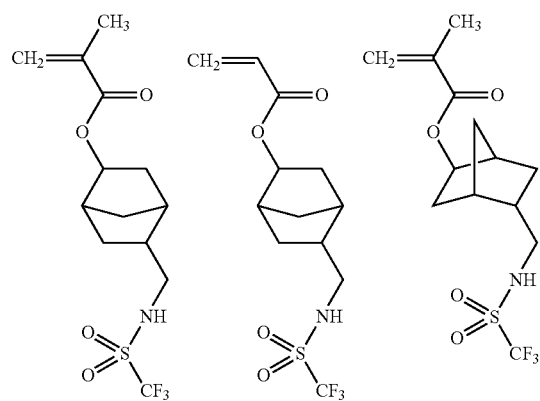
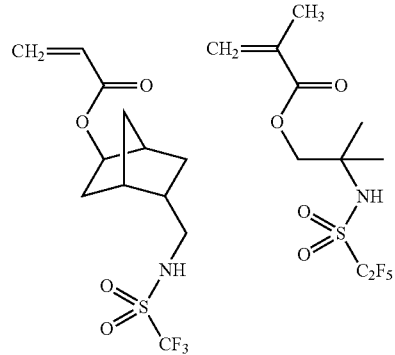
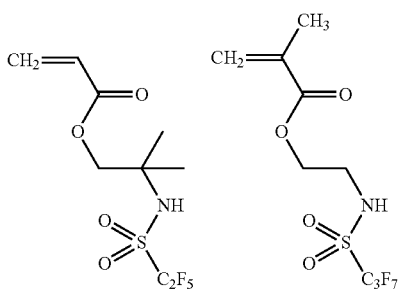
136
-continued
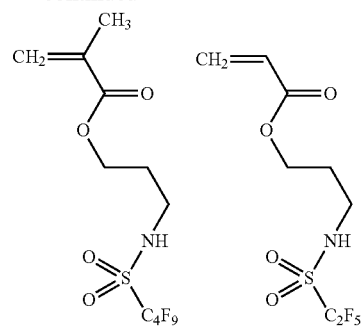
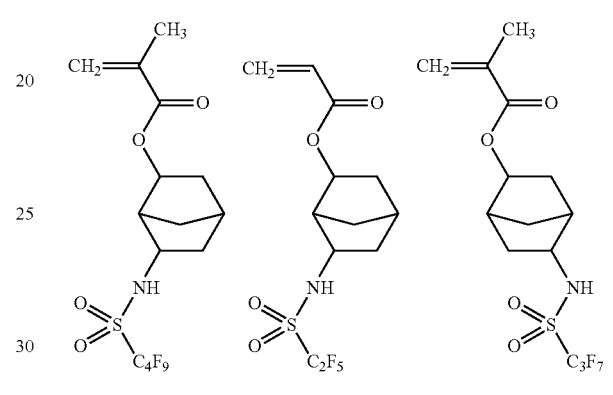
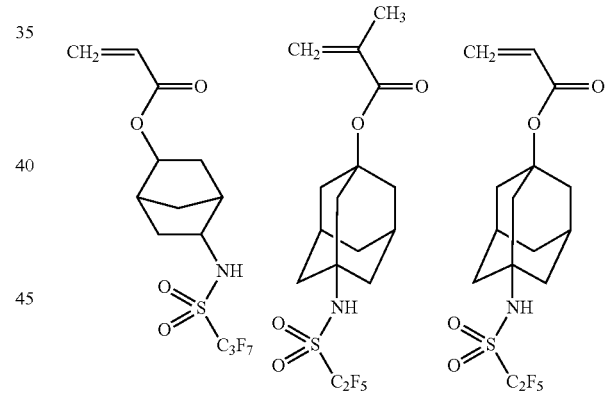
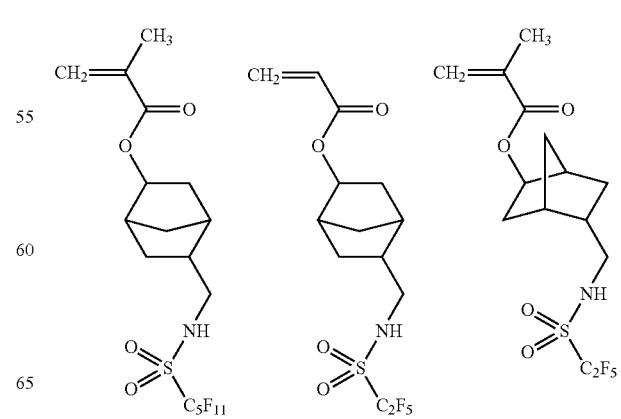

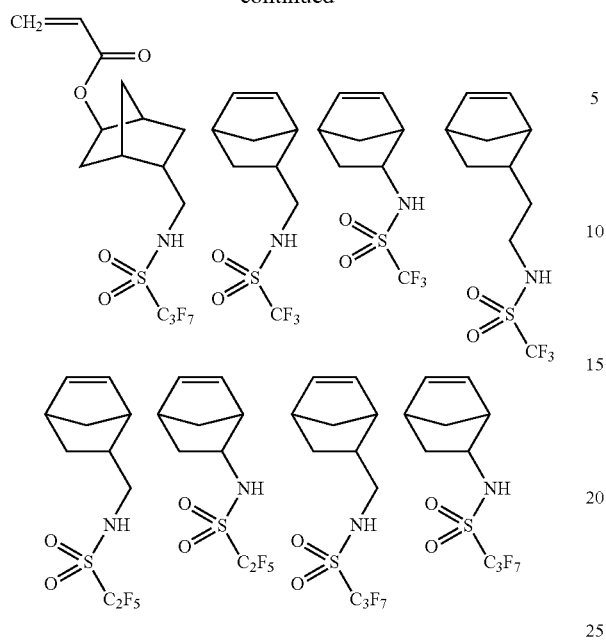

When the resin contains a structural unit derived from the above-mentioned monomer having the group represented by the formula (3) in its side chain, the content thereof is usually 5 to 90% by mole based on total molar of all the structural units of the resin, and preferably 10 to 80% by mole and more preferably 20 to 70% by mole.

Examples of the other monomer having no acid-labile group include the monomers having a group represented by the formula (4):

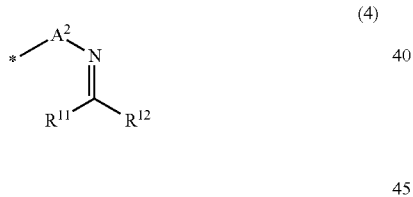

wherein $R^{11}$ represents a C6-C12 aromatic hydrocarbon group which may have one or more substituents, $R^{12}$ represents a C1-C12 hydrocarbon group which may have one or more substituents and which may contain one or more heteroatoms, and $A^2$ represents a single bond, —(CH$_2$)$_m$—SO$_2$—O—* or —(CH$_2$)$_m$—CO—O—* in which one or more —CH$_2$— may be replaced by —O—, —CO— or —SO$_2$— and in which one or more hydrogen atoms may be replaced by a fluorine atom, and m represents an integer of 1 to 12, in its side chain.

Examples of the substituents of the aromatic hydrocarbon group include a C1-C4 alkyl group such as a methyl group, an ethyl group, a propyl group, an isopropyl group, a butyl, group, an isobutyl group and a tert-butyl group, a halogen atom such as a fluorine atom, a chlorine atom and a bromine atom, a phenyl group, a nitro group, a cyano group, a hydroxyl group, a phenoxy group and a tert-butylphenyl group.

Examples of $R^{11}$ include the following. In the following formulae, * represents a binding position to —C($R^{12}$)=N.

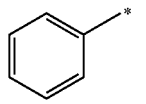
(R$^{11}$-1)

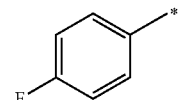
(R$^{11}$-2)

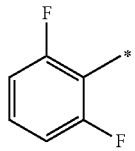
(R$^{11}$-3)

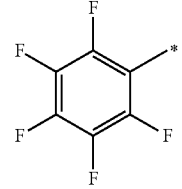
(R$^{11}$-4)

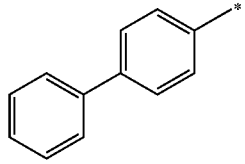
(R$^{11}$-5)

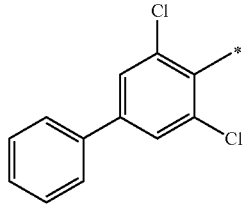
(R$^{11}$-6)

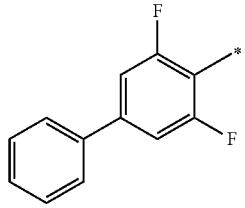
(R$^{11}$-7)

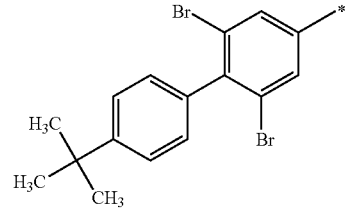
(R$^{11}$-8)

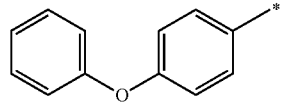
(R$^{11}$-9)

-continued

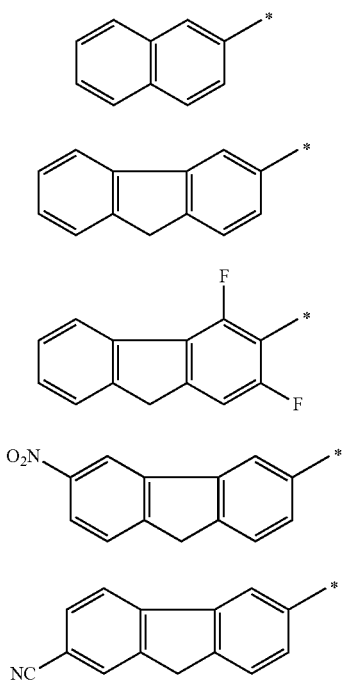

(R¹¹-10)
(R¹¹-11)
(R¹¹-12)
(R¹¹-13)
(R¹¹-14)

Examples of the C1-C12 hydrocarbon group include a C1-C12 aliphatic hydrocarbon group, a C3-C12 alicyclic hydrocarbon group and a C6-C12 aromatic hydrocarbon group. Examples of the C1-C12 aliphatic hydrocarbon group include a linear aliphatic hydrocarbon group such as a methyl group, an ethyl group, a propyl group, a butyl group, a pentyl group, a hexyl group, a heptyl group, an octyl group, a nonyl group, a decyl group, an undecyl group and a dodecyl group, and a branched chain aliphatic hydrocarbon group such as an isopropyl group, a sec-butyl group, a tart-butyl group, a methylpentyl group, an ethylpentyl group, a methylhexyl group, an ethylhexyl group, a propylhexyl group and a tert-octyl group. Preferred is a branched chain aliphatic hydrocarbon group, and more preferred are an isopropyl group, a sec-butyl group, a tert-butyl group and an ethylhexyl group.

Examples of the C3-C12 alicyclic hydrocarbon group include the following. In the following formulae, * represents a binding position to —C(R¹¹)=N.

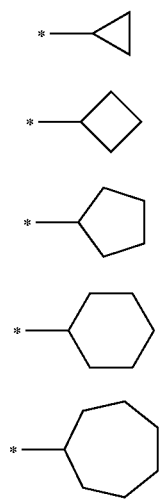

(R¹²-19)
(R¹²-20)
(R¹²-21)
(R¹²-22)
(R¹²-23)
(R¹²-24)
(R¹²-25)
(R¹²-26)
(R¹²-27)
(R¹²-28)

The C1-C12 hydrocarbon group may contain one or more heteroatoms such as a halogen atom, a sulfur atom, an oxygen atom and a nitrogen atom, and it may also contain a group formed by combining two or more heteroatoms such as —SO₂— and —CO—. Examples of the C1-C12 hydrocarbon group containing one or more heteroatoms include the following.

\* —CF₃     (R¹²-1)

\* —CN     (R¹²-2)

\* —CH₃     (R¹²-3)

(R¹²-4)

\* —CF₂CH₃     (R¹²-5)

\* —CF₂CF₃     (R¹²-6)

\* —CF₂CF₂CF₃     (R¹²-7)

\* —CF₂C₂H₅     (R¹²-8)

\* —CF₂CF₂CF₂—CO₂—CH₃     (R¹²-9)

$$* -CF_2-\underset{\underset{O}{\|}}{\overset{\overset{O}{\|}}{S}}-C_2H_5 \qquad (R^{12}\text{-}9)$$

$$* -CF_2-\underset{\underset{O}{\|}}{\overset{\overset{O}{\|}}{S}}-CF_2CF_3 \qquad (R^{12}\text{-}10)$$

-continued
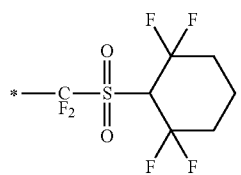 (R$^{12}$-11)
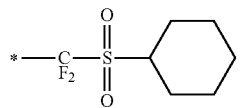 (R$^{12}$-12)
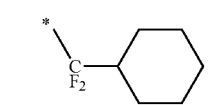 (R$^{12}$-13)
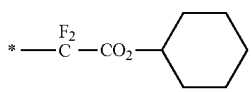 (R$^{12}$-14)
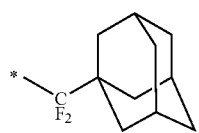 (R$^{12}$-15)
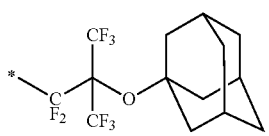 (R$^{12}$-16)
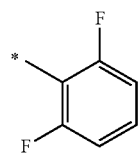 (R$^{12}$-17)
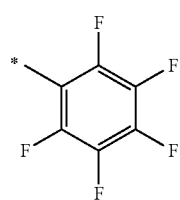 (R$^{12}$-18)
Examples of the C6-C12 aromatic hydrocarbon group include the same as those of R$^{11}$.
Examples of A$^2$ include the following.
\*— (A$^2$-1)
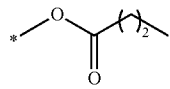 (A$^2$-2)
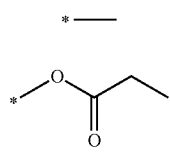 (A$^2$-3)
-continued
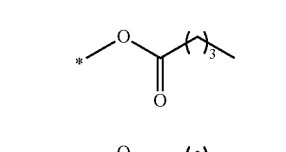 (A$^2$-4)
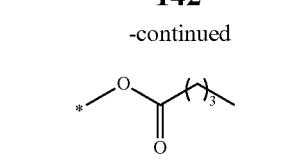 (A$^2$-5)
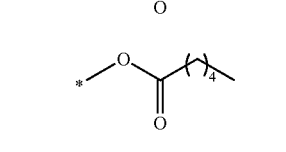 (A$^2$-6)
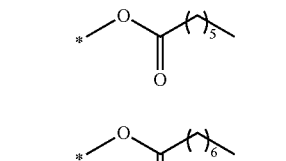 (A$^2$-7)
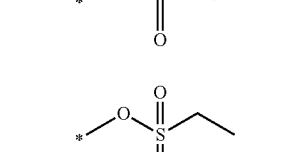 (A$^2$-8)
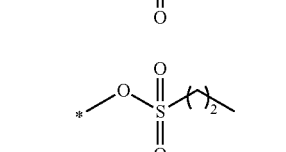 (A$^2$-9)
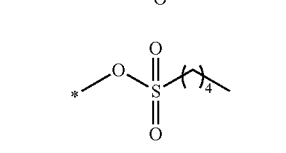 (A$^2$-10)
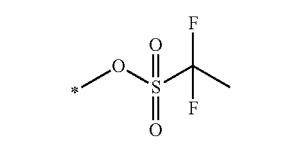 (A$^2$-11)
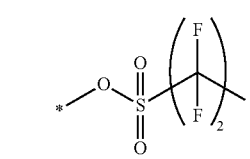 (A$^2$-12)
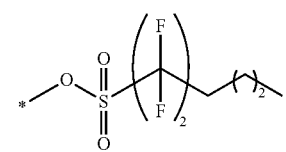 (A$^2$-13)
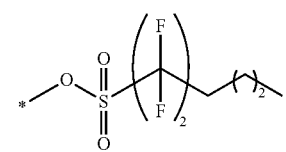 (A$^2$-14)
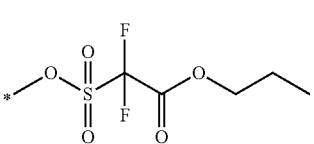 (A$^2$-15)

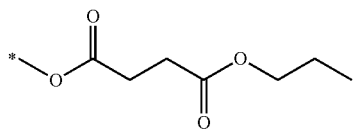

(A²-16)

wherein * represents a binding position to —N=C(R¹¹)(R¹²).

In the above-mentioned formulae, the group represented by the formula (A²-1) represents a single bond.

Preferable examples of the monomer having the group represented by the formula (4) include a monomer represented by the formula (a6-1):

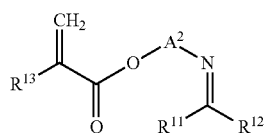

(a6-1)

wherein A², R¹¹ and R¹² are the same as defined above, and R¹³ represents a hydrogen atom or a methyl group.

Examples of the monomer represented by the formula (a6-1) include the following.

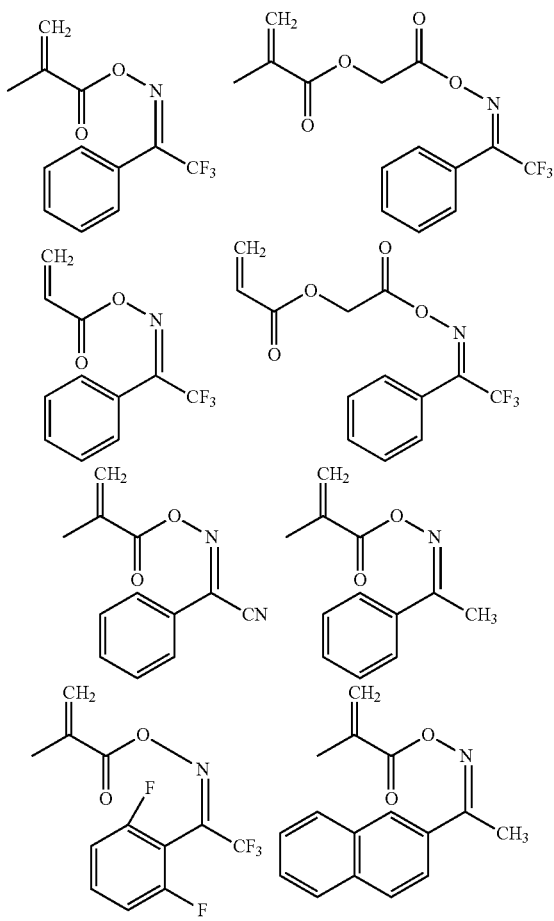

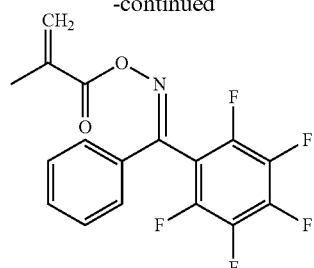

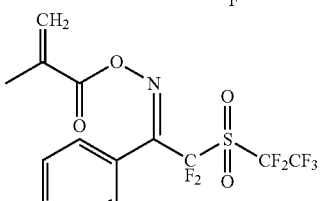

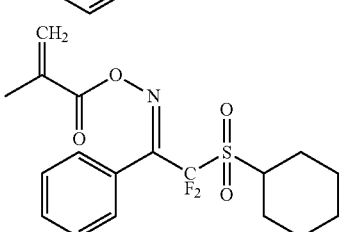

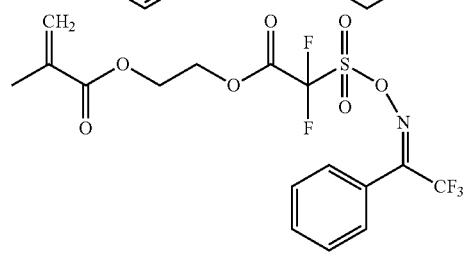

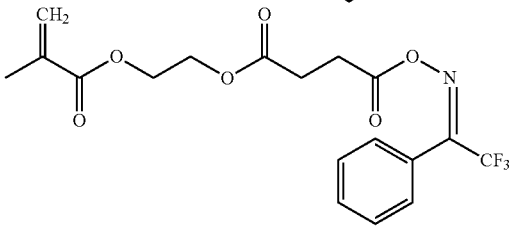

When the resin contains a structural unit derived from the above-mentioned monomer having the group represented by the formula (4) in its side chain, the content thereof is usually 5 to 90% by mole based on total molar of all the structural units of the resin, and preferably 10 to 80% by mole and more preferably 20 to 70% by mole.

Preferable resin is a resin containing the structural units derived from the monomer having an acid-labile group and the structural units derived from the monomer having no acid-labile group, and more preferable resin is a resin containing the structural units derived from the monomer having an acid-labile group and the structural units derived from the monomer having one or more hydroxyl groups and/or the monomer having a lactone ring. The monomer having an acid-labile group is preferably the monomer represented by the formula (a1-1) or the monomer represented by the formula (a1-2), and is more preferably the monomer represented by the formula (a1-1). The monomer having one or more hydroxyl groups is preferably the monomer represented by the formula (a2-1), and the monomer having a lactone ring is preferably the monomer represented by the formula (a3-1) or (a3-2).

The resin can be produced according to known polymerization methods such as radical polymerization.

The resin usually has 2,500 or more of the weight-average molecular weight, preferably 3,000 or more of the weight-average molecular weight. The resin usually has 50,000 or less of the weight-average molecular weight, preferably has 30,000 or less of the weight-average molecular weight. The weight-average molecular weight can be measured with gel permeation chromatography.

The content of the acid generator is usually 1 part by weight or more per 100 parts of the resin, and preferably 3 parts by weight or more. The content of the acid generator is usually 30 parts by weight or less per 100 parts of the resin, and preferably 25 parts by weight or less.

The photoresist compositions of the present invention can contain a basic compound as a quencher. The basic compound has the property that it can trap an acid, especially an acid generated from the acid generator by applying a radiation.

The basic compound is preferably a basic nitrogen-containing organic compound, and examples thereof include an amine compound such as an aliphatic amine and an aromatic amine and an ammonium salt. Examples of the aliphatic amine include a primary amine, a secondary amine and a tertiary amine. Examples of the aromatic amine include an aromatic amine in which aromatic ring has one or more amino groups such as aniline and a heteroaromatic amine such as pyridine. Preferable examples thereof include an aromatic amine represented by the formula (C2):

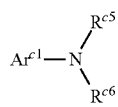
(C2)

wherein $Ar^{c1}$ represents an aromatic hydrocarbon group, and $R^{c5}$ and $R^{c6}$ independently represent a hydrogen atom, an aliphatic hydrocarbon group, a saturated cyclic hydrocarbon group or an aromatic hydrocarbon group, and the aliphatic hydrocarbon group, the saturated cyclic hydrocarbon group and the aromatic hydrocarbon group can have one or more substituents selected from the group consisting of a hydroxyl group, an amino group, an amino group having one or two C1-C4 alkyl groups and a C1-C6 alkoxy group.

The aliphatic hydrocarbon group is preferably an alkyl group and the saturated cyclic hydrocarbon group is preferably a cycloalkyl group. The aliphatic hydrocarbon group preferably has 1 to 6 carbon atoms. The saturated cyclic hydrocarbon group preferably has 5 to 10 carbon atoms. The aromatic hydrocarbon group preferably has 6 to 10 carbon atoms.

As the aromatic amine represented by the formula (C2), an amine represented by the formula (C2-1);

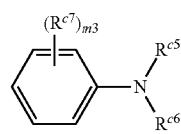
(C2-1)

wherein $R^{c5}$ and $R^{c6}$ are the same as defined above, and $R^{c7}$ is independently in each occurrence an aliphatic hydrocarbon group, an alkoxy group, a saturated cyclic hydrocarbon group or an aromatic hydrocarbon group, and the aliphatic hydrocarbon group, the alkoxy group, the saturated cyclic hydrocarbon group and the aromatic hydrocarbon group can have one or more substituents selected from the group consisting of a hydroxyl group, an amino group, an amino group having one or two C1-C4 alkyl groups and a C1-C6 alkoxy group, and m3 represents an integer of 0 to 3, is preferable. The aliphatic hydrocarbon group is preferably an alkyl group and the saturated cyclic hydrocarbon group is preferably a cycloalkyl group. The aliphatic hydrocarbon group preferably has 1 to 6 carbon atoms. The saturated cyclic hydrocarbon group preferably has 5 to 10 carbon atoms. The aromatic hydrocarbon group preferably has 6 to 10 carbon atoms. The alkoxy group preferably has 1 to 6 carbon atoms.

Examples of the aromatic amine represented by the formula (C2) include 1-naphthylamine, 2-naphthylamine, aniline, diisopropylaniline, 2-methylaniline, 3-methylaniline, 4-methylaniline, 4-nitroaniline, N-methylaniline, N,N-dimethylaniline, and diphenylamine, and among them, preferred is diisopropylaniline and more preferred is 2,6-diisopropylaniline Other examples of the basic compound include amines represented by the formulae (C3) to (C11):

(C3)

(C4)

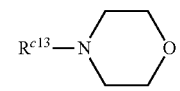
(C5)

(C6)

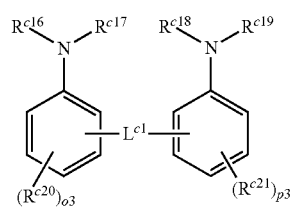
(C7)

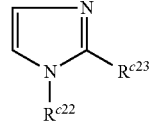
(C8)

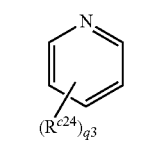
(C9)

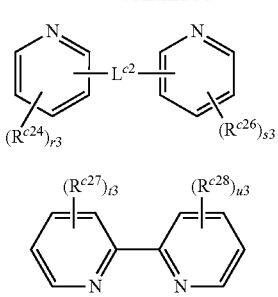

(C10)

(C11)

wherein $R^{c8}$, $R^{c20}$, $R^{c21}$, and $R^{c23}$ to $R^{c28}$ independently represent an aliphatic hydrocarbon group, an alkoxy group, a saturated cyclic hydrocarbon group or an aromatic hydrocarbon group, and the aliphatic hydrocarbon group, the alkoxy group, the saturated cyclic hydrocarbon group and the aromatic hydrocarbon group can have one or more substituents selected from the group consisting of a hydroxyl group, an amino group, an amino group having one or two C1-C4 alkyl groups and a C1-C6 alkoxy group, $R^{c9}$, $R^{c10}$, $R^{c11}$ to $R^{c14}$, $R^{c16}$ to $R^{c19}$, and $R^{c22}$ independently represents a hydrogen atom, an aliphatic hydrocarbon group, a saturated cyclic hydrocarbon group or an aromatic hydrocarbon group, and the aliphatic hydrocarbon group, the saturated cyclic hydrocarbon group and the aromatic hydrocarbon group can have one or more substituents selected from the group consisting of a hydroxyl group, an amino group, an amino group having one or two C1-C4 alkyl groups and a C1-C6 alkoxy group, $R^{c15}$ is independently in each occurrence an aliphatic hydrocarbon group, a saturated cyclic hydrocarbon group or an alkanoyl group, $L^{c1}$ and $L^{c2}$ independently represents a divalent aliphatic hydrocarbon group, —CO—, —C(=NH)—, —C(=NR$^{c3}$)—S—, —S—S— or a combination thereof and $R^{c3}$ represents a C1-C4 alkyl group, O3 to u3 each independently represents an integer of 0 to 3 and n3 represents an integer of 0 to 8.

The aliphatic hydrocarbon group has preferably 1 to 6 carbon atoms, and the saturated cyclic hydrocarbon group has preferably 3 to 6 carbon atoms, and the alkanoyl group has preferably 2 to 6 carbon atoms, and the divalent aliphatic hydrocarbon group has preferably 1 to 6 carbon atoms. The divalent aliphatic hydrocarbon group is preferably an alkylene group.

Examples of the amine represented by the formula (C3) include hexylamine, heptylamine, octylamine, nonylamine, decylamine, dibutylamine, dipentylamine, dihexylamine, diheptylamine, dibutylamine, dinonylamine, didecylamine, triethylamine, trimethylamine, tripropylamine, tributylamine, tripentylamine, trihexylamine, triheptylamine, trioctylamine, trinonylamine, tridecylamine, methyldibutylamine, methyldipentylamine, methyldihexylamine, methyldicyclohexylamine, methyldiheptylamine, methyldioctylamine, methyldinonylamine, methyldidecylamine, ethyldibutylamine, ethydipentylamine, ethyldihexylamine, ethydiheptylamine, ethyldioctylamine, ethyldinonylamine, ethyldidecylamine, dicyclohexylmethylamine, tris[2-(2-methoxyethoxy)ethyl]amine, triisopropanolamine, ethylenediamine, tetramethylenediamine, hexamethylenediamine, 4,4'-diamino-1,2-diphenylethane, 4,4'-diamino-3,3'-dimethyldiphenylmethane and 4,4'-diamino-3,3'-diethyldiphenylmethane.

Examples of the amine represented by the formula (C4) include piperazine. Examples of the amine represented by the formula (C5) include morpholine. Examples of the amine represented by the formula (C6) include piperidine and hindered amine compounds having a piperidine skeleton as disclosed in JP 11-52575 A. Examples of the amine represented by the formula (C7) include 2,2'-methylenebisaniline. Examples of the amine represented by the formula (C8) include imidazole and 4-methylimidazole. Examples of the amine represented by the formula (C9) include pyridine and 4-methylpyridine. Examples of the amine represented by the formula (C10) include di-2-pyridyl ketone, 1,2-di(2-pyridyl)ethane, 1,2-di(4-pyridyl)ethane, 1,3-di(4-pyridyl)propane, 1,2-bis(2-pyridyl)ethene, 1,2-bis(4-pyridyl)ethene, 1,2-di(4-pyridyloxy)ethane, 4,4'-dipyridyl sulfide, 4,4'-dipyridyl disulfide, 2,2'-dipyridylamine and 2,2'-dipicolylamine. Examples of the amine represented by the formula (C11) include bipyridine.

Examples of the quaternary ammonium hydroxide include tetramethylammonium hydroxide, tetrabutylammonium hydroxide, tetrahexylammonium hydroxide, tetraoctylammonium hydroxide, phenyltrimethylammonium hydroxide, (3-trifluoromethylphenyl)trimethylammonium hydroxide and (2-hydroxyethyl)trimethylammonium hydroxide (so-called "choline").

When the photoresist compositions contain the basic compound, the content thereof is usually 0.01 to 1% by weight based on sum of solid component. The content of the basic compound is preferably smaller than total content of SALT (I) and the acid generator other than SALT (I). In this specification, "solid component" means components other than solvent in the photoresist composition.

The photoresist compositions of the present invention usually contain one or more solvents. Examples of the solvent include a glycol ether ester such as ethyl cellosolve acetate, methyl cellosolve acetate and propylene glycol monomethyl ether acetate; a glycol ether such as propylene glycol monomethyl ether; an acyclic ester such as ethyl lactate, butyl acetate, amyl acetate and ethyl pyruvate; a ketone such as acetone, methyl isobutyl ketone, 2-heptanone and cyclohexanone; and a cyclic ester such as γ-butyrolactone.

The amount of the solvent is usually 90% by weight or more, preferably 92% by weight or more preferably 94% by weight or more based on total amount of the photoresist composition of the present invention. The amount of the solvent is usually 99.9% by weight or less and preferably 99% by weight or less based on total amount of the photoresist composition of the present invention.

The photoresist compositions of the present invention can contain, if necessary, a small amount of various additives such as a sensitizer, a dissolution inhibitor, other polymers, a surfactant, a stabilizer and a dye as long as the effect of the present invention is not prevented.

The photoresist compositions of the present invention are useful for a chemically amplified photoresist composition.

A photoresist pattern can be produced by the following steps (1) to (5):

(1) a step of applying the first or second photoresist composition of the present invention on a substrate, (2) a step of forming a photoresist film by conducting drying, (3) a step of exposing the photoresist film to radiation, (4) a step of baking the exposed photoresist film, and (5) a step of developing the baked photoresist film with an alkaline developer, thereby forming a photoresist pattern.

The applying of the photoresist composition on a substrate is usually conducted using a conventional apparatus such as spin coater. The photoresist composition is preferably filtrated with filter having a pore size of 0.01 to 0.2 μm before applying. Examples of the substrate include a silicon wafer or a quartz wafer on which a sensor, a circuit, a transistor or the like is formed.

The formation of the photoresist film is usually conducted using a heating apparatus such as hot plate or a decompressor, and the heating temperature is usually 50 to 200° C., and the operation pressure is usually 1 to $1.0*10^5$ Pa.

The photoresist film obtained is exposed to radiation using an exposure system. The exposure is usually conducted through a mask having a pattern corresponding to the desired photoresist pattern. Examples of the exposure source include a light source radiating laser light in a UV-region such as a KrF excimer laser (wavelength: 248 nm), an ArF excimer laser (wavelength: 193 nm) and a $F_2$ laser (wavelength: 157 nm), and a light source radiating harmonic laser light in a far UV region or a vacuum UV region by wavelength conversion of laser light from a solid laser light source (such as YAG or semiconductor laser).

The temperature of baking of the exposed photoresist film is usually 50 to 200° C., and preferably 70 to 150° C.

The development of the baked photoresist film is usually carried out using a development apparatus. The alkaline developer used may be any one of various alkaline aqueous solution used in the art. Generally, an aqueous solution of tetramethylammonium hydroxide or (2-hydroxyethyl)trimethylammonium hydroxide (commonly known as "choline") is often used. After development, the photoresist pattern formed is preferably washed with ultrapure water, and the remained water on the photoresist pattern and the substrate is preferably removed.

The photoresist composition of the present invention provides a photoresist pattern showing good Exposure Latitude (EL), and therefore, the photoresist composition of the present invention is suitable for ArF excimer laser lithography, KrF excimer laser lithography, ArF immersion lithography, EUV (extreme ultraviolet) lithography, EUV immersion lithography and EB (electron beam) lithography. Further, the photoresist composition of the present invention can especially be used for EUV lithography and EB lithography.

EXAMPLES

The present invention will be described more specifically by Examples, which are not construed to limit the scope of the present invention.

The "%" and "part(s)" used to represent the content of any component and the amount of any material used in the following examples and comparative examples are on a weight basis unless otherwise specifically noted. The weight-average molecular weight of any material used in the following examples is a value found by gel permeation chromatography [Column: Three of TSKgel Multipore HXL-M with guard column, manufactured by TOSOH CORPORATION, Solvent: tetrahydrofuran, Flow rate: 1.0 mL/min., Detector: RI Detector, Column temperature: 40° C., Injection volume: 100 μL] using standard polystyrene as a standard reference material. Structures of compounds were determined by mass spectrometry (Liquid Chromatography: 1100 Type, manufactured by AGILENT TECHNOLOGIES LTD., Mass Spectrometry: LC/MSD Type, manufactured by AGILENT TECHNOLOGIES LTD.).

Example 1

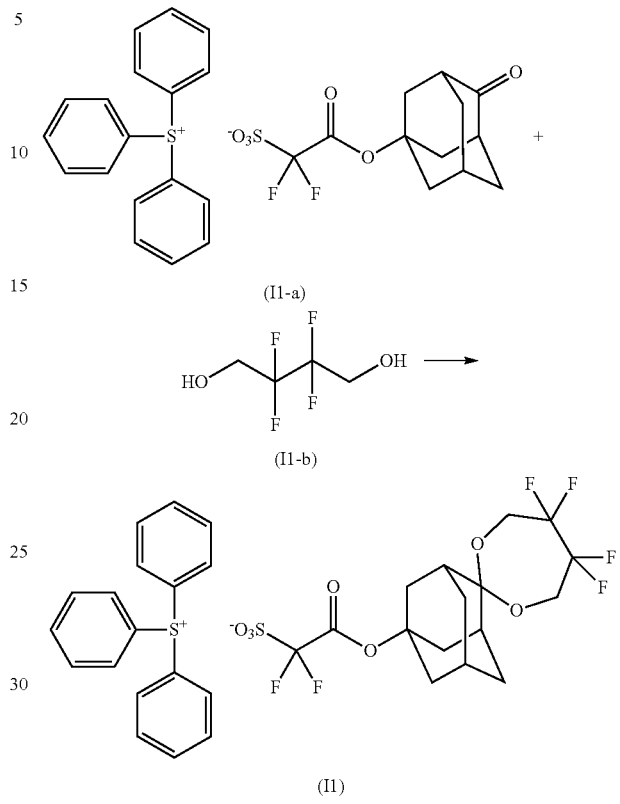

The salt represented by the formula (I1-a) was prepared according to the method described in JP 2007-224008 A.

A mixture of 10.00 parts of the salt represented by the formula (I1-a) and 40 parts of 1,2-dichloroethane was stirred at 23° C. for 30 minutes. To the mixture, 5.53 parts of the compound represented by the formula (I1-b) and 0.3 part of p-toluenesulfonic acid were added, and the resultant mixture was refluxed at 100° C. for 3 hours with stirring. The obtained mixture was cooled down to 23° C., and then, 120 parts of chloroform and 35.39 parts of 8.7% aqueous sodium hydrogen carbonate solution were added thereto followed by conducting stirring at 23° C. for 30 minutes. The mixture obtained was separated to an organic layer and art aqueous layer. The organic layer obtained was washed seven times with 120 parts of ion-exchanged water at 23° C. To the organic layer, 1 part of active carbon was added to stir at 23° C. for 30 minutes followed by filtration. The filtrate obtained was concentrated. To the residue obtained, 20 parts of acetonitrile was added to prepare a solution. The obtained solution was concentrated, and 8.14 parts of acetonitrile and 48.84 parts of tert-butyl methyl ether were added to the obtained residue. The resultant mixture was stirred at 23° C. for 1 hour and then, filtrated to obtain 8.25 parts of a salt represented by the formula (I1).

This is called as Salt I1.

MS (ESI(+) Spectrum): $M^+$ 263.1

MS (ESI(−) Spectrum); $M^−$ 467.1

Example 2

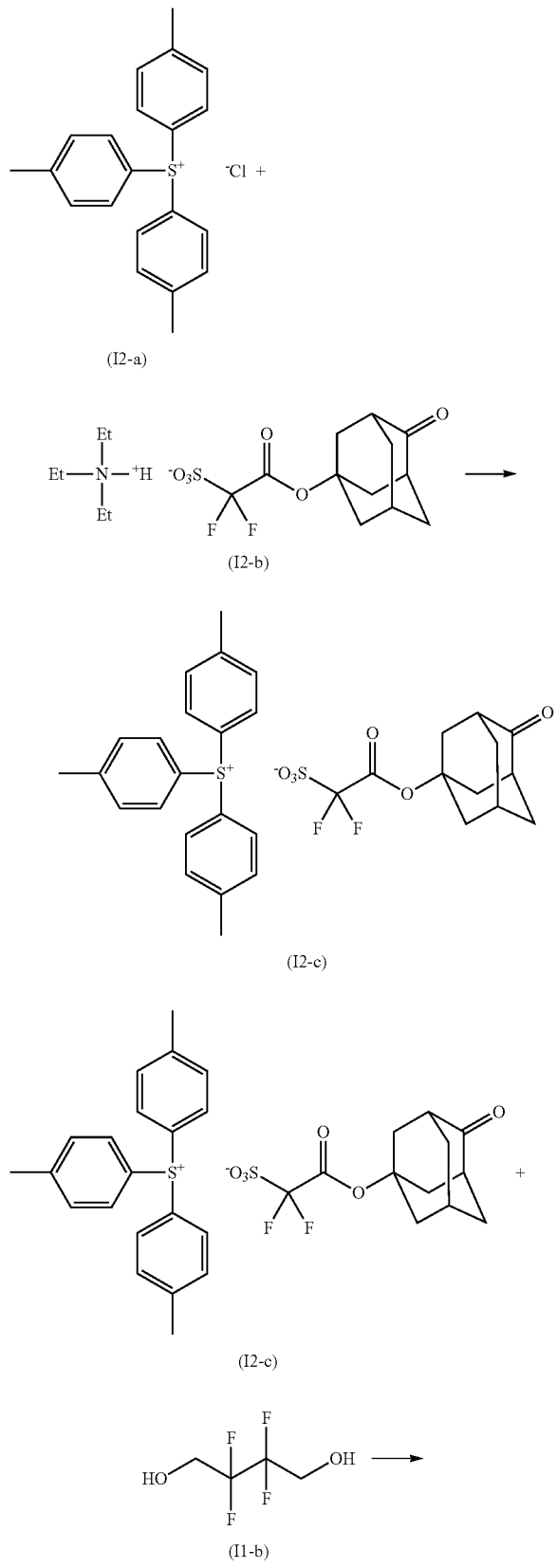

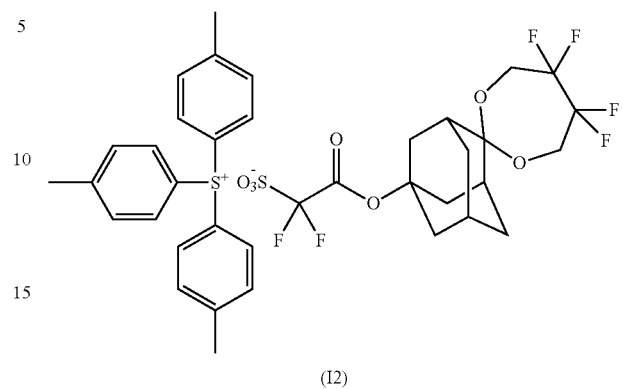

The salt represented by the formula (I2-b) was prepared according to the method described in JP 2008-94835 A.

A mixture of 17.5 parts of the salt represented by the formula (I2-a), 25.00 parts of the salt represented by the formula (I2-b) of which purity was 90.8%, 125 parts of chloroform and 41.67 parts of ion-exchanged water was stirred at 23° C. for 12 hours. The mixture obtained was separated to an organic layer and an aqueous layer. The organic layer obtained was washed nine times with 31.25 parts of ion-exchanged water. To the organic layer, 1 part of active carbon was added to stir at 23° C. for 30 minutes followed by filtration. The filtrate obtained was concentrated. To the residue obtained, 50 parts of acetonitrile was added to prepare a solution. The obtained solution was concentrated, and 173.13 parts of tert-butyl methyl ether was added to the obtained residue. The resultant mixture was filtrated to obtain 28.42 parts of a salt represented by the formula (I2-c).

A mixture of 10.72 parts of the salt represented by the formula (I2-c) and 42.88 parts of 1,2-dichloroethane was stirred at 23° C. for 30 minutes. To the mixture, 5.53 parts of the compound represented by the formula (I1-b) and 0.3 part of p-toluenesulfonic acid were added, and the resultant mixture was refluxed at 100° C. for 3 hours with stirring. The obtained mixture was cooled down to 23° C., and then, 120 parts of chloroform and 35.39 parts of 8.7% aqueous sodium hydrogen carbonate solution were added thereto followed by conducting stirring at 23° C. for 30 minutes. The mixture obtained was separated to an organic layer and an aqueous layer. The organic layer obtained was washed seven times with 120 parts of ion-exchanged water at 23° C. To the organic layer, 1 part of active carbon was added to stir at 23° C. for 30 minutes followed by filtration. The filtrate obtained was concentrated. To the residue obtained, 20 parts of acetonitrile was added to prepare a solution. The obtained solution was concentrated, and 9.12 parts of acetonitrile and 54.72 parts of tert-butyl methyl ether were added to the obtained residue. The resultant mixture was stirred at 23° C. for 1 hour and then, filtrated to obtain 8.49 parts of a salt represented by the formula (I2).

This is called as Salt I2.

MS (ESI(+) Spectrum): $M^+$ 305.1

MS (ESI(−) Spectrum): $M^-$ 467.1

Example 3

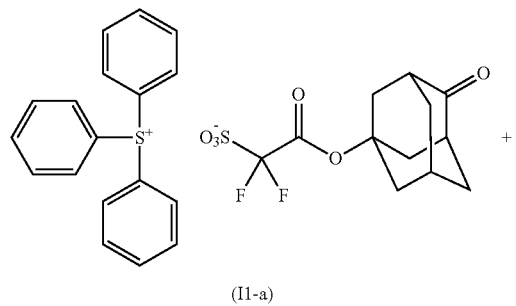

(I1-a)

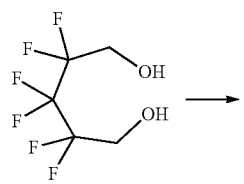

(I3-b)

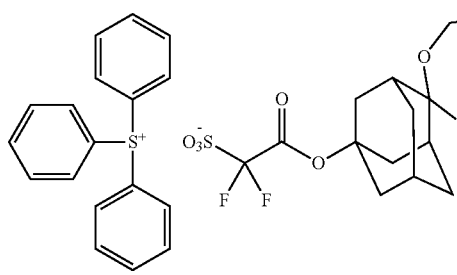

(I3)

A mixture of 6 parts of the salt represented by the formula (I1-a) and 36 parts of chloroform was stirred at 23° C. for 30 minutes. To the mixture, 2.60 parts of the compound represented by the formula (I3-b) and 0.10 part of sulfuric acid were added, and the resultant mixture was refluxed at 65° C. for 24 hours with stirring. The obtained mixture was cooled down to 23° C., and then, 50 parts of chloroform and 30 parts of ion-exchanged water were added thereto followed by conducting stirring at 23° C. for 30 minutes. The mixture obtained was separated to an organic layer and an aqueous layer. The organic layer obtained was washed six times with 30 parts of ion-exchanged water at 23° C. To the organic layer, 1' part of active carbon was added to stir at 23° C. for 30 minutes followed by filtration. The filtrate obtained was concentrated. To the residue obtained, 20 parts of acetonitrile was added to prepare a solution. The obtained solution was concentrated, and 20 parts of acetonitrile was added to the obtained residue. The resultant mixture was concentrated. To the residue obtained, 40 parts of ethyl acetate was added, and the resultant mixture was stirred at 23° C. for 1 hour and then, filtrated to obtain 5.42 parts of a salt represented by the formula (I3). This is called as Salt I3.

MS (ESI(+) Spectrum): $M^+$ 263.1

MS (ESI(−) Spectrum): $M^−$ 517.1

Example 4

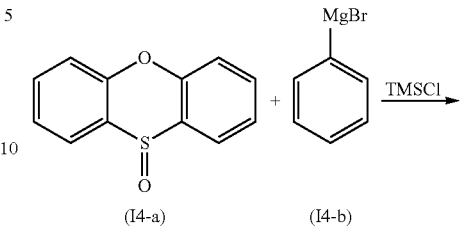

(I4-a)    (I4-b)

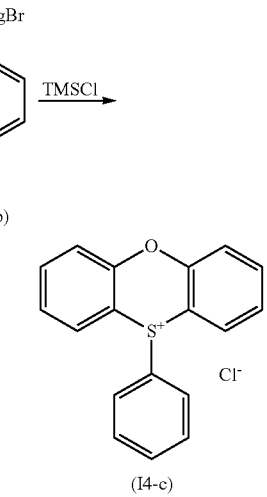

(I4-c)

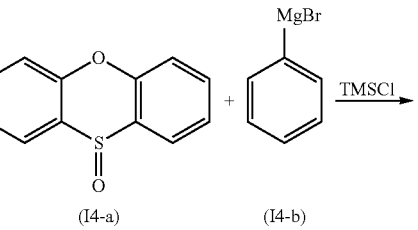

(I4-c)

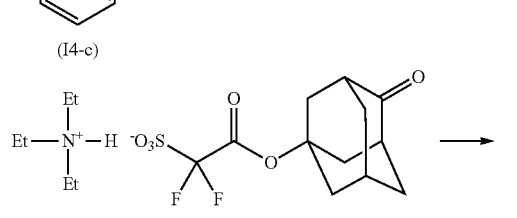

(I2-b)

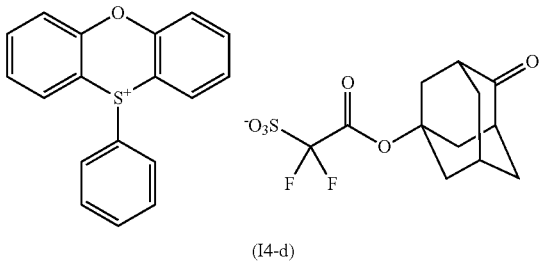

(I4-d)

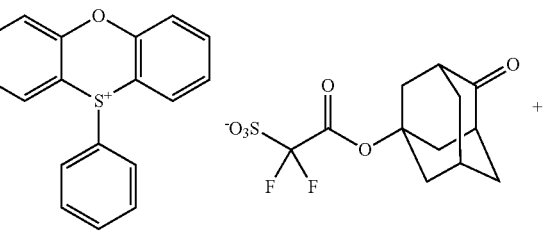

(I4-d)

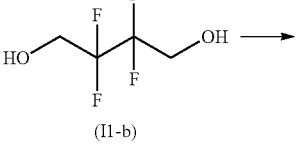

(I1-b)

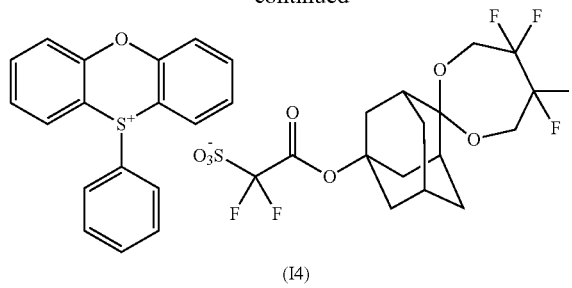

(I4)

A mixture of 50 parts of a compound represented by the formula (I4-a) and 250 parts of tetrahydrofuran was stirred at 30° C. for 30 minutes. To the mixture, 50.23 parts of trimethylsilyl chloride was added dropwise. The resultant mixture was cooled down to 0° C., and then, 157.2 parts of a compound represented by the formula (I4-b) which was available from Tokyo Chemical Industry Co., LTD. and of which purity was 32% was added dropwise to the mixture over 30 minutes. The resultant mixture was heated up to 23° C., and then, stirred at 23° C. for 1 hour. To the reaction mixture obtained, 125 parts of 1N hydrochloric acid was added to conduct separation. The aqueous layer obtained was washed with 125 parts of tert-butyl methyl ether. The aqueous layer was extracted with 125 parts of chloroform, and the organic layer obtained was filtrated followed by concentration. To the residue obtained, 28.33 parts of acetonitrile and 354.15 parts of tert-butyl methyl ether were added, and the resultant mixture was stirred at 23° C. for 30 minutes followed by filtrating the precipitate to obtain 53 parts of a salt represented by the formula (I4-c).

A mixture of 15.17 parts of the salt represented by the formula (I2-a), 25.00 parts of the salt represented by the formula (I2-b) of which purity was 90.8%, 125 parts of chloroform and 41.67 parts of ion-exchanged water was stirred at 23° C.' for 12 hours. The mixture obtained was separated to an organic layer and an aqueous layer. The organic layer obtained was washed nine times with 31.25 parts of ion-exchanged water. To the organic layer, 1 part of active carbon was added to stir at 23° C. for 30 minutes followed by filtration. The filtrate obtained was concentrated. To the residue obtained, 50 parts of acetonitrile was added to prepare a solution. The obtained solution was concentrated, and 150 parts of tert-butyl methyl ether was added to the obtained residue. The resultant mixture was filtrated to obtain 24.28 parts of a salt represented by the formula (I4-d).

A mixture of 10.24 parts of the salt represented by the formula (I4-d) and 40.96 parts of 1,2-dichloroethane was stirred at 23° C. for 30 minutes. To the mixture, 5.53 parts of the compound represented by the formula (I1-b) and 0.3 part of p-toluenesulfonic acid were added, and the resultant mixture was refluxed at 100° C. for 3 hours with stirring. The obtained mixture was cooled down to 23° C., and then, 120 parts of chloroform and 35.39 parts of 8.7% aqueous sodium hydrogen carbonate solution were added thereto followed by conducting stirring at 23° C. for 30 minutes. The mixture obtained was separated to an organic layer and an aqueous layer. The organic layer obtained was washed seven times with 120 parts of ion-exchanged water at 23° C. To the organic layer, 1 part of active carbon was added to stir at 23° C. for 30 minutes followed by filtration. The filtrate obtained was concentrated. To the residue obtained, 20 parts of acetonitrile was added to prepare a solution. The obtained solution was concentrated, and 3 parts of acetonitrile and 50 parts of tart-butyl methyl ether were added to the obtained residue. The resultant mixture was stirred at 23° C. for 1 hour and then, filtrated to obtain 7.22 parts of a salt represented by the formula (I4).

This is called as Salt I4.

MS (ESI(+) Spectrum): $M^+$ 277.1

MS (ESI(−) Spectrum): $M^-$ 467.1

Example 5

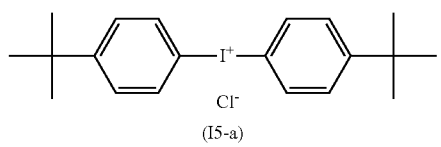

(I5-a)

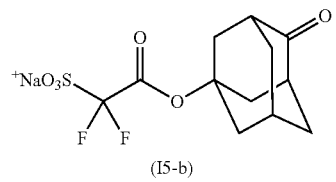

(I5-b)

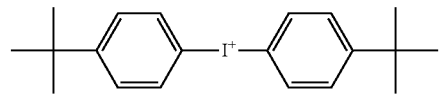

(I5-c)

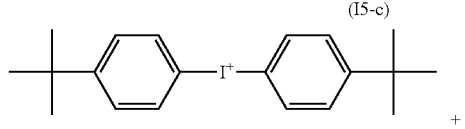

(I5-c)

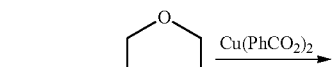

(I5-d)

(I5-e)

-continued

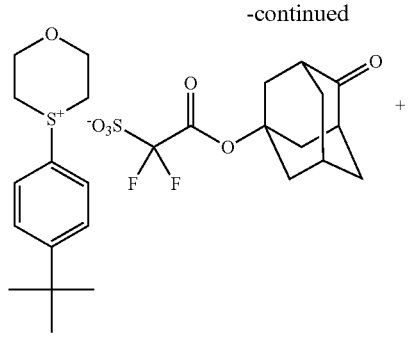

(I5-e)

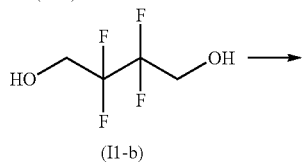

(I1-b)

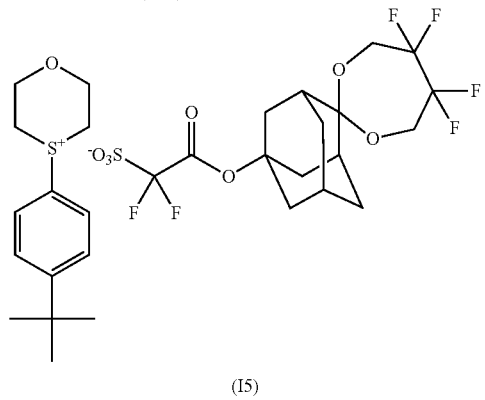

(I5)

A mixture of 10 parts of the compound represented by the formula (I5-b) which had been prepared according to the method described in JP 2008-209917 A, 11.26 parts of the salt represented by the formula (I5-a), 50 parts of chloroform and 25 parts of ion-exchanged water was stirred at 23° C. for 15 hours. The mixture obtained was separated to obtain a chloroform layer. The chloroform layer was washed five times with 15 parts of ion-exchanged water. The chloroform layer was concentrated. To the residue obtained, 50 parts of tert-butyl methyl ether was added, and the resultant mixture was stirred at 23° C. for 30 minutes. The mixture was filtrated to obtain 11.75 parts of a salt represented by the formula (I5-c).

A mixture of 11.71 parts of the salt represented by the formula (I5-c), 1.70 parts of the compound represented by the formula (I5-d) and 46.84 parts of chlorobenzene was stirred at 23° C. for 30 minutes. To the mixture, 0.12 part of copper (II) benzoate was added, and then, the resultant mixture was stirred at 100° C. for 30 minutes. The solution obtained was concentrated. To the residue obtained, 50 parts of chloroform and 12.5 parts of ion-exchanged water were added to stir at 23° C. for 30 minutes. The mixture obtained was separated to obtain an organic layer. The organic layer was washed eight times with 12.5 parts of ion-exchanged water at 23° C. The organic layer was concentrated. To the residue obtained, 50 parts of tert-butyl methyl ether was added and the resultant mixture was stirred and then, filtrated to obtain 6.84 parts of a salt represented by the formula (I5-e).

A mixture of 4.98 parts of the salt represented by the formula (I5-e) and 25 parts of chloroform was stirred at 23° C. for 30 minutes. To the mixture, 2.17 parts of the compound represented by the formula (I1-b) and 0.09 part of sulfuric acid were added, and the resultant mixture was refluxed at 60° C. for 15 hours with stirring. The obtained mixture was cooled down to 23° C., and then, 120 parts of ion-exchanged water was added thereto followed by conducting stirring at 23° C. for 30 minutes. The mixture obtained was separated to an organic layer and an aqueous layer. The organic layer obtained was washed seven times with 12.5 parts of ion-exchanged water at 23° C. To the organic layer, 1 part of active carbon was added to stir at 23° C. for 30 minutes followed by filtration. The filtrate obtained was concentrated. To the residue obtained, 10 parts of acetonitrile was added to prepare a solution. The obtained solution was concentrated, and 41.35 parts of tert-butyl methyl ether was added to the obtained residue. The supernatant was removed, and the residue obtained was dissolved in acetonitrile. The solution obtained was concentrated to obtain 4.84 parts of a salt represented by the formula (I5). This is called as Salt I5.

MS (ESI(+) Spectrum): $M^+$ 237.1

MS (ESI(−) Spectrum): $M^−$ 467.1

Monomers used in the following Resin Synthesis Examples 1 to 6 are following monomers (A), (B), (C), (D), (E) and (F).

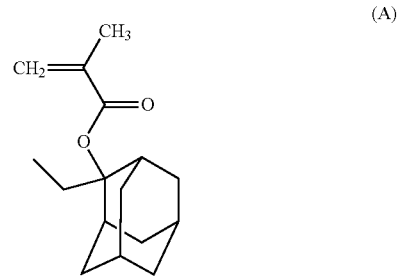

(A)

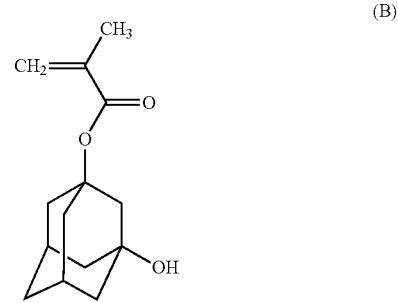

(B)

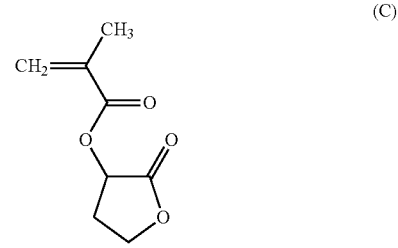

(C)

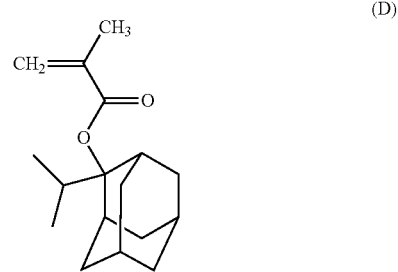

(D)

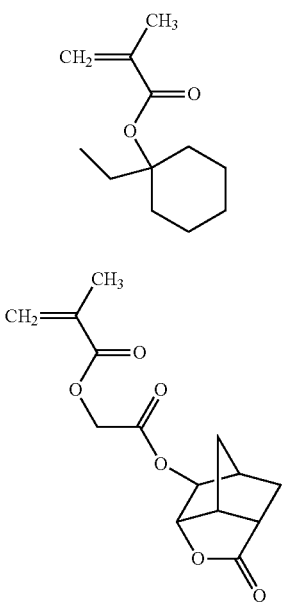

(E)

(F)

Resin Synthesis Example 1

The monomers (D), (E), (B), (C) and (F) were mixed in a molar ratio of 30/14/6/20/30 (monomer (D)/monomer (E)/monomer (B)/monomer (C)/monomer (F)), and 1,4-dioxane in 1.5 times part based on total parts of all monomers was added to prepare a mixture. To the mixture, azobisisobutyronitrile as an initiator in a ratio of 1 mol % based on all monomer molar amount and azobis(2,4-dimethylvaleronitrile) as an initiator in a ratio of 3 mol % based on all monomer molar amount were added, and the obtained mixture was heated at 73° C. for about 5 hours. The reaction mixture obtained was poured into a large amount of a mixture of methanol and water (weight ratio=4/1) to cause precipitation. The precipitate was collected by filtration and then, was dissolved in 1,4-dioxane followed by poured the resultant solution into a large amount of a mixture of methanol and water to cause precipitation. This operation was repeated again for purification. As a result, a resin having a weight-average molecular weight of about $8.1 \times 10^3$ was obtained in a yield of 65%. This resin is called as resin A1. Resin A1 had the following structural units.

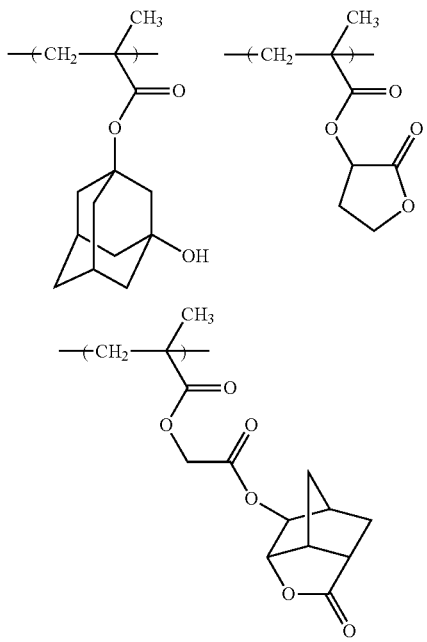

Resin Synthesis Example 2

The monomers (A), (a), (B) (C) and (F) were mixed in a molar ratio of 30/14/6/20/30 (monomer (A)/monomer (E)/monomer (B)/monomer (C)/monomer (F)), and 1,4-dioxane in 1.5 times part based on total parts of all monomers was added to prepare a mixture. To the mixture, azobisisobutyronitrile as an initiator in a ratio of 1 mol % based on all monomer molar amount and azobis(2,4-dimethylvaleronitrile) as an initiator in a ratio of 3 mol % based on all monomer molar amount were added, and the obtained mixture was heated at 73° C. for about 5 hours. The reaction mixture obtained was poured into a large amount of a mixture of methanol and water (weight ratio=4/1) to cause precipitation. The precipitate was collected by filtration and then, was dissolved in 1,4-dioxane followed by poured the resultant solution into a large amount of a mixture of methanol and water to cause precipitation. This operation was repeated twice for purification. As a result, a resin having a weight-average molecular weight of about $7.8 \times 10^3$ was obtained in a yield of 68%. This resin is called as resin A2. Resin A2 had the following structural units.

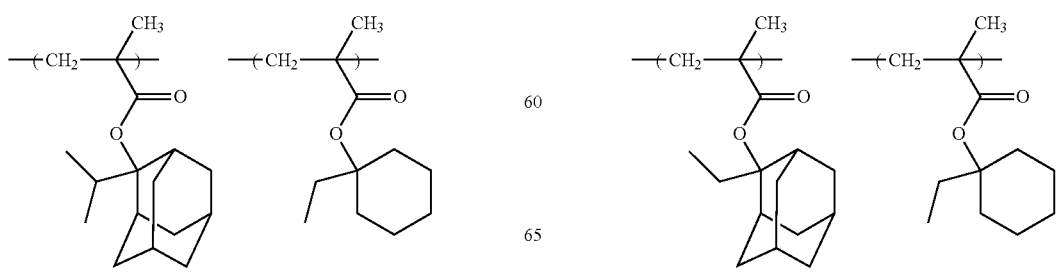

-continued

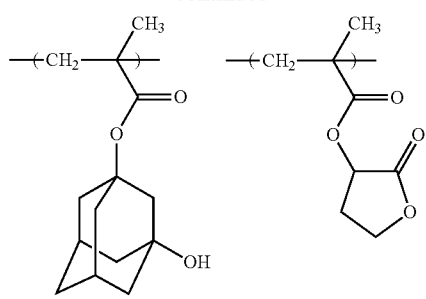

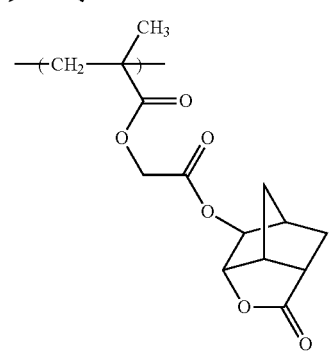

Resin Synthesis Example 3

The monomers (A), (B) and (C) were mixed in a molar ratio of 50/25/25 (monomer (A)/monomer (B)/monomer (C)), and 1,4-dioxane in 1.5 times part based on total parts of all monomers was added to prepare a mixture. To the mixture, azobisisobutyronitrile as an initiator in a ratio of 1 mol % based on all monomer molar amount and azobis(2,4-dimethylvaleronitrile) as an initiator in a ratio of 3 mol % based on all monomer molar amount were added, and the obtained mixture was heated at 80° C. for about 8 hours. The reaction mixture obtained was poured into a large amount of a mixture of methanol and water (weight ratio=4/1) to cause precipitation. The precipitate was collected by filtration and then, was dissolved in 1,4-dioxane followed by poured the resultant solution into a large amount of a mixture of methanol and water to cause precipitation. This operation was repeated twice for purification. As a result, a resin having a weight-average molecular weight of about $9.2 \times 10^3$ was obtained in a yield of 60%. This resin is called as resin A3. Resin A3 had the following structural units.

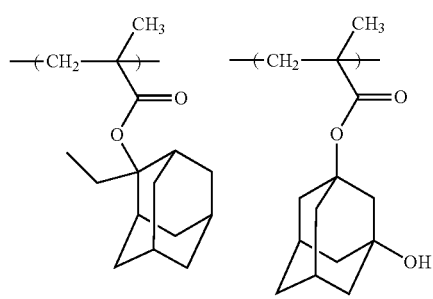

-continued

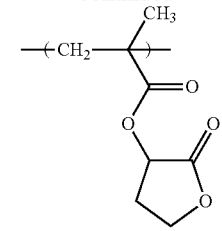

Examples 6 to 13 and Comparative Example 1

Resin

Resin A1, A2, A3
<Acid Generator>
I1: Salt I1
I2: Salt I2
I3: Salt I3
I4: Salt I4
I5: Salt I5
B1:

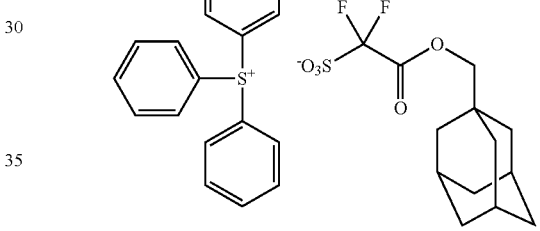

B2:

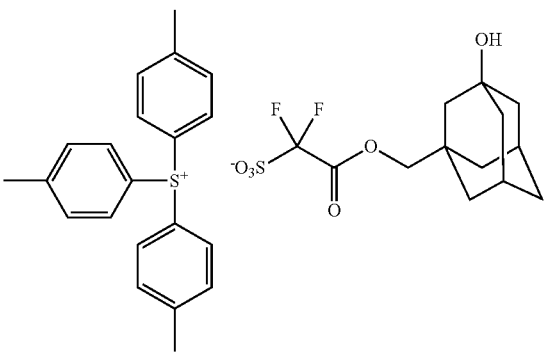

<Quencher>
C1: 2,6-diisopropylaniline
<Solvent>

| E1: | propylene glycol monomethyl ether acetate | 265 parts |
| --- | --- | --- |
| | propylene glycol monomethyl ether | 20 parts |
| | 2-heptanone | 20 parts |
| | γ-butyrolactone | 3.5 parts |

The following components were mixed and dissolved, further, filtrated through a fluorine resin filter having pore diameter of 0.2 μm, to prepare photoresist compositions.
Resin (kind and amount are described in Table 1)
Acid generator (kind and amount are described in Table 1)
Quencher (kind and amount are described in Table 1)
Solvent E1

TABLE 1

| Ex. No. | Resin (kind/amount (part)) | Acid generator (kind/amount (part)) | Quencher (kind/amount (part)) | PB (° C.) | PEB (° C.) |
|---|---|---|---|---|---|
| Ex. 6 | A1/10 | I1/0.7 | C1/0.07 | 95 | 95 |
| Ex. 7 | A2/10 | I1/0.7 | C1/0.07 | 105 | 105 |
| Ex. 8 | A2/10 | I1/0.4 B2/0.3 | C1/0.07 | 105 | 105 |
| Ex. 9 | A3/10 | I1/0.7 | C1/0.07 | 105 | 105 |
| Ex. 10 | A2/10 | I2/0.7 | C1/0.07 | 105 | 105 |
| Ex. 11 | A2/10 | I3/0.7 | C1/0.07 | 105 | 105 |
| Ex. 12 | A2/10 | I4/0.7 | C1/0.07 | 105 | 105 |
| Ex. 13 | A2/10 | I4/0.4 B2/0.3 | C1/0.07 | 105 | 105 |
| Comp. Ex. 1 | A3/10 | B1/0.7 | C1/0.07 | 105 | 105 |

Silicon wafers (12 inches) were each coated with "ARC-29", which is an organic anti-reflective coating composition available from Nissan Chemical Industries, Ltd., and then baked at 205° C. for 60 seconds, to form a 78 nm-thick organic anti-reflective coating. Each of the photoresist compositions prepared as above was spin-coated over the anti-reflective coating so that the thickness of the resulting film became 85 nm after drying. The silicon wafers thus coated with the respective photoresist compositions were each pre-baked on a direct hotplate at a temperature shown in the column "PB" in Table 1 for 60 seconds. Using an ArF excimer stepper for immersion exposure ("XT: 1900Gi" manufactured by ASML, 3/4 Annular, X-Y polarization), each wafer thus formed with the respective resist film was subjected to line and space pattern exposure with the exposure quantity being varied stepwise. Ultrapure water was used as an immersion medium.

After the exposure, each wafer was subjected to post-exposure baking on a hotplate at a temperature shown in the column "PEB" in Table 1 for 60 seconds and then to paddle development for 60 seconds with an aqueous solution of 2.38 wt % tetramethylammonium hydroxide.

Each of patterns developed on the organic anti-reflective coating substrate after the development was observed with a scanning electron microscope, the results of which are shown in Table 2.

Effective Sensitivity (ES): It was expressed as the amount of exposure that the line width of the line and space pattern of 50 nm became 1:1 after exposure through line and space pattern mask and development.

Focus margin (DOF): The photoresist patterns were obtained at the exposure amount of ES, with the focal point distance being varied stepwise. Each of patterns developed on the organic anti-reflective coating substrate after the development were observed and the focal point distances when the patterns of which hole diameter were within 50 nm±5% (between 47.5 nm and 52.5 nm) were measured and the difference between the max value of the focal point distance and the minimum value of the focal point distance was calculated. When the difference is more than 0.17 μm, DOF is very good and its evaluation is marked by "⊚⊚", when the difference is more than 0.14 μm and 0.17 μm or less, DOF is good and its evaluation is marked by "⊚", when the difference is more than 0.09 μm and 0.14 μm or less, DOF is usual and its evaluation is marked by "○", and when the difference is 0.09 μm or less, DOF is bad and its evaluation is marked by "X". Further, each of the differences is also shown in parentheses in a column of "DOF". The difference is bigger, the better focus margin the photoresist composition has.

TABLE 2

| Ex. No. | DOF |
|---|---|
| Ex. 6 | ⊚ (0.15) |
| Ex. 7 | ⊚⊚ (0.18) |
| Ex. 8 | ⊚⊚ (0.21) |
| Ex. 9 | ○ (0.12) |
| Ex. 10 | ⊚⊚ (0.21) |
| Ex. 11 | ⊚⊚ (0.21) |
| Ex. 12 | ⊚ (0.15) |
| Ex. 13 | ⊚⊚ (0.24) |
| Comp. Ex. 1 | X (0.03) |

The salt of the present invention is suitable for an acid generator and the photoresist composition comprising the salt of the present invention provides a good photoresist pattern having good focus margin.

What is claimed is:

1. A salt represented by the formula (I):

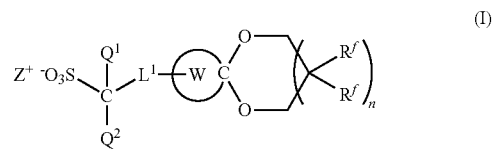

wherein $Q^1$ and $Q^2$ independently each represent a fluorine atom or a C1-C6 perfluoroalkyl group, $L^1$ represents a C1-C17 divalent saturated hydrocarbon group in which one or more —CH$_2$— can be replaced by —O— or —CO—, ring W represents a C3-C36 aliphatic ring in which one or more —CH$_2$— can be replaced by —O—, —S—, —CO— or —SO$_2$— and in which one or more hydrogen atoms can be replaced by a hydroxyl group, a C1-C12 alkyl group, a C1-C12 alkoxy group, a C3-C12 alicyclic hydrocarbon group or a C6-C10 aromatic hydrocarbon group, $R^f$ is independently in each occurrence a fluorine atom or a C1-C6 fluorinated alkyl group, n represents an integer of 1 to 10, and $Z^+$ represents an organic counter ion.

2. The salt according to claim 1, wherein ring W is a ring represented by the formula (Ia1-1), (Ia1-2) or (Ia1-3):

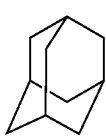
(Ia1-1)

(Ia1-2)

(Ia1-3)

wherein one or more —$CH_2$— in the above-mentioned formula can be replaced by —O—, —S—, —CO— or —$SO_2$— and one or more hydrogen atoms can be replaced by a hydroxyl group, a C1-C12 alkyl group, a C1-C12 alkoxy group, a C3-C12 alicyclic hydrocarbon group or a C6-C10 aromatic hydrocarbon group.

3. The salt according to claim 1, wherein $L^1$ is —CO—O—$(CH_2)_t$— in which * represents a binding position to —$C(Q^1)(Q^2)$- and t represents an integer of 0 to 6.

4. The salt according to claim 1, wherein $Z^+$ is an arylsulfonium cation.

5. An acid generator comprising the salt according to claim 1.

6. A photoresist composition comprising the acid generator according to claim 5 and a resin having an acid-labile group, being insoluble or poorly soluble in an aqueous alkali solution but becoming soluble in an aqueous alkali solution by the action of an acid.

7. The photoresist composition according to claim 6, which further comprises a basic compound.

8. A process for producing a photoresist pattern comprising the following steps (1) to (5):
   (1) a step of applying the photoresist composition according to claim 6 or 7 on a substrate,
   (2) a step of forming a photoresist film by conducting drying,
   (3) a step of exposing the photoresist film to radiation,
   (4) a step of baking the exposed photoresist film, and
   (5) a step of developing the baked photoresist film with an alkaline developer, thereby forming a photoresist pattern.

* * * * *